United States Patent
LaVoie et al.

(10) Patent No.: US 11,845,742 B2
(45) Date of Patent: Dec. 19, 2023

(54) THERAPEUTIC COMPOUNDS AND METHODS TO TREAT INFECTION

(71) Applicants: RUTGERS, THE STATE UNIVERSITY OF NEW JERSEY, New Brunswick, NJ (US); TAXIS PHARMACEUTICALS, INC., Monmouth Junction, NJ (US)

(72) Inventors: Edmond J. LaVoie, New Brunswick, NJ (US); Hye Yeon Sagong, Monmouth Junction, NJ (US); Ajit K. Parhi, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/763,521

(22) PCT Filed: Nov. 13, 2018

(86) PCT No.: PCT/US2018/060816
§ 371 (c)(1),
(2) Date: May 12, 2020

(87) PCT Pub. No.: WO2019/099402
PCT Pub. Date: May 23, 2019

(65) Prior Publication Data
US 2020/0325124 A1 Oct. 15, 2020

Related U.S. Application Data

(60) Provisional application No. 62/586,003, filed on Nov. 14, 2017.

(51) Int. Cl.
| | | |
|---|---|---|
| *C07D 409/12* | (2006.01) | |
| *C07D 209/14* | (2006.01) | |
| *C07D 209/70* | (2006.01) | |
| *A61K 45/06* | (2006.01) | |

(52) U.S. Cl.
CPC ......... *C07D 409/12* (2013.01); *C07D 209/14* (2013.01); *C07D 209/70* (2013.01); *A61K 45/06* (2013.01)

(58) Field of Classification Search
CPC .................. C07D 209/04; C07D 409/12
See application file for complete search history.

(56) References Cited

U.S. PATENT DOCUMENTS

| | | |
|---|---|---|
| 7,855,228 B2 | 12/2010 | Gitai et al. |
| 9,926,261 B2 | 3/2018 | Lavoie et al. |
| 9,950,993 B2 | 4/2018 | Lavoie et al. |
| 2017/0368116 A1 | 12/2017 | Regeimbal et al. |
| 2019/0055188 A1 | 2/2019 | Lavoie et al. |
| 2019/0084919 A1 | 3/2019 | Lavoie et al. |

FOREIGN PATENT DOCUMENTS

| | | | | |
|---|---|---|---|---|
| WO | WO 2014/015291 A1 | * | 1/2014 | |
| WO | WO-2016004513 A1 | * | 1/2016 | .......... C07D 405/04 |
| WO | 2018165611 A1 | | 9/2018 | |
| WO | 2018165612 A1 | | 9/2018 | |
| WO | 2018165614 A1 | | 9/2018 | |
| WO | 2018218192 A1 | | 11/2018 | |
| WO | 2019005841 A1 | | 1/2019 | |

OTHER PUBLICATIONS

Drain, et al. Document No. 55:48733, retrieved from STN; entered in STN on Apr. 22, 2001.*
Dodd, et al. Document No. 157:133640, retrieved from STN; Jun. 28, 2012.*
Kornfeld. Document No. 46:8590, retrieved from STN; 1951.*
Rowbottom, et al. Document No. 168:347039, retrieved from STN; Mar. 15, 2018.*
WO2017122754 (Tanaka, et al.) Jul. 20, 2017 (abstract) STN [database online]. CAPLUS[retrieved on Mar. 16, 2022] Accession No. 2017:1190526.*
WO2004056784 (Priepke, et al.) Jul. 8, 2004 (abstract) STN [database online]. CAPLUS[retrieved on Mar. 16, 2022] Accession No. 2004:546486.*
Akimoto et al.(Bulletin of the Chemical Society of Japan, 58 (1), 123-30 Jun. 2, 1985 (abstract) STN [database online]. CAPLUS[ retrieved on Mar. 16, 2022] Accession 1985:184986.*
Akimoto, et al. Bull. Chem. Soc. Jpn., 58, 123-130 (1985).*
Awuni, E , et al., "Effect of A22 on the Conformation of Bacterial Actin MreB", International Journal of Molecular Sciences 20, 1304 (2019).

(Continued)

*Primary Examiner* — Shawquia Jackson
(74) *Attorney, Agent, or Firm* — Viksnins Harris Padys Malen LLP

(57) ABSTRACT

Disclosed herein are compounds of formula (I), or a salt thereof and compositions comprising compounds of formula I that exhibit antibacterial activities, when tested alone and/or in combination with a bacterial efflux pump inhibitor. Also disclosed are methods of treating or preventing a bacterial infection in an animal comprising administering to the animal a compound of formula I alone or in combination with the administration of a bacterial efflux pump inhibitor.

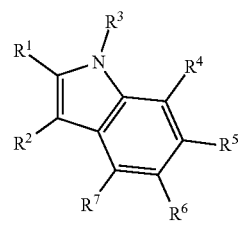

I

18 Claims, No Drawings

(56) References Cited

OTHER PUBLICATIONS

Awuni, Y., et al., "Exploring the A22-Bacterial Actin MreB Interaction through Molecular Dynamics Simulations", J. Phys. Chem, B 120(37), 4867-4874 (2016).

Barker, C., et al., "Degradation of MAC13243 and studies of the interaction of resulting thiourea compounds with the lipoprotein targeting chaperone LoIA", Bioorganic & Medicinal Chemistry Letters 23, 2426-2431 (2013).

Bean, G., et al., "A22 disrupts the bacterial actin cytoskeleton by directly binding and inducing a low-affinity state in MreB", Biochemistry 48 (22), 4852-7 (2009).

Bonez, P., et al., "Antibacterial, cyto and genotoxic activities of A22 compound ((S-3,4-dichlorobenzyl) Isothiourea hydrochloride)", Microbial Pathogenesis 99, 14-18 (2016).

Bonez, P., et al., "Anti-biofilm activity of A22 ((S-3,4-dichlorobenzyl) isothiourea hydrochloride) against Pseudomonas aeruginosa: Influence on biofilm formation, motility and bioadhesion", Microbial Pathogenesis 111, 6-13 (2017).

Iwai, N., et al., "Novel S-Benzylisothiourea Compound That Induces Spherical Cells in *Escherichia coli* Probably by Acting on a Rod-shape-determining Protein(s) Other Than Penicillin-binding Protein 2", Biosci Biotechnol Biochem 66 (12), 2658-2662 (2002).

Iwai, N., et al., "Structure-Activity Relationship of S-Benzylisothiourea Derivatives to Induce Spherical Cells in *Escherichia coli*", Biosci Biotechnol Biochem 68(11), 2265-2269 (2004).

Iwai, N., et al., "Structure-Activity Relationship Study of the Bacterial Actin-Like Protein MreB Inhibitors: Effects of Substitution of Benzyl Group in S-Benzylisothiourea", Biosci. Biotechnol. Biochem 71 (1), 246-248 (2007).

Lee, J., et al., "Roles of Indole as an Interspecies and Interkingdom Signaling Molecule", Trends in Microbiology 23 (11), 707-718 (2015).

Noguchi, N., et al., "Anti-infectious Effect of S-Benzylisothiourea Compound A22, Which Inhibits the Actin-Like Protein, MreB, in Shigella flexneri", Biol. Pharm. Bull 31 (7), 1327-1332 (2008).

Patent Cooperation Treaty, International Searching Authority, Search Report and Written Opinion for PCT/US2018/060816, 11 pages, dated Feb. 19, 2019.

Perry, J., et al., "In vitro activity of S-(3,4-dichlorobenzyl)isothiourea hydrochloride and novel structurally related compounds against multidrug-resistant bacteria, including Pseudomonas aeruginosa and Burkholderia cepacian complex", International Journal of Antimicrobial Agents, 39 (1), 27-32 (2012).

Pubchem, "1H-Indole-2-methaneamine", SID 275115126, 6 pages, deposit date Dec. 24, 2015.

Robertson, GT, et al., "A Novel Indole Compound That Inhibits Pseudomonas aeruginosa Growth by Targeting MreB is a Substrate for MexAB-OprM", Journal of Bacteriology 189 (19), 6870-6881 (2007).

Taylor, P., et al., "A Forward Chemical Screen Identifies Antibiotic Adjuvants in *Escherichia coli*", ACS Chem Biol 7, 1547-1555 (2012).

Yamachika, S., et al., "Anti-Pseudomonas aeruginosa Compound, 1,2,3,4-Tetrahydro-1,3,5-triazine Derivative, Exerts Its Action by Primarily Targeting MreB", Biol Pharm Bull 35(10), 1740-1744 (2012).

\* cited by examiner

THERAPEUTIC COMPOUNDS AND METHODS TO TREAT INFECTION

PRIORITY OF INVENTION

This application claims priority to U.S. Provisional Patent Application No. 62/586,003 filed Nov. 14, 2017. The entire content of the application referenced above is hereby incorporated by reference herein.

BACKGROUND OF THE INVENTION

The emergence of Multidrug Resistant (MDR) bacterial pathogens has increased concerns as to the adequacy of current antimicrobials and pathogen treatment methods. The lethality of pathogens, such as *Pseudomonas aeruginosa*, has often led to treatment methods that are experimental or would otherwise normally be avoided in standard clinical practice. The growing threat from MDR pathogens highlights a critical need for additional antimicrobials. In this connection, there is a pressing need for new antibiotics that exhibit novel mechanisms of action or circumvent conventional mechanisms of resistance.

Bacteria have developed several different mechanisms to overcome the action of antibiotics. These mechanisms of resistance can be specific such as for a molecule or a family of antibiotics, or the mechanisms can be non-specific. Several mechanisms of resistance can exist in a single bacterial strain, and those mechanisms may act independently, or they may act synergistically to overcome the action of an antibiotic or a combination of antibiotics. Specific mechanisms include, for example, degradation of the drug, inactivation of the drug by enzymatic modification, and alteration of the drug target. Additional mechanisms of drug resistance include mechanisms in which access of the antibiotic to the target is prevented or reduced by decreasing the transport of the antibiotic into the cell or by increasing the efflux of the drug from the cell to the outside medium. These mechanisms can lower the concentration of drug at the target site and allow bacterial survival in the presence of one or more antibiotics that would otherwise inhibit or kill the bacterial cells. Some bacteria utilize both mechanisms, combining low permeability of the cell wall (including membranes) with an active efflux of antibiotics. It has been shown that efflux of antibiotics can be mediated by more than one pump in a single organism and that almost all antibiotics are subject to resistance by this mechanism. For example, *Pseudomonas aeruginosa* expresses numerous efflux pumps including MexAB-OprM, MexCD-OprJ, MexEF-OprN, and MexXY-OprA(OprM) which actively efflux various antibacterial agents.

These multiple resistance mechanisms have become widespread and threaten the clinical utility of antibacterial therapy. The increase in antibiotic resistant strains has been particularly noted in major hospitals and care centers. The consequences of the increase in resistant strains include, for example higher morbidity and mortality, longer patient hospitalization, and an increase in treatment costs. Accordingly, there is a need for methods and combinations of agents for treating bacterial infections.

MreB is a well conserved and essential cytoskeleton-like protein, which represents a bacterial homolog of actin. Studies with various MreB homologs have established that this protein forms dynamic, actin-like helical filaments in an ATP- or GTP-dependent fashion. The filaments are localized within the bacterial cell on the inner surface of the cytoplasmic membrane. MreB protein provides a critical role in the maintenance of cell shape, polar protein localization, and/or chromosome segregation. Because of its essential role in bacterial growth and function, MreB inhibitors represent a novel class of antibacterial agents.

The MreB homolog of *P. aeruginosa* is essential for cell viability as well as maintenance of rod-like cell morphology. CBR-4830 was identified as an effective MreB inhibitor in *P. aeruginosa* while screening libraries of compounds against a *P. aeruginosa* strains with defective efflux transporters.

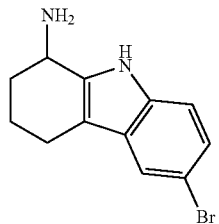

CBR-4830

CBR-4830 is a substrate for the MexAB-OprM efflux transporter present in wild-type *P. aeruginosa*, which limited its efficacy and clinical promise. Thus, there is an ongoing need for antibacterial agents (e.g., MreB inhibitors). There is also a need for antibacterial agents (e.g., MreB inhibitors) that have improved properties such as improved formulation characteristics or lowered toxicity.

SUMMARY OF THE INVENTION

Compounds disclose herein exhibit antibacterial activities, when tested alone and/or in combination with a bacterial efflux pump inhibitor.

One embodiment provides a compound of formula I

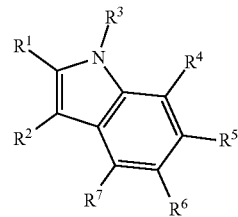

$R^1$ is $(C_1-C_{12})$alkyl substituted with one or more (e.g., 1, 2, 3, 4, or 5) or $NR^aR^b$ and wherein the $(C_1-C_{12})$alkyl is optionally substituted with one or more (e.g., 1, 2, 3, 4, or 5) halo, hydroxyl, or phenyl wherein the phenyl is optionally substituted independently with one or more (e.g., 1, 2, 3, 4, or 5) halo, cyano, $(C_1-C_3)$alkyl, or $(C_1-C_3)$haloalkyl, and $R^2$ is hydrogen or $(C_1-C_8)$alkyl optionally substituted with one or more (e.g., 1, 2, 3, 4, or 5) halo, hydroxyl, oxo, or $NR^aR^b$, or $R^1$ and $R^2$ together with the atoms to which they are attached form a 5 or 7-membered carbocycle wherein the carbocycle is substituted with one or more (e.g., 1, 2, 3, 4, or 5) $NR^aR^b$ and wherein the carbocycle is optionally substituted with one or more (e.g., 1, 2, 3, 4, or 5) halo, hydroxyl, $NR^aR^b$, or $(C_1-C_4)$alkyl wherein the $(C_1-C_4)$ alkyl is optionally substituted with one or more (e.g., 1, 2, 3, 4, or 5) $NR^aR^b$;

$R^3$ is hydrogen or $(C_1-C_4)$alkyl;

$R^4$ is hydrogen, halo, cyano, $(C_1-C_6)$alkyl, $(C_1-C_6)$haloalkyl, $(C_1-C_6)$alkoxy, $(C_1-C_6)$haloalkoxy, or phenyl wherein the phenyl is optionally substituted with one or more (e.g., 1, 2, 3, 4, or 5) halo, $(C_1-C_6)$haloalkyl, cyano, nitro or $(C_1-C_6)$haloalkoxy;

$R^5$ is hydrogen, halo, cyano, $(C_1-C_6)$alkyl, $(C_1-C_6)$haloalkyl, $(C_1-C_6)$alkoxy, $(C_1-C_6)$haloalkoxy, or phenyl wherein the phenyl is optionally substituted with one or more (e.g., 1, 2, 3, 4, or 5) halo, $(C_1-C_6)$haloalkyl, cyano, nitro or $(C_1-C_6)$haloalkoxy;

$R^6$ is hydrogen, halo, cyano, $(C_1-C_6)$alkyl, $(C_1-C_6)$haloalkyl, $(C_1-C_6)$alkoxy, $(C_1-C_6)$haloalkoxy, or phenyl wherein the phenyl is optionally substituted with one or more (e.g., 1, 2, 3, 4, or 5) halo, $(C_1-C_6)$haloalkyl, cyano, nitro or $(C_1-C_6)$haloalkoxy; and $R^7$ is hydrogen, halo, cyano, $(C_1-C_6)$alkyl, $(C_1-C_6)$haloalkyl, $(C_1-C_6)$alkoxy, $(C_1-C_6)$haloalkoxy, or phenyl wherein the phenyl is optionally substituted with one or more (e.g., 1, 2, 3, 4, or 5) halo, $(C_1-C_6)$haloalkyl, cyano, nitro or $(C_1-C_6)$haloalkoxy;

each $R^a$ is independently hydrogen or $(C_1-C_6)$alkyl wherein the $(C_1-C_6)$alkyl is optionally substituted with one or more (e.g., 1, 2, 3, 4, or 5) halo, hydroxyl, $NR^cR^d$, $R^g$, —C(=O)$NR^{e1}R^{e2}$, —OR, or —O$(C_1-C_3)$alkyl-$R^f$;

each $R^b$ is independently hydrogen, or $(C_1-C_6)$alkyl wherein the $(C_1-C_6)$alkyl is optionally substituted with one or more (e.g., 1, 2, 3, 4, or 5) halo, hydroxyl, or $NR^cR^d$;

each $R^c$ is independently hydrogen, $(C_1-C_3)$alkyl, —C(=O)$R^h$, phenyl, $C_3-C_7$carbocycle, or —$(C_1-C_6)$alkylphenyl wherein the phenyl, $C_3-C_7$carbocycle, or —$(C_1-C_6)$alkylphenyl is optionally substituted independently with one or more (e.g., 1, 2, 3, 4, or 5) halo, cyano, $(C_1-C_6)$alkyl, or $(C_1-C_6)$haloalkyl;

each $R^d$ is independently hydrogen or $(C_1-C_3)$alkyl;

each $R^{e1}$ is phenyl optionally substituted independently with one or more (e.g., 1, 2, 3, 4, or 5) halo, cyano, $(C_1-C_6)$alkyl, or $(C_1-C_6)$haloalkyl;

each $R^{e2}$ is independently hydrogen or $(C_1-C_3)$alkyl;

each $R^f$ is phenyl optionally substituted independently with one or more (e.g., 1, 2, 3, 4, or 5) halo, cyano, $(C_1-C_6)$alkyl, or $(C_1-C_6)$haloalkyl;

each $R^g$ is independently 5-6 membered heteroaryl, phenyl, or $C_3-C_7$carbocycle wherein the 5-6 membered heteroaryl, phenyl, or $C_3-C_7$carbocycle is optionally substituted independently with one or more (e.g., 1, 2, 3, 4, or 5) halo, cyano, $(C_1-C_6)$alkyl, or $(C_1-C_6)$haloalkyl; and each $R^h$ is independently 5-6 membered heteroaryl, phenyl, or $C_3-C_7$carbocycle wherein the 5-6 membered heteroaryl, phenyl, or $C_3-C_7$carbocycle is optionally substituted independently with one or more (e.g., 1, 2, 3, 4, or 5) halo, cyano, $(C_1-C_6)$alkyl, or $(C_1-C_6)$haloalkyl;

or a salt thereof.

One embodiment provides a compound of formula I:

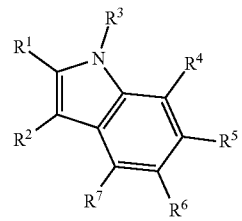

$R^1$ is $(C_1-C_{20})$alkyl substituted with one or more or $NR^aR^b$ and wherein the $(C_1-C_2)$alkyl is optionally substituted with one or more halo or hydroxyl and $R^2$ is hydrogen or $(C_1-C_8)$alkyl optionally substituted with one or more halo, hydroxyl, oxo, or $NR^aR^b$, or $R^1$ and $R^2$ together with the atoms to which they are attached form a 5 or 7-membered carbocycle wherein the carbocycle is substituted with one or more or $NR^aR^b$ and wherein the carbocycle is optionally substituted with one or more halo, hydroxyl, $NR^aR^b$, or $(C_1-C_4)$alkyl wherein the $(C_1-C_4)$alkyl is optionally substituted with one or more $NR^aR^b$;

$R^3$ is hydrogen or $(C_1-C_4)$alkyl;

$R^4$ is hydrogen, halo, $(C_1-C_6)$alkyl, $(C_1-C_6)$haloalkyl, $(C_1-C_6)$alkoxy, $(C_1-C_6)$haloalkoxy, or phenyl wherein the phenyl is optionally substituted with one or more halo, $(C_1-C_6)$haloalkyl, nitro or $(C_1-C_6)$haloalkoxy;

$R^5$ is hydrogen, halo, $(C_1-C_6)$alkyl, $(C_1-C_6)$haloalkyl, $(C_1-C_6)$alkoxy, $(C_1-C_6)$haloalkoxy; or phenyl wherein the phenyl is optionally substituted with one or more halo, $(C_1-C_6)$haloalkyl, nitro or $(C_1-C_6)$haloalkoxy;

$R^6$ is hydrogen, halo, $(C_1-C_6)$alkyl, $(C_1-C_6)$haloalkyl, $(C_1-C_6)$alkoxy, $(C_1-C_6)$haloalkoxy, or phenyl wherein the phenyl is optionally substituted with one or more halo, $(C_1-C_6)$haloalkyl, nitro or $(C_1-C_6)$haloalkoxy; and $R^7$ is hydrogen, halo, $(C_1-C_6)$alkyl, $(C_1-C_6)$haloalkyl, $(C_1-C_6)$alkoxy, $(C_1-C_6)$haloalkoxy, or phenyl wherein the phenyl is optionally substituted with one or more halo, $(C_1-C_6)$haloalkyl, nitro or $(C_1-C_6)$haloalkoxy;

each $R^a$ is independently hydrogen or $(C_1-C_6)$alkyl wherein the $(C_1-C_6)$alkyl is optionally substituted with one or more halo, hydroxyl, or $NR^cR^d$;

each $R^b$ is independently hydrogen, $(C_1-C_6)$alkyl wherein the $(C_1-C_6)$alkyl is optionally substituted with one or more halo, hydroxyl, or $NR^cR^d$;

each $R^c$ is independently hydrogen or $(C_1-C_3)$alkyl; and each $R^d$ is independently hydrogen or $(C_1-C_3)$alkyl;

or a salt thereof.

One embodiment provides a pharmaceutical composition comprising a compound of formula I or a pharmaceutically acceptable salt thereof as described herein and a pharmaceutically acceptable excipient.

One embodiment provides a compound of formula I or a pharmaceutically acceptable salt thereof as described herein for use in medical therapy.

One embodiment provides a compound of formula I or a pharmaceutically acceptable salt thereof as described herein for the prophylactic or therapeutic treatment of a bacterial infection in an animal (e.g., a mammal such as a human).

One embodiment provides a compound of formula I or a pharmaceutically acceptable salt thereof as described herein for the preparation of a medicament for treating a bacterial infection in an animal (e.g., a mammal such as a human).

One embodiment provides a method of treating or preventing a bacterial infection in an animal (e.g., a mammal such as a human) comprising administering to the animal a compound of formula I or a pharmaceutically acceptable salt thereof as described herein.

One embodiment provides a method of treating or preventing a bacterial infection in an animal (e.g., a mammal such as a human) comprising administering to the animal a bacterial efflux pump inhibitor and a compound of formula I or a pharmaceutically acceptable salt thereof as described herein.

One embodiment provides a pharmaceutical composition comprising a compound of formula I or a pharmaceutically acceptable salt thereof as described herein, a bacterial efflux pump inhibitor, and a pharmaceutically acceptable vehicle.

One embodiment provides a compound of formula I or a pharmaceutically acceptable salt thereof as described herein, combined with a bacterial efflux pump inhibitor, for use in medical therapy.

One embodiment provides a compound of formula I or a pharmaceutically acceptable salt thereof as described herein, combined with a bacterial efflux pump inhibitor, for the prophylactic or therapeutic treatment of a bacterial infection in an animal (e.g., a mammal such as a human).

One embodiment provides the use of a compound of formula I or a pharmaceutically acceptable salt thereof as described herein, combined with a bacterial efflux pump inhibitor, for the preparation of a medicament for treating a bacterial infection in an animal (e.g., a mammal such as a human).

One embodiment provides processes and intermediates disclosed herein that are useful for preparing compounds of formula I or salts thereof.

DETAILED DESCRIPTION

The following definitions are used, unless otherwise described: halo or halogen is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to).

As used herein, the term "$(C_a-C_b)$alkyl" wherein a and b are integers refers to a straight or branched chain alkyl radical having from a to b carbon atoms. Thus, when a is 1 and b is 6, for example, the term includes methyl, ethyl, n-propyl, isopropyl, n-butyl, isobutyl, sec-butyl, t-butyl, n-pentyl and n-hexyl.

The term "aryl" as used herein refers to a single aromatic ring or a multiple condensed ring system wherein the ring atoms are carbon. For example, an aryl group can have 6 to 10 carbon atoms, or 6 to 12 carbon atoms. Aryl includes a phenyl radical. Aryl also includes multiple condensed ring systems (e.g., ring systems comprising 2 rings) having about 9 to 12 carbon atoms or 9 to 10 carbon atoms in which at least one ring is aromatic. Such multiple condensed ring systems may be optionally substituted with one or more (e.g., 1 or 2) oxo groups on any cycloalkyl portion of the multiple condensed ring system. It is to be understood that the point of attachment of a multiple condensed ring system, as defined above, can be at any position of the ring system including an aryl or a cycloalkyl portion of the ring. Typical aryl groups include, but are not limited to, phenyl, indenyl, naphthyl, 1,2,3,4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 rings) wherein a heteroaryl group, as defined above, can be condensed with one or more heteroaryls (e.g., naphthyridinyl), heterocycles, (e.g., 1,2,3,4-tetrahydronaphthyridinyl), cycloalkyls (e.g., 5,6,7,8-tetrahydroquinolyl) or aryls (e.g. indazolyl) to form a multiple condensed ring system. Such multiple condensed ring systems may be optionally substituted with one or more (e.g., 1 or 2) oxo groups on the cycloalkyl or heterocycle portions of the condensed ring. In one embodiment a monocyclic or bicyclic heteroaryl has 5 to 10 ring atoms comprising 1 to 9 carbon atoms and 1 to 4 heteroatoms. It is to be understood that the point of attachment of a multiple condensed ring system (as defined above for a heteroaryl) can be at any position of the multiple condensed ring system including a heteroaryl, heterocycle, aryl or cycloalkyl portion of the multiple condensed ring system and at any suitable atom of the multiple condensed ring system including a carbon atom and heteroatom (e.g., a nitrogen).

Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl and thianaphthenyl.

The term cycloalkyl, carbocycle, or carbocyclyl includes saturated and partially unsaturated carbocyclic ring systems. In one embodiment the cycloalkyl is a monocyclic carbocyclic ring. Such cycloalkyls include "$(C_3-C_7)$carbocyclyl" and "$(C_3-C_8)$cycloalkyl".

The term "heterocyclyl" or "heterocycle" as used herein refers to a single saturated or partially unsaturated ring or a multiple condensed ring system. The term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. It is to be understood that the point of attachment for a heterocycle can be at any suitable atom of the heterocycle Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl and tetrahydrothiopyranyl.

The term "haloalkyl" includes an alkyl group as defined herein that is substituted with one or more (e.g., 1, 2, 3, 4, or 5) halo groups (e.g., trifluoromethyl, difluoromethyl etc.). One specific halo alkyl is a "$(C_1-C_6)$haloalkyl".

The term "alkoxy" refers to —O(alkyl) and the term "haloalkoxy" refers to an alkoxy that is substituted with one or more (e.g., 1, 2, 3, 4, or 5)halo(e.g., trifluoromethoxy or pentafluoroethoxy).

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy.

It is understood that the embodiments provided below are for compounds of formula I and all sub-formulas thereof (e.g., formulas Ia). It is to be understood the two or more embodiments may be combined.

In one embodiment $R^1$ is $(C_1-C_{20})$alkyl substituted with one or more or $NR^aR^b$ and wherein the $(C_1-C_{20})$alkyl is optionally substituted with one or more halo or hydroxyl and $R^2$ is hydrogen or $(C_1-C_8)$alkyl optionally substituted with one or more halo, hydroxyl, oxo, or $NR^aR^b$, or $R^1$ and $R^2$ together with the atoms to which they are attached form a 5 or 7-membered carbocycle wherein the carbocycle is substituted with one or more or $NR^aR^b$ and wherein the carbocycle is optionally substituted with one or more halo, hydroxyl, $NR^aR^b$, or $(C_1-C_4)$alkyl wherein the $(C_1-C_4)$alkyl is optionally substituted with one or more $NR^aR^b$; In one embodiment $R^1$ is $(C_1-C_8)$alkyl substituted with one $NR^aR^b$ and wherein the $(C_1-C_{20})$alkyl is optionally substituted with one or more halo or hydroxyl, and $R^2$ is hydrogen or $(C_1-C_8)$alkyl, or $R^1$ and $R^2$ together with the atoms to which they are attached form a 5 or 7-membered carbocycle wherein the carbocycle is substituted with one $NR^aR^b$ and wherein the carbocycle is optionally substituted with one or more halo, hydroxyl, or $(C_1-C_4)$alkyl.

In one embodiment $R^1$ is $(C_1-C_8)$alkyl substituted with one $NR^aR^b$ and $R^2$ is hydrogen, or $R^1$ and $R^2$ together with the atoms to which they are attached form a 5 or 7-membered carbocycle wherein the carbocycle is substituted with one $NR^aR^b$.

In one embodiment $R^1$ is $(C_1-C_8)$alkyl substituted with one $NR^aR^b$ and $R^2$ is hydrogen.

In one embodiment the compound of formula I is a compound of formula Ia or a salt thereof:

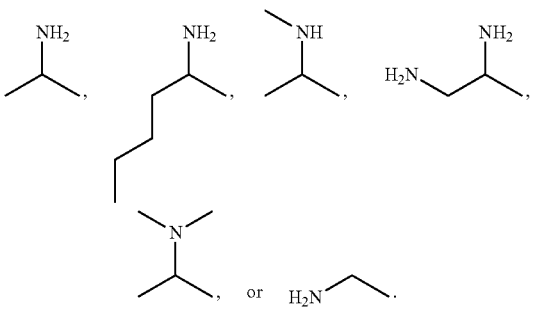

Ia $R^{1a}$ is hydrogen or $(C_1-C_8)$alkyl optionally substituted with one or more halo, hydroxyl, or $NR^aR^b$ and $R^2$ is hydrogen or $(C_1-C_8)$alkyl optionally substituted with one or more halo, hydroxyl, oxo, or $NR^aR^b$, or $R^{1a}$ and $R^2$ together with the atoms to which they are attached form a 5 or 7-membered carbocycle wherein the carbocycle is optionally substituted with one or more halo, hydroxyl, $NR^aR^b$, or $(C_1-C_4)$alkyl wherein the $(C_1-C_4)$alkyl is optionally substituted with one or more $NR^aR^b$; and $R^{1b}$ is hydrogen or $(C_1-C_8)$alkyl optionally substituted with one or more halo, hydroxyl, or $NR^aR^b$.

In one embodiment $R^{1a}$ is hydrogen or $(C_1-C_8)$alkyl optionally substituted with one or more halo, hydroxyl, or $NR^aR^b$ and $R^2$ is hydrogen or $(C_1-C_8)$alkyl optionally substituted with one or more halo, hydroxyl, oxo, or $NR^aR^b$.

In one embodiment $R^{1a}$ is hydrogen or $(C_1-C_8)$alkyl optionally substituted with one or more halo, hydroxyl, or $NR^aR^b$ and $R^2$ is hydrogen or $(C_1-C_8)$alkyl.

In one embodiment $R^{1a}$ is hydrogen or $(C_1-C_8)$alkyl optionally substituted with one or more $NR^aR^b$ and $R^2$ is hydrogen.

In one embodiment $R^{1a}$ is hydrogen, methyl, butyl, or ethylamine.

In one embodiment $R^{1a}$ and $R^2$ together with the atoms to which they are attached form a 5 or 7-membered carbocycle wherein the carbocycle is optionally substituted with one or more halo, hydroxyl, $NR^aR^b$, or $(C_1-C_4)$alkyl wherein the $(C_1-C_4)$alkyl is optionally substituted with one or more $NR^aR^b$.

In one embodiment $R^{1a}$ and $R^2$ together with the atoms to which they are attached form a 5 or 7-membered carbocycle wherein the carbocycle is optionally substituted with one or more $NR^aR^b$ or $(C_1-C_4)$alkyl wherein the $(C_1-C_4)$alkyl is optionally substituted with one or more $NR^aR^b$.

In one embodiment $R^{1b}$ is hydrogen.

In one embodiment each $R^a$ is independently hydrogen or $(C_1-C_6)$alkyl.

In one embodiment each $R^a$ is independently hydrogen or methyl.

In one embodiment each $R^b$ is independently hydrogen or $(C_1-C_6)$alkyl.

In one embodiment each $R^b$ is independently hydrogen or methyl.

In one embodiment $R^1$ or the moiety —CH($NR^aR^b$)$R^{1a}R^{1b}$ of formula Ia is:

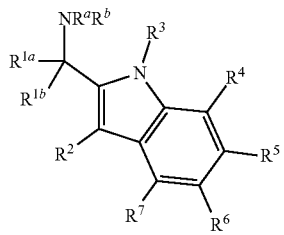

In one embodiment $R^3$ is hydrogen or methyl.

In one embodiment $R^4$ is hydrogen.

In one embodiment $R^4$ is hydrogen or halo.

In one embodiment $R^5$ is hydrogen or halo.

In one embodiment $R^5$ is hydrogen, fluoro, chloro, or bromo.

In one embodiment $R^6$ is hydrogen, halo, $(C_1-C_6)$haloalkyl, $(C_1-C_6)$alkoxy, or $(C_1-C_6)$haloalkoxy.

In one embodiment $R^6$ is hydrogen, fluoro, bromo, trifluoromethyl, methoxy, or trifluoromethoxy.

In one embodiment $R^7$ is hydrogen or halo.

In one embodiment $R^7$ is hydrogen or chloro.

In one embodiment at least one of $R^4$, $R^5$, $R^6$, or $R^7$ is not hydrogen.

In one embodiment at least two of $R^4$, $R^5$, $R^6$, or $R^7$ are not hydrogen.

In one embodiment at least one of $R^4$, $R^5$, $R^6$, or $R^7$ is halo, $(C_1-C_6)$haloalkyl, $(C_1-C_6)$alkoxy, or $(C_1-C_6)$haloalkoxy.

In one embodiment at least two of $R^4$, $R^5$, $R^6$, or $R^7$ are halo, $(C_1-C_6)$haloalkyl, $(C_1-C_6)$alkoxy, or $(C_1-C_6)$haloalkoxy.

One embodiment provides the compound:

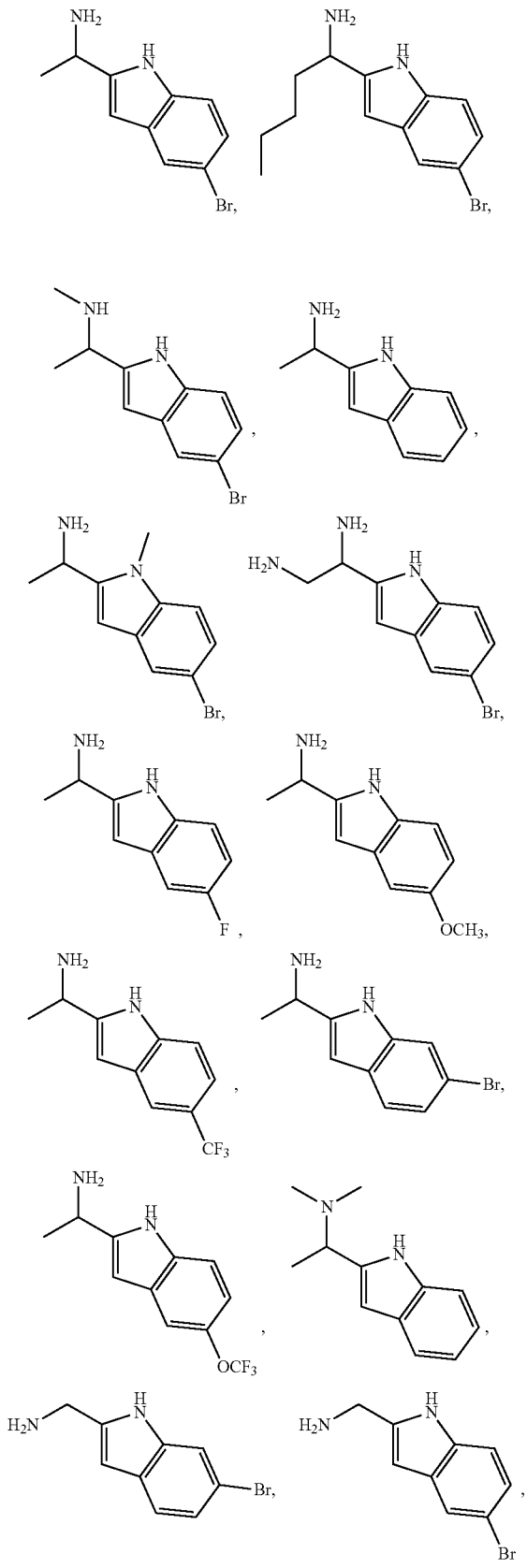

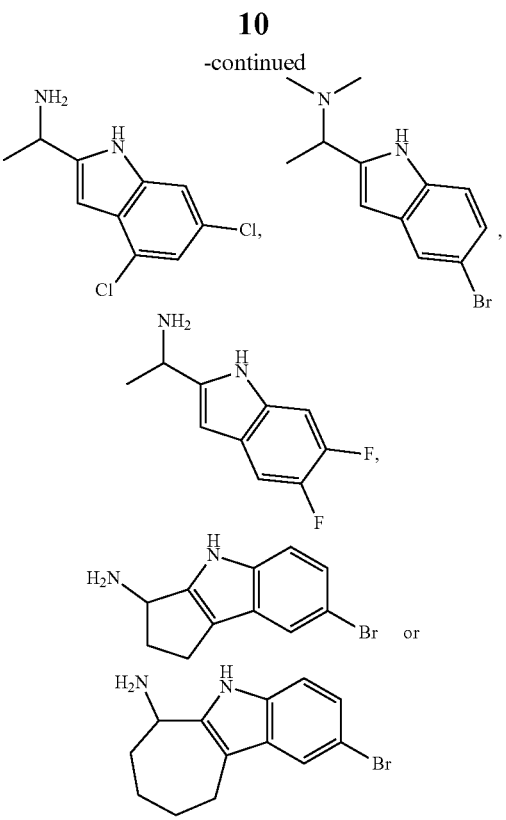

or a salt thereof.

In one embodiment $R^1$ is $(C_1\text{-}C_8)$alkyl substituted with one $NR^aR^b$ and wherein the $(C_1\text{-}C_8)$alkyl is optionally substituted with one or more halo, hydroxyl or phenyl wherein the phenyl is optionally substituted independently with one or more halo, cyano, $(C_1\text{-}C_3)$alkyl, or $(C_1\text{-}C_3)$haloalkyl, and $R^2$ is hydrogen or $(C_1\text{-}C_8)$alkyl, or $R^1$ and $R^2$ together with the atoms to which they are attached form a 5 or 7-membered carbocycle wherein the carbocycle is substituted with one $NR^aR^b$ and wherein the carbocycle is optionally substituted with one or more halo, hydroxyl, or $(C_1\text{-}C_4)$alkyl.

One embodiment provides a compound of formula Ia:

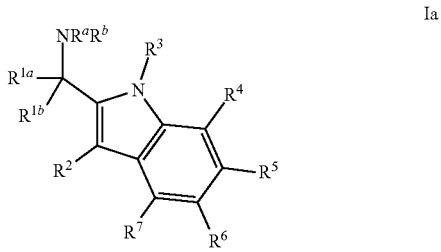

Ia wherein: $R^{1a}$ is hydrogen or $(C_1\text{-}C_8)$alkyl optionally substituted with one or more halo, hydroxyl, $NR^aR^b$, or phenyl wherein the phenyl is optionally substituted independently with one or more halo, cyano, $(C_1\text{-}C_3)$alkyl, or $(C_1\text{-}C_3)$haloalkyl and $R^2$ is hydrogen or $(C_1\text{-}C_8)$alkyl optionally substituted with one or more halo, hydroxyl, oxo, or $NR^aR^b$, or $R^{1a}$ and $R^2$ together with the atoms to which they are attached form a 5 or 7-membered carbocycle wherein the carbocycle is optionally substituted with one or more halo, hydroxyl, NRᵃRᵇ, or (C₁-C₄)alkyl wherein the (C₁-C₄)alkyl is optionally substituted with one or more NRᵃRᵇ; and
R¹ᵇ is hydrogen or (C₁-C₈)alkyl optionally substituted with one or more halo, hydroxyl, or NRᵃRᵇ.

In one embodiment R¹ᵃ is hydrogen or (C₁-C₈)alkyl optionally substituted with one or more halo, hydroxyl, NRᵃRᵇ or phenyl wherein the phenyl is optionally substituted independently with one or more halo, cyano, (C₁-C₃)alkyl, or (C₁-C₃)haloalkyl and R² is hydrogen or (C₁-C₈)alkyl optionally substituted with one or more halo, hydroxyl, oxo, or NRᵃRᵇ.

In one embodiment R¹ᵃ is hydrogen or (C₁-C₈)alkyl optionally substituted with one or more halo, hydroxyl, NRᵃRᵇ or phenyl wherein the phenyl is optionally substituted independently with one or more halo, cyano, (C₁-C₃)alkyl, or (C₁-C₃)haloalkyl and R² is hydrogen or (C₁-C₈)alkyl.

In one embodiment R¹ᵃ is hydrogen or (C₁-C₈)alkyl optionally substituted with one or more NRᵃRᵇ or phenyl wherein the phenyl is optionally substituted independently with one or more halo, cyano, (C₁-C₃)alkyl, or (C₁-C₃)haloalkyl and R² is hydrogen.

In one embodiment R¹ᵃ is hydrogen, methyl, propyl, ethylamine, or phenethyl.

In one embodiment R¹ᵃ is hydrogen, methyl, butyl, ethylamine, or phenethyl.

In one embodiment R¹ᵃ and R² together with the atoms to which they are attached form a 5 or 7-membered carbocycle.

In one embodiment each Rᵃ is independently hydrogen or (C₁-C₆)alkyl wherein the (C₁-C₆)alkyl is optionally substituted with one or more NRᶜRᵈ, Rᵍ, —C(=O)NRᵉ¹Rᵉ², or —ORᶠ.

In one embodiment each Rᶜ is independently (C₁-C₃)alkyl, or —C(=O)Rʰ.

In one embodiment each Rᵈ is hydrogen.

In one embodiment each Rᵉ¹ is phenyl optionally substituted with one or more halo.

In one embodiment each Rᵉ² is hydrogen.

In one embodiment each Rᶠ is phenyl optionally substituted with one or more halo.

In one embodiment each Rᵍ is independently phenyl, or C₃-C₇carbocycle wherein the phenyl or C₃-C₇carbocycle is independently substituted with one or more halo, cyano, (C₁-C₆)alkyl, or (C₁-C₆)haloalkyl.

In one embodiment each Rʰ is independently 5-6 membered heteroaryl, phenyl, or C₃-C₇carbocycle wherein the 5-6 membered heteroaryl, phenyl, or C₃-C₇carbocycle is independently substituted halo.

In one embodiment each Rᵃ is independently hydrogen, methyl,

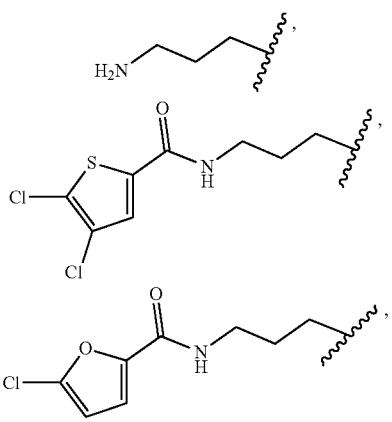

In one embodiment R¹, or the moiety —CH(NRᵃRᵇ)R¹ᵃR¹ᵇ of a compound of formula Ia is:

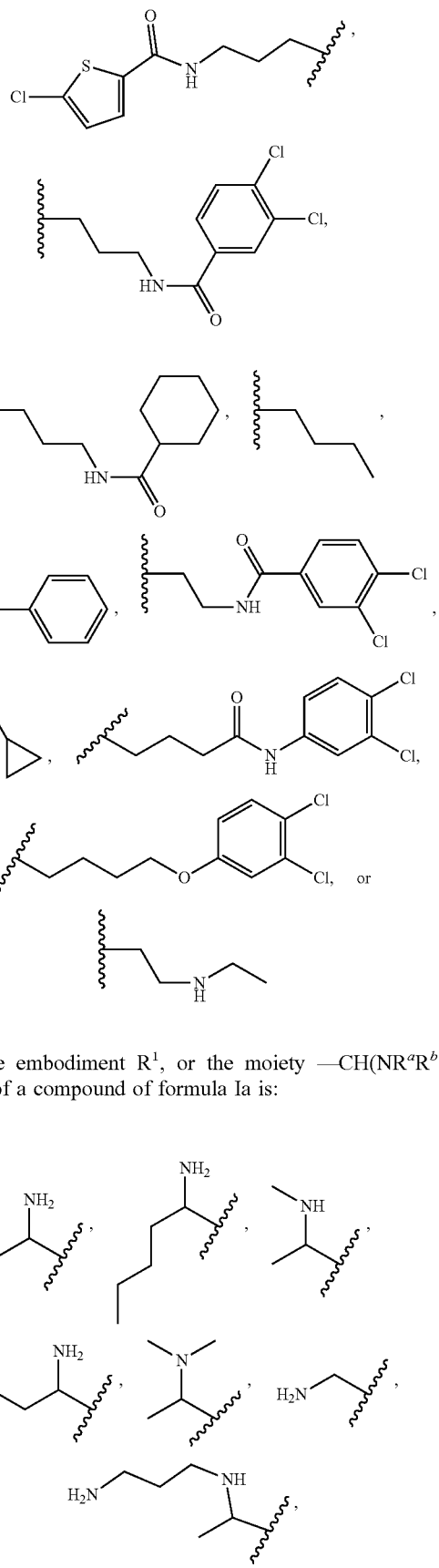

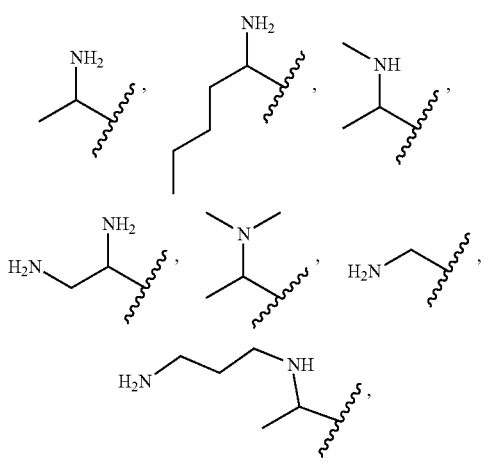

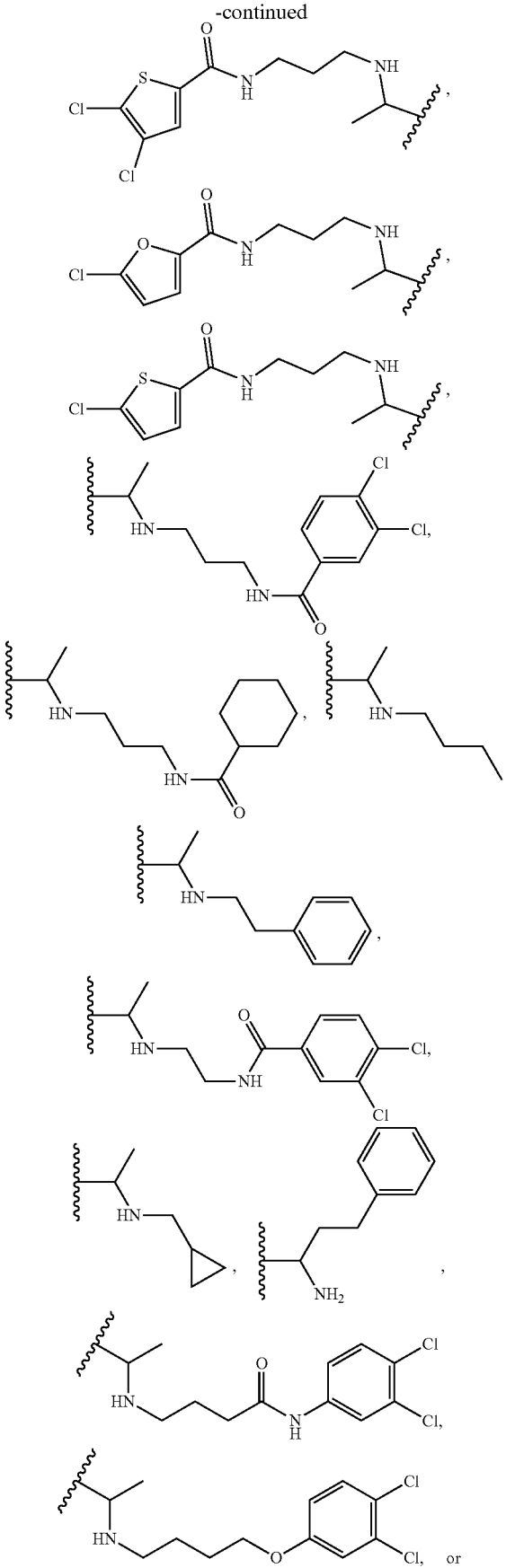

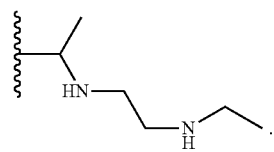

In one embodiment $R^4$ is hydrogen, halo, $(C_1-C_6)$haloalkyl, $(C_1-C_6)$alkoxy, or $(C_1-C_6)$haloalkoxy.

In one embodiment $R^4$ is hydrogen.

In one embodiment $R^5$ is hydrogen, halo, $(C_1-C_6)$haloalkyl, $(C_1-C_6)$alkoxy, or $(C_1-C_6)$haloalkoxy.

In one embodiment $R^6$ is hydrogen, fluoro, chloro, bromo, trifluoromethyl, methoxy, or trifluoromethoxy.

In one embodiment $R^7$ is hydrogen, halo, $(C_1-C_6)$haloalkyl, $(C_1-C_6)$alkoxy, or $(C_1-C_6)$haloalkoxy.

One embodiment provides a compound that is:

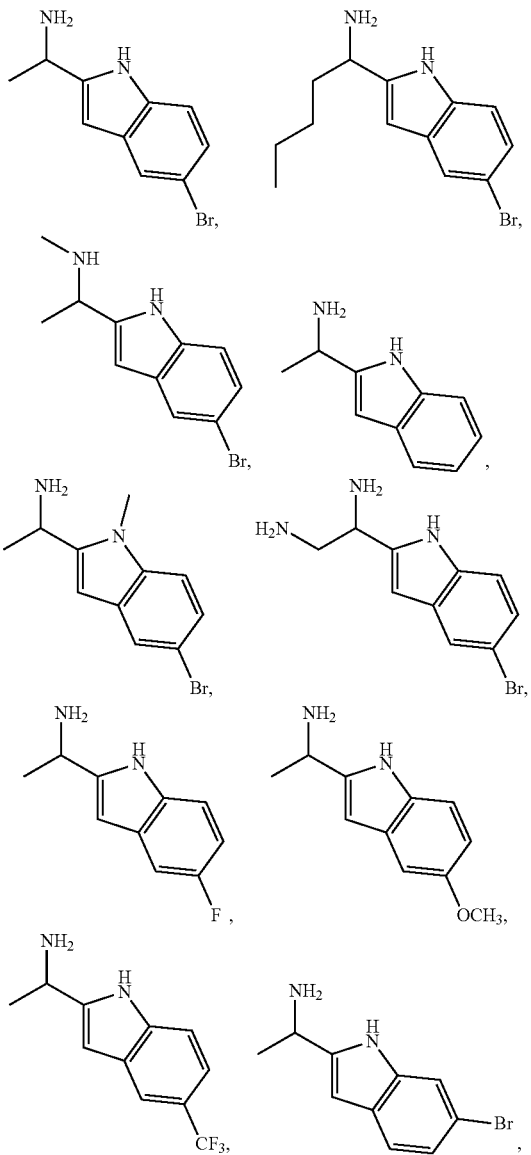

-continued
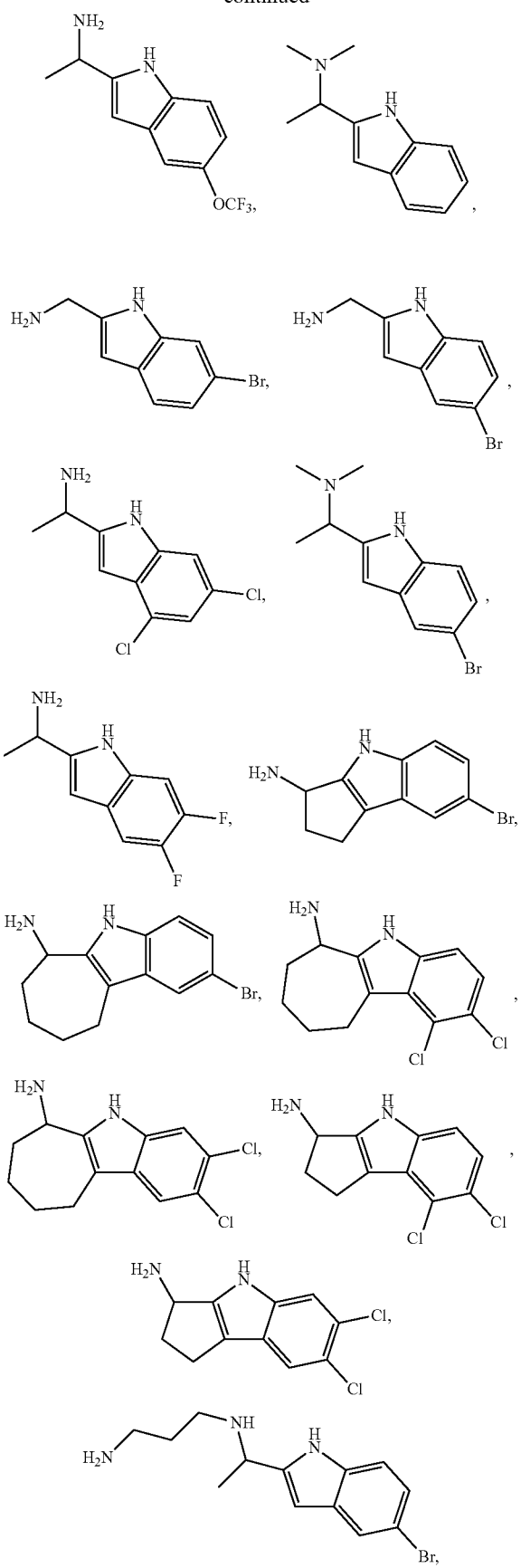
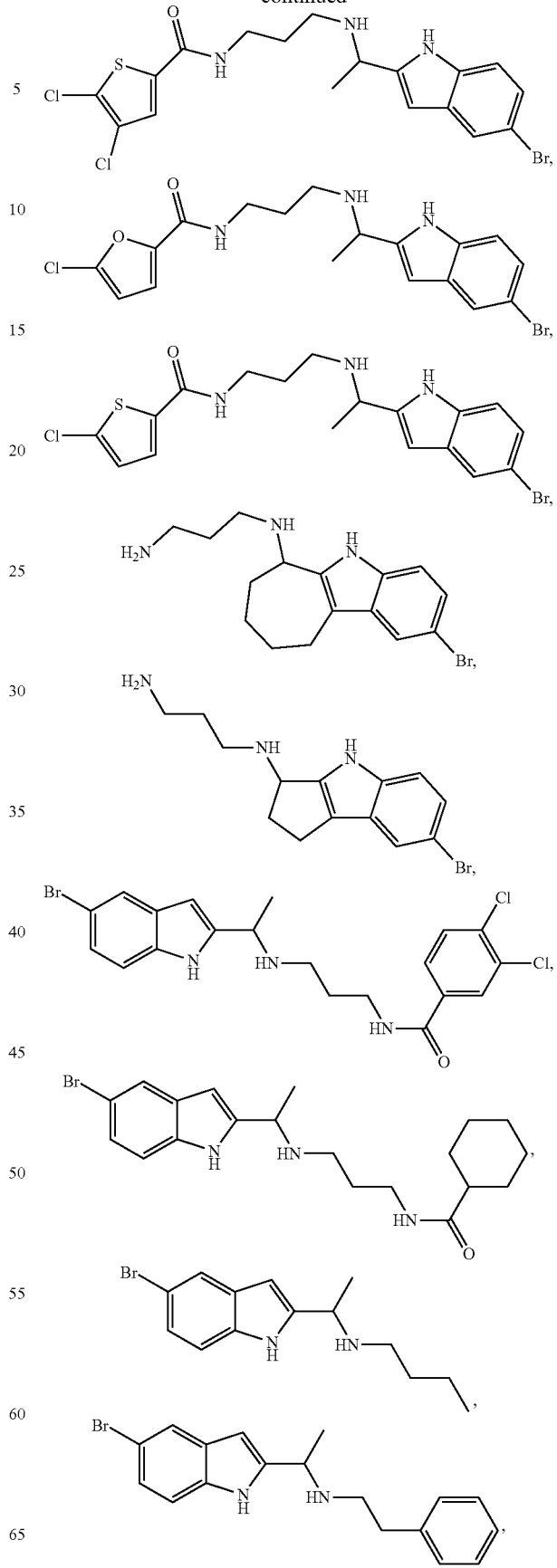

-continued

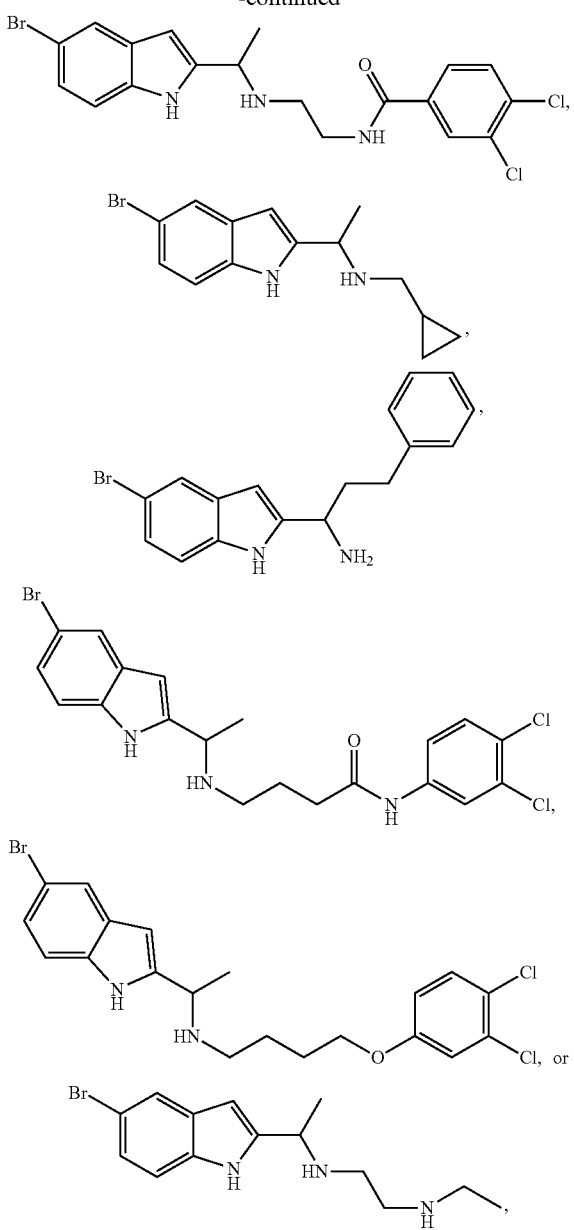

or a salt thereof.

Generally, compounds of formula I as well as synthetic intermediates that can be used for preparing compounds of formula I can be prepared as illustrated in the following General Methods and Schemes. It is understood that variable groups shown below (e.g., R) can represent the final corresponding groups present in a compound of formula I or that these groups can represent groups that can be converted to the final corresponding groups present in a compound of formula I at a convenient point in a synthetic sequence. For example, the variable groups can contain one or more protecting groups that can be removed at a convenient point in a synthetic sequence to provide the final corresponding groups in the compound of formula I. The reagents and conditions shown are exemplary and non-limiting. Other reagents and conditions can be used in the general synthetic schemes.

Scheme 1

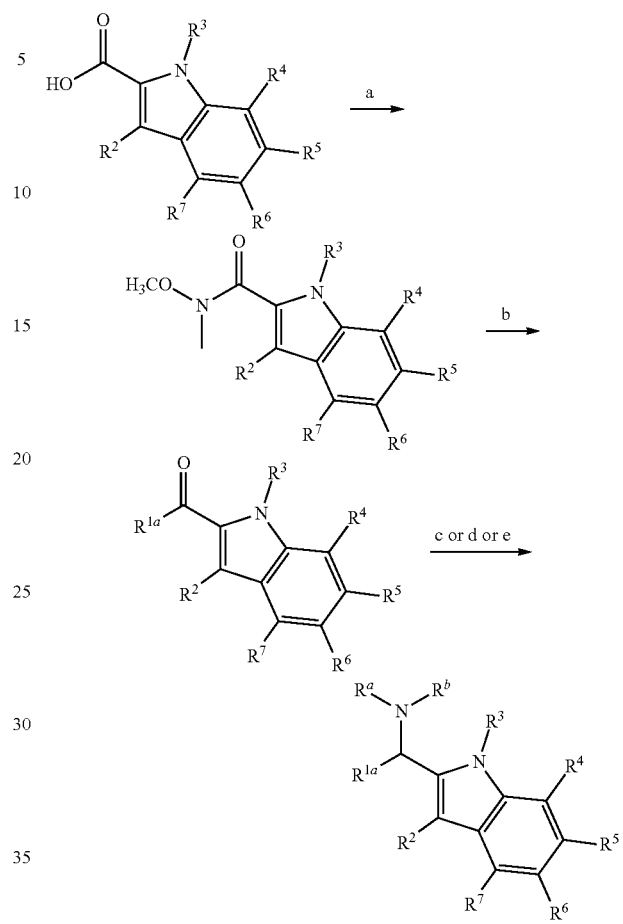

Reagent and Conditions:

(a) $CH_3ONHCH_3 \cdot HCl$, EDC·HCl, HOBt, $NEt_3$, DMF; (b) $R^{1a}Li$ or $R^{1a}MgX$, THF, $-78°$ C.; (c) $NH_4OAc$, $NaBH_3CN$, EtOH, $60°$ C. (for $R^a$, $R^b$=H); (d) 2.0 M methylamine in THF, $NaBH_3CN$, cat. AcOH, EtOH, $60°$ C. (for $R^a$=$CH_3$, $R^b$=H); (e) 2.0 M N,N-dimethylamine in THF, $NaBH_3CN$, cat. AcOH, EtOH, $60°$ C. (for $R^a$, $R^b$=$CH_3$).

Scheme 2

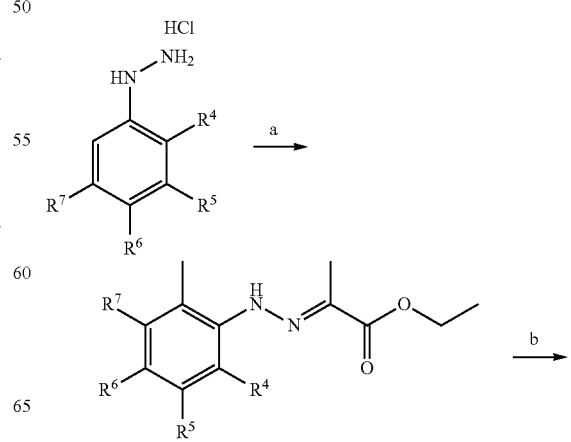

19
-continued

20
-continued

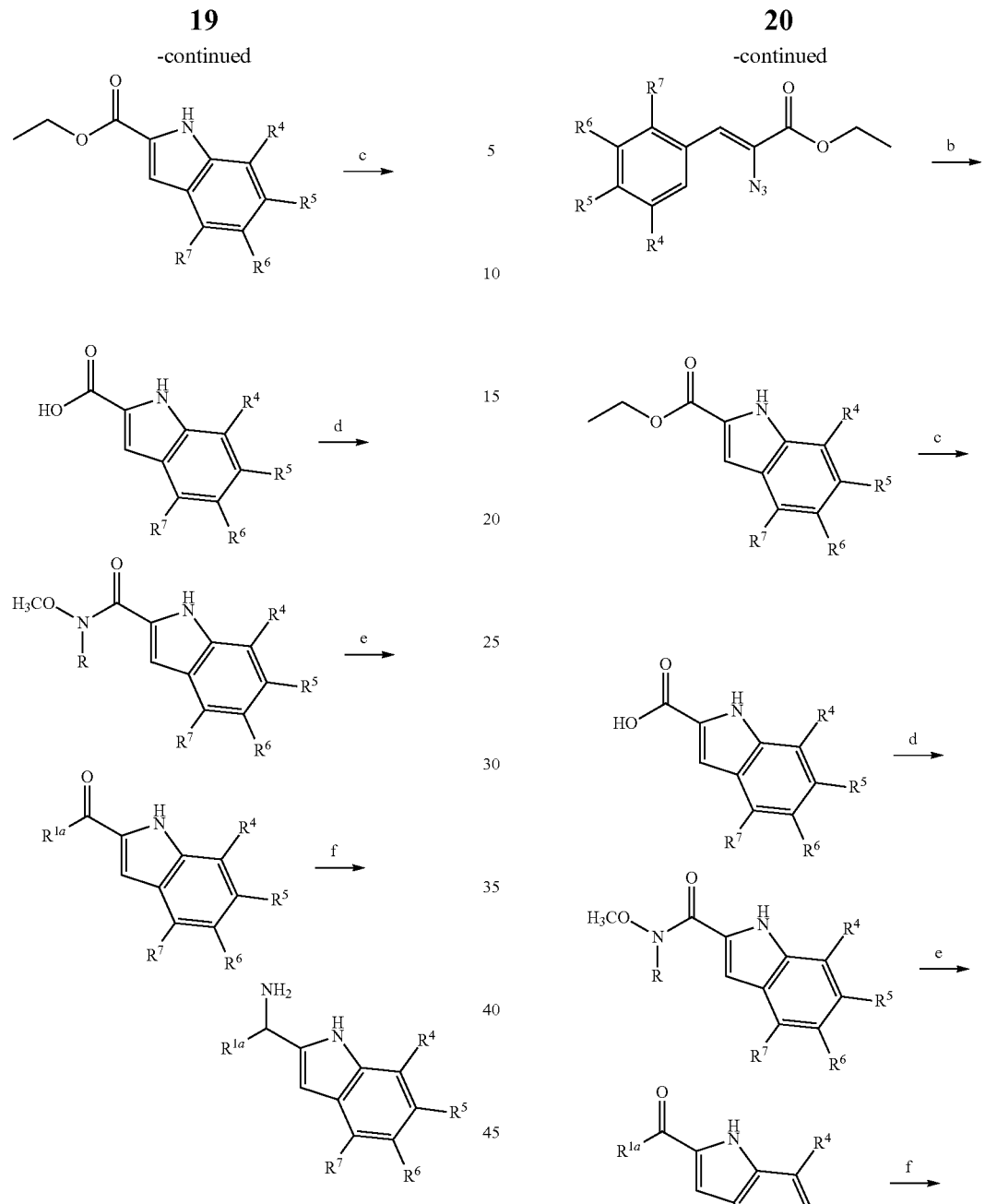

Reagent and Conditions:

(a) ethyl pyruvate, cat. AcOH, EtOH, reflux; (b) TFA or PPA or p-toluenesulfonic acid, toluene, reflux; (c) LiOH, EtOH, reflux; (d) CH$_3$ONHCH$_3$HCl, EDC HCl, HOBt, NEt$_3$, DMF; (e) R$^{1a}$Li or R$^{1a}$MgX, THF, −78° C.; (f) NH$_4$OAc, NaBH$_3$CN, EtOH, 60° C.

Scheme 3

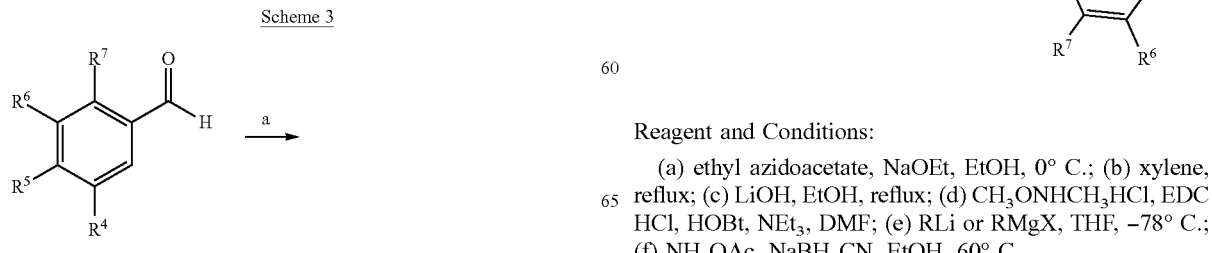

Reagent and Conditions:

(a) ethyl azidoacetate, NaOEt, EtOH, 0° C.; (b) xylene, reflux; (c) LiOH, EtOH, reflux; (d) CH$_3$ONHCH$_3$HCl, EDC HCl, HOBt, NEt$_3$, DMF; (e) RLi or RMgX, THF, −78° C.; (f) NH$_4$OAc, NaBH$_3$CN, EtOH, 60° C.

Scheme 4

Reagent and Conditions:

(a) NaOH, water; (b) NaNO$_2$, conc. HCl, water, 0° C.; (c) NaOAc, methanol, water, 0° C.; (d) conc. HCl, AcOH, 130° C.; (e) NH$_4$OAc, NaBH$_3$CN, EtOH, 60° C.

Scheme 5

Reagent and Conditions:

(a) Boc$_2$O, DMAP, THF; (b) TMSOTf, DCM, 0° C.; (c) NBS, DCM, 0° C.; (d) R$_1$R$_2$NH, DMF; (e) TFA, DCM; (f) NH$_4$OAc, NaBH$_3$CN, EtOH, 60° C.

Scheme 6

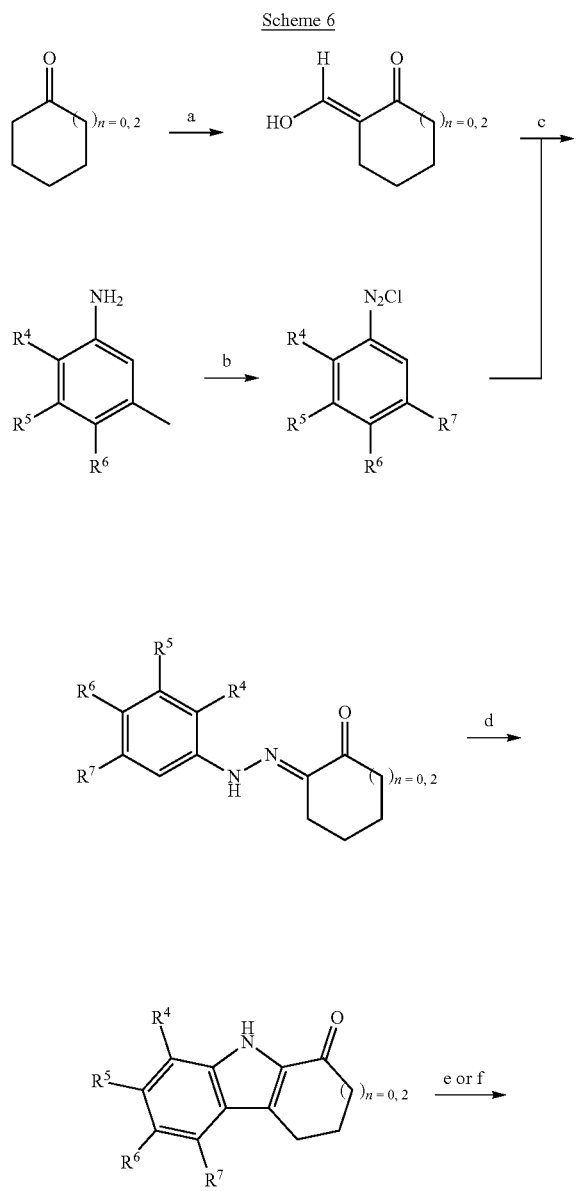

Reagent and Conditions:

(a) LiHMDS, ethyl formate, THF, 0° C.; (b) NaNO₂, conc. HCl, water, 0° C.; (c) NaOAc, methanol, water, 0° C.; (d) conc. HCl, AcOH, 130° C.; (e) NH₄OAc, NaBH₃CN, cat. AcOH, EtOH, 60° C. (for n=0); (f) NH₄OAc, NaBH₃CN, EtOH, 60° C. (for n=2).

Scheme 7

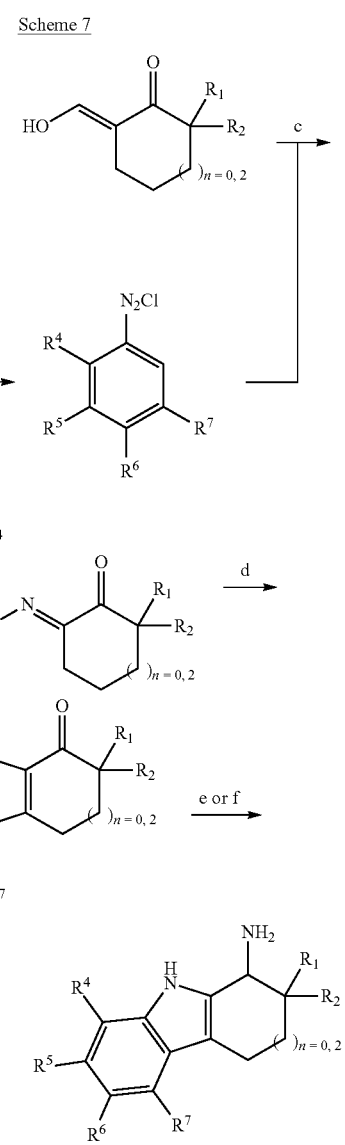

$R_1 = R_2 = (C_1-C_4)$alkyl or F

Reagent and Conditions:

(a) LiHMDS, ethyl formate, THF, 0° C.; (b) NaNO₂, conc. HCl, water, 0° C.; (c) NaOAc, methanol, water, 0° C.; (d) conc. HCl, AcOH, 130° C.; (e) NH₄OAc, NaBH₃CN, cat. AcOH, EtOH, 60° C. (for n=0); (f) NH₄OAc, NaBH₃CN, EtOH, 60° C. (for n=2).

Scheme 8

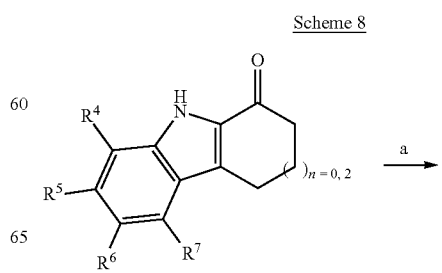

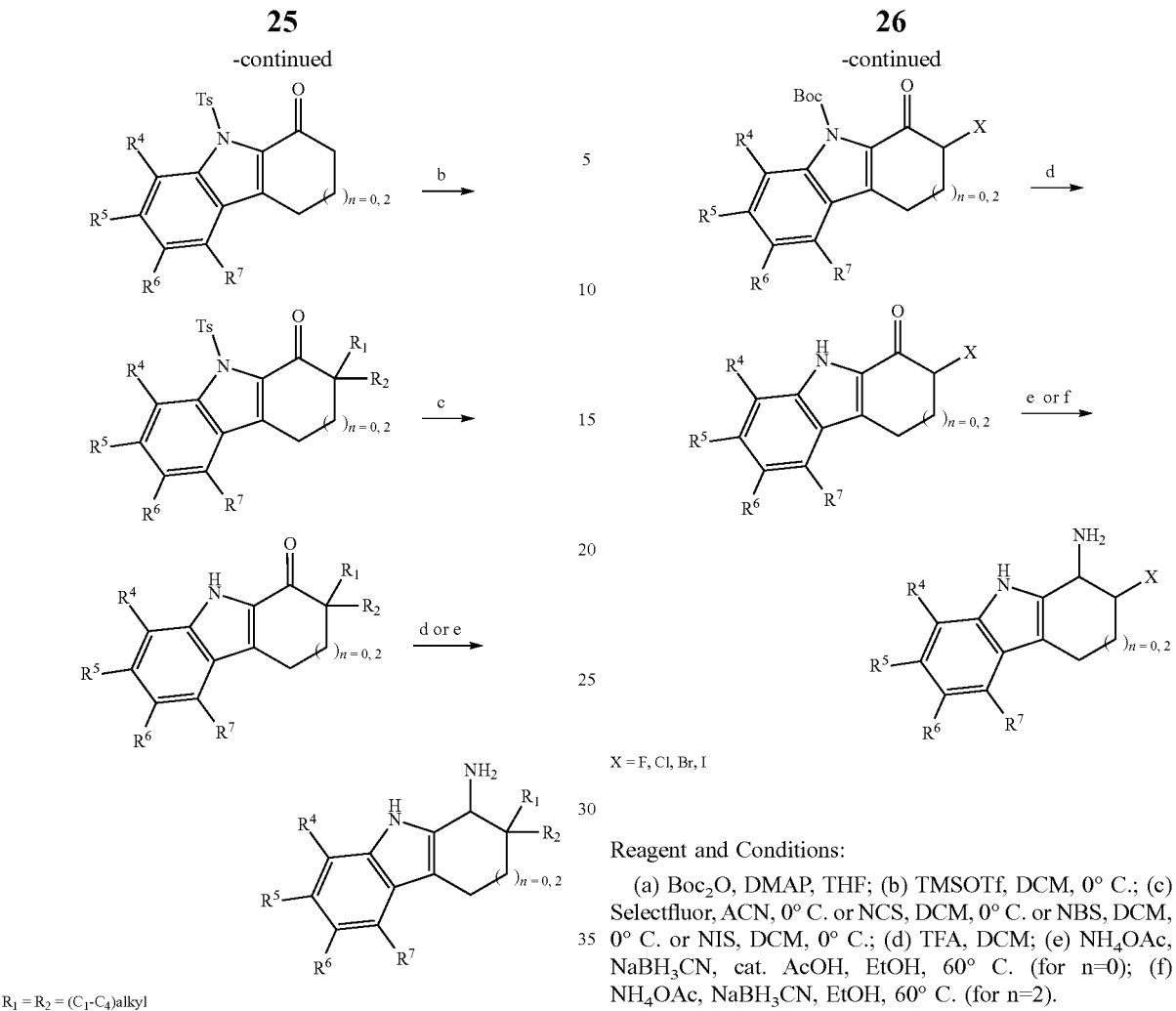
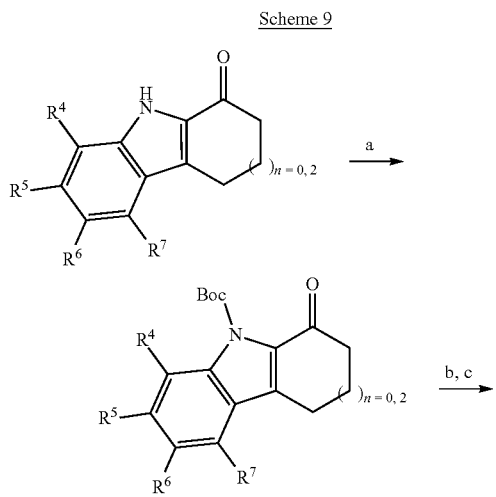
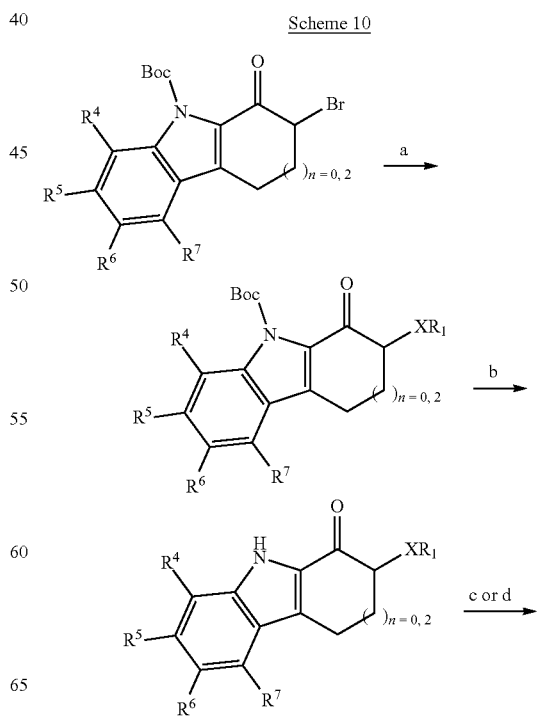

X = F, Cl, Br, I

Reagent and Conditions:

(a) Boc₂O, DMAP, THF; (b) TMSOTf, DCM, 0° C.; (c) Selectfluor, ACN, 0° C. or NCS, DCM, 0° C. or NBS, DCM, 0° C. or NIS, DCM, 0° C.; (d) TFA, DCM; (e) NH₄OAc, NaBH₃CN, cat. AcOH, EtOH, 60° C. (for n=0); (f) NH₄OAc, NaBH₃CN, EtOH, 60° C. (for n=2).

R₁ = R₂ = (C₁-C₄)alkyl

Reagent and Conditions:

(a) NaH, TsCl, THF; (b) LiHMDS, RX (X=OMs, Cl, Br, I), −78° C. to 0° C.; (c) NaOH, methanol, reflux; (d) NH₄OAc, NaBH₃CN, cat. AcOH, EtOH, 60° C. (for n=0); (e) NH₄OAc, NaBH₃CN, EtOH, 60° C. (for n=2).

Scheme 9

Scheme 10

27

-continued

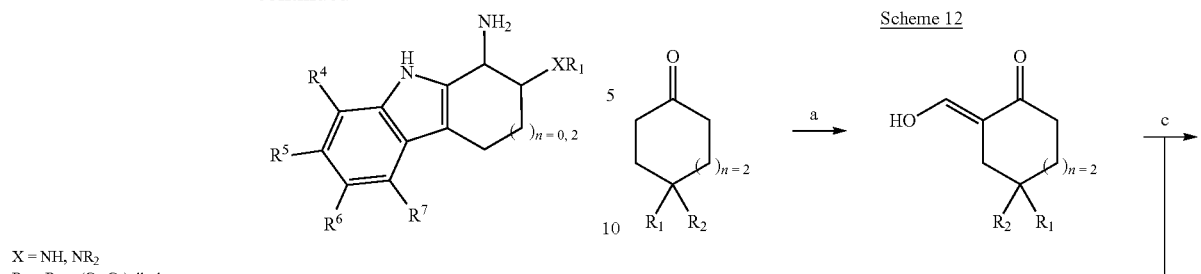

X = NH, NR$_2$
R$_1$ = R$_2$ = (C$_1$-C$_6$)alkyl

Reagent and Conditions:

(a) NaOR$_1$ or NaSR$_1$ or R$_1$NH$_2$ or R$_1$R$_2$NH, DMF; (b) TFA, DCM; (c) NH$_4$OAc, NaBH$_3$CN, cat. AcOH, EtOH, 60° C. (for n=0); (d) NH$_4$OAc, NaBH$_3$CN, EtOH, 60° C. (for n=2).

Scheme 11

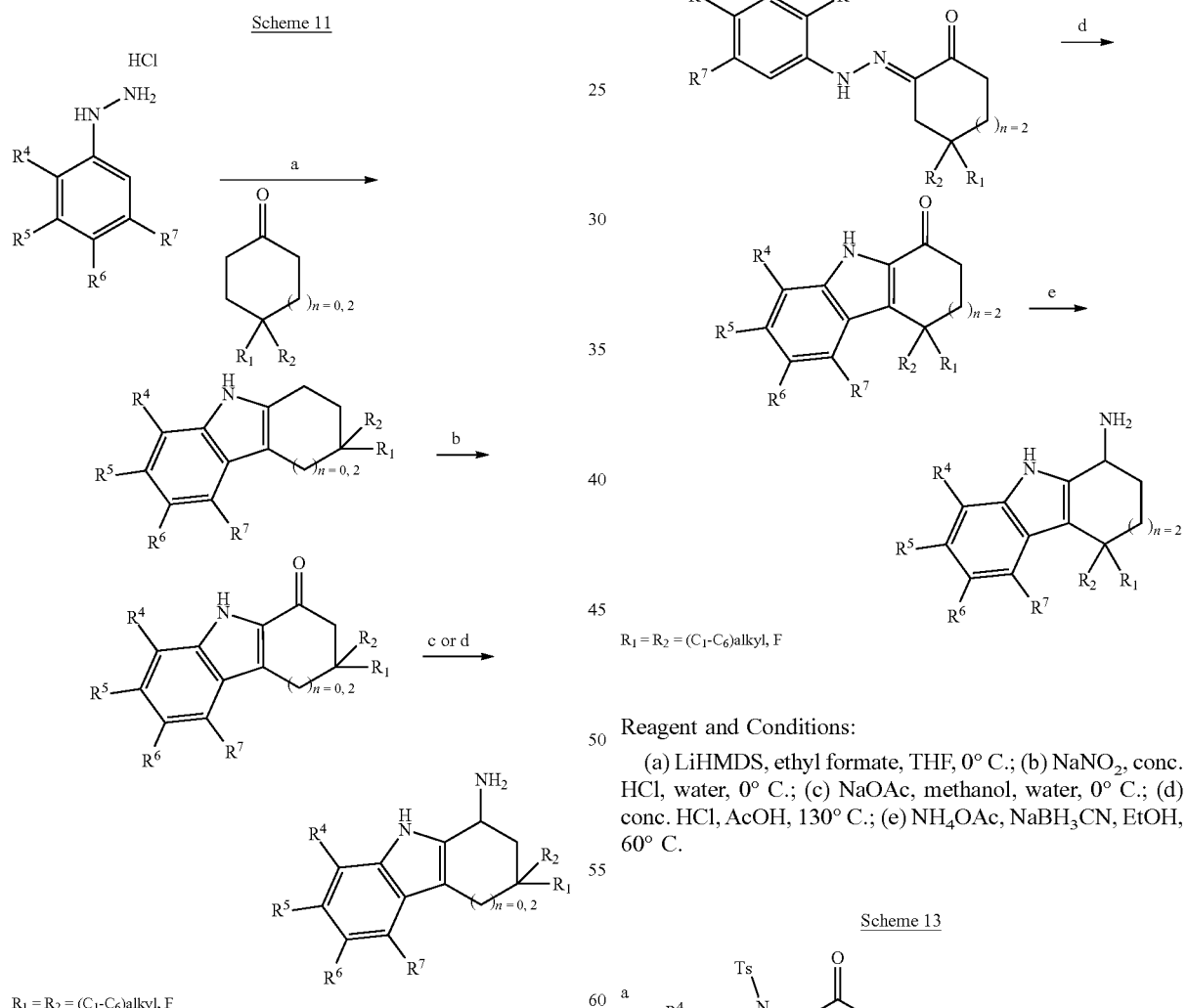

R$_1$ = R$_2$ = (C$_1$-C$_6$)alkyl, F

Reagent and Conditions:

(a) AcOH; (b) periodic acid, EtOH, water; (c) NH$_4$OAc, NaBH$_3$CN, cat. AcOH, EtOH, 60° C. (for n=0); (d) NH$_4$OAc, NaBH$_3$CN, EtOH, 60° C. (for n=2).

28

Scheme 12

R$_1$ = R$_2$ = (C$_1$-C$_6$)alkyl, F

Reagent and Conditions:

(a) LiHMDS, ethyl formate, THF, 0° C.; (b) NaNO$_2$, conc. HCl, water, 0° C.; (c) NaOAc, methanol, water, 0° C.; (d) conc. HCl, AcOH, 130° C.; (e) NH$_4$OAc, NaBH$_3$CN, EtOH, 60° C.

Scheme 13

-continued

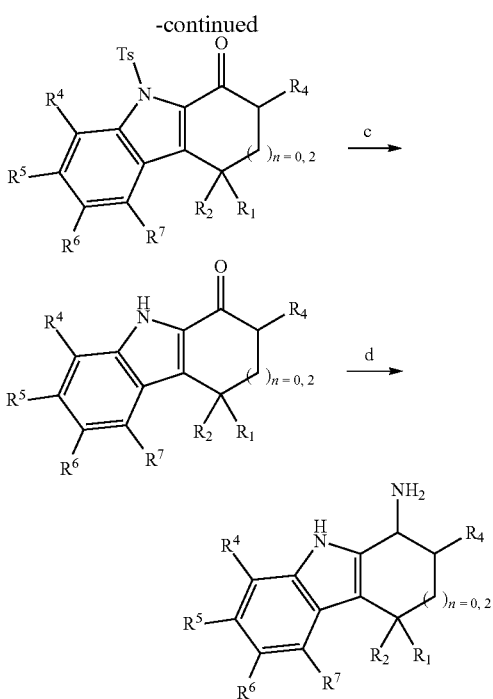

$R_1 = R_2 = R_4 = (C_1-C_6)alkyl$

Reagent and Conditions:
(a) NaH, TsCl, THF; (b) LiHMDS, RX (X=OMs, Cl, Br, I), −78° C. to 0° C.; (c) NaOH, methanol, reflux; (d) NH$_4$OAc, NaBH$_3$CN, EtOH, 60° C.

Bacterial Efflux Pump Inhibitors

In one embodiment, the bacterial efflux pump inhibitor is a compound of formula II:

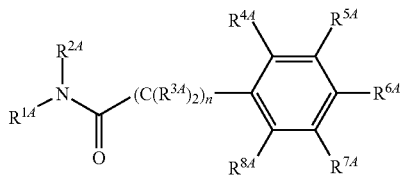

II or a pharmaceutically acceptable salt thereof, wherein:
$R^{1A}$ is $(C_3-C_8)$alkyl substituted with two or more groups selected from —NR$^{b1}$R$^{c1}$, —NHNH$_2$, —C(=NR$^{a1}$)(NR$^{b1}$R$^{c1}$), —NR$^{a1}$C(=NR$^{a1}$)(R$^{d1}$) and —NR$^{a1}$C(=NR$^{a1}$)(NR$^{b1}$R$^{c1}$);
$R^{2A}$ is hydrogen or $(C_1-C_3)$alkyl;
each $R^{3A}$ is independently hydrogen, halo or $(C_1-C_4)$alkyl;
$R^{4A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^{5A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^{6A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^{7A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
$R^{8A}$ is hydrogen, halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more groups independently selected from halo, $(C_1-C_4)$alkyl, $(C_1-C_4)$haloalkyl, $(C_1-C_4)$alkoxy and $(C_1-C_4)$haloalkoxy;
each $R^a$ is independently hydrogen or $(C_1-C_4)$alkyl;
each $R^{b1}$ and $R^{c1}$ is independently hydrogen or $(C_1-C_4)$alkyl;
$R^{d1}$ is $(C_1-C_3)$alkyl and
n is 0 or 1.

It is to be understood that the embodiments provided below are for compounds of formula II and all sub-formulas thereof (e.g., formulas IIa, IIb, IIc, IId, IIe, IIf, IIg). It is to be understood the two or more embodiments may be combined.

In one embodiment $R^{2A}$ is hydrogen.
In one embodiment $R^{3A}$ is hydrogen.
One embodiment provides a bacterial efflux pump inhibitor which is a compound of formula IIa:

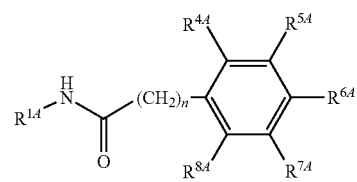

IIa or a pharmaceutically acceptable salt thereof.
In one embodiment $R^{8A}$ is hydrogen.
In one embodiment $R^{4A}$ is hydrogen, $(C_1-C_6)$haloalkyl or aryl wherein the aryl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.
In one embodiment $R^{4A}$ is hydrogen, —CF$_3$ or phenyl.
In one embodiment $R^{4A}$ is hydrogen.
One embodiment provides a bacterial efflux pump inhibitor which is a compound of formula Ib:

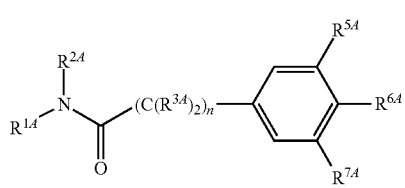

IIb or a pharmaceutically acceptable salt thereof.
In one embodiment $R^{7A}$ is hydrogen.

One embodiment provides a bacterial efflux pump inhibitor which is a compound of formula IIc:

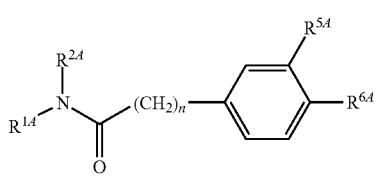

IIc or a pharmaceutically acceptable salt thereof.

In one embodiment $R^{5A}$ is halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy;

In one embodiment $R^{5A}$ is $(C_1-C_6)$haloalkyl.

In one embodiment $R^{5A}$ is —$CF_3$.

In one embodiment $R^{6A}$ is halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy; In one embodiment $R^{6A}$ is $(C_1-C_6)$haloalkyl.

In one embodiment $R^{6A}$ is —$CF_3$.

In one embodiment $R^{6A}$ is hydrogen.

One embodiment provides a bacterial efflux pump inhibitor which is a compound formula IId:

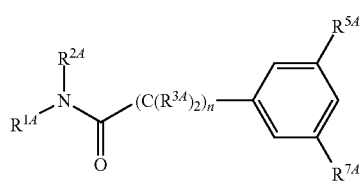

IId or a pharmaceutically acceptable salt thereof.

One embodiment provides a bacterial efflux pump inhibitor which is a compound of formula IIe:

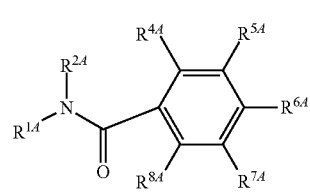

IIe or a pharmaceutically acceptable salt thereof.

One embodiment provides a bacterial efflux pump inhibitor which is a compound of formula IIf:

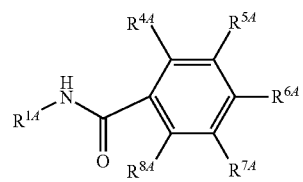

IIf or a pharmaceutically acceptable salt thereof.

One embodiment provides a bacterial efflux pump inhibitor which is a compound of formula IIg:

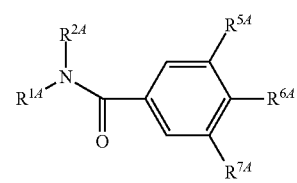

IIg or a pharmaceutically acceptable salt thereof.

In one embodiment $R^{5A}$ is halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^{5A}$ is $(C_1-C_6)$alkyl, $(C_1-C_6)$haloalkyl, or aryl wherein the aryl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^{5A}$ is $(C_1-C_6)$alkyl, $(C_1-C_6)$haloalkyl, or phenyl wherein phenyl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^{5A}$ is tert-butyl, —$CF_3$, phenyl or 4-fluorophenyl.

In one embodiment $R^{7A}$ is halo, $(C_1-C_6)$alkyl, $(C_1-C_6)$haloalkyl, $(C_1-C_6)$alkoxy, $(C_1-C_4)$haloalkoxy, aryl or heteroaryl wherein the aryl or heteroaryl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^{7A}$ is $(C_1-C_6)$alkyl, $(C_1-C_6)$haloalkyl or aryl wherein the aryl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^{7A}$ is $(C_1-C_6)$alkyl, $(C_1-C_6)$haloalkyl, or phenyl wherein phenyl is optionally substituted with one or more (e.g., 1, 2, 3, 4 or 5) groups independently selected from halo, $(C_1-C_4)$alkyl, $(C_1-C_4)$haloalkyl, $(C_1-C_4)$alkoxy and $(C_1-C_4)$haloalkoxy.

In one embodiment $R^{7A}$ is tert-butyl, —$CF_3$, phenyl or 4-fluorophenyl.

In one embodiment the moiety:

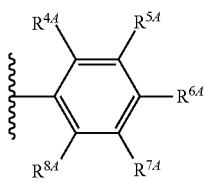

of the compound of formula II is:

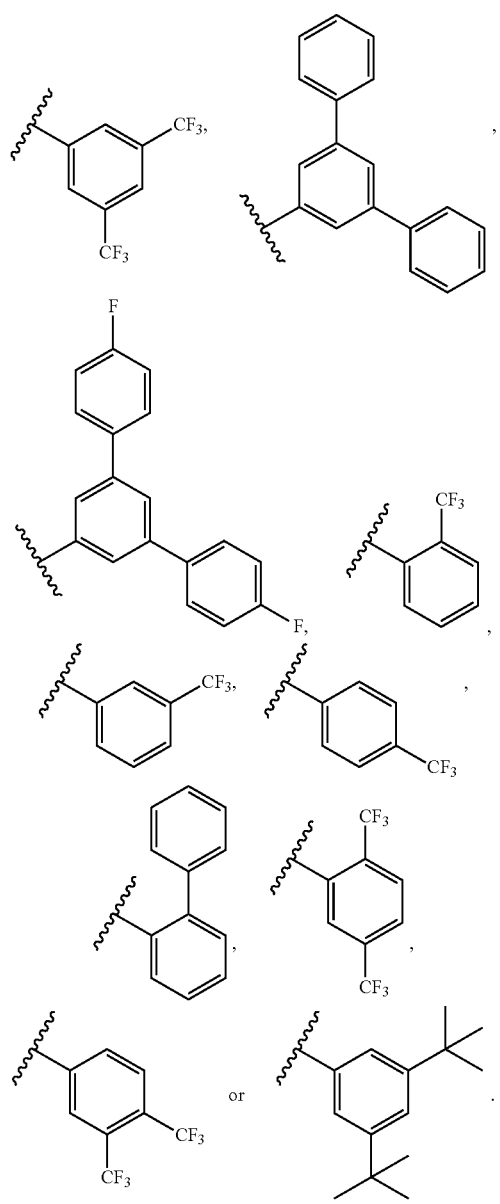

In one embodiment $R^{14}$ is (C$_3$-C$_8$)alkyl substituted with two or more groups independently selected from —NR$^{b1}$R$^{c1}$.

In one embodiment $R^{14}$ is (C$_3$-C$_8$)alkyl substituted with two groups independently selected from —NR$^{b1}$R$^{c1}$.

In one embodiment $R^{14}$ is (C$_4$-C$_5$)alkyl substituted with two groups independently selected from —NR$^{b1}$R$^{c1}$.

In one embodiment $R^{b1}$ and $R^{c1}$ are each hydrogen.
In one embodiment $R^{1A}$ is:

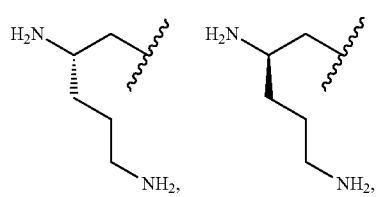

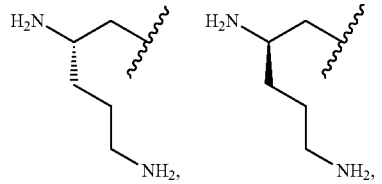

In one embodiment $R^{1A}$ is:

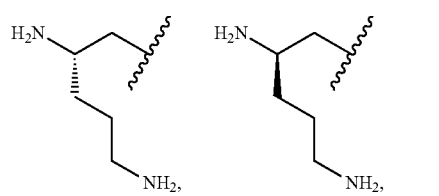

In one embodiment n is 0.
In one embodiment, the bacterial efflux pump inhibitor is a compound of formula III:

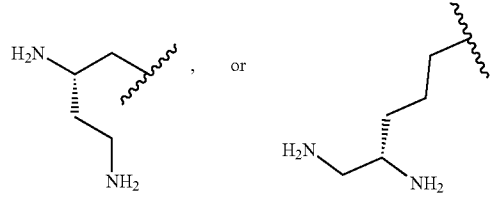

III or a pharmaceutically acceptable salt thereof, wherein:
A is —C(=O)N(R$^{a1}$)—R$^{B1}$, —(C$_1$-C$_3$)alkyl-C(=O)N(R$^{a1}$)R$^{1B}$, —(C$_1$-C$_3$)alkyl-O—R$^{1B}$, —O—R$^{1B}$, —(C$_1$-C$_3$)alkyl-N(R$^{a1}$)—R$^{1B}$, or —N(R$^{a1}$)—R$^{1B}$;
each R$^{1B}$ is independently a (C$_3$-C$_7$)carbocyclyl, (C$_3$-C$_7$)carbocyclyl-(C$_1$-C$_4$)alkyl-, 4-7 membered monocyclic heterocyclyl, or 4-7 membered monocyclic heterocyclyl-(C$_1$-C$_4$)alkyl-, wherein each (C$_3$-C$_7$)carbocyclyl or ($C_3$-$C_7$)carbocyclyl-($C_1$-$C_4$)alkyl- is independently substituted with one or more groups selected from the group consisting of Z and —($C_1$-$C_6$)alkyl substituted with one or more Z, and wherein each 4-7 membered monocyclic heterocyclyl or 4-7 membered monocyclic heterocyclyl-($C_1$-$C_4$)alkyl- is independently optionally substituted with one or more groups selected from the group consisting of Z and —($C_1$-$C_6$)alkyl substituted with one or more Z, wherein each Z is independently selected from the group consisting of $NR^{b2}R^{c2}$, —$NHNH_2$, —$C(=NR^{a2})(NR^{b2}R^{c2})$, —$NR^{a2}C(=NR^{a2})(R^{d2})$, and —$NR^{a2}C(=NR^{a2})(NR^{b2}R^{c2})$ and wherein each ($C_3$-$C_7$)carbocyclyl, ($C_3$-$C_7$)carbocyclyl-($C_1$-$C_4$)alkyl-, 4-7 membered monocyclic heterocyclyl, or 4-7 membered monocyclic heterocyclyl-($C_1$-$C_4$)alkyl-, is independently optionally substituted independently with one or more ($C_1$-$C_4$)alkyl;

$R^{2B}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_4$)alkyl, ($C_1$-$C_4$)haloalkyl, ($C_1$-$C_4$)alkoxy and ($C_1$-$C_4$)haloalkoxy;

$R^{3B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy;

$R^{4B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy;

$R^{5B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy;

$R^{6B}$ is hydrogen, halo, ($C_1$-$C_4$)alkyl, ($C_1$-$C_4$)haloalkyl, ($C_1$-$C_4$)alkoxy, ($C_1$-$C_4$)haloalkoxy, aryl or heteroaryl wherein the aryl or heteroaryl is optionally substituted with one or more groups independently selected from halo, —$NO_2$, —CN, ($C_1$-$C_4$)alkyl, ($C_1$-$C_4$)haloalkyl, ($C_1$-$C_4$)alkoxy and $C_1$-$C_4$)haloalkoxy;

each $R^{a1}$ is independently hydrogen, ($C_1$-$C_6$)alkyl or ($C_3$-$C_7$)carbocyclyl;

each $R^{a2}$ is independently hydrogen, ($C_1$-$C_6$)alkyl or ($C_3$-$C_7$)carbocyclyl;

each $R^{b2}$ and $R^{c2}$ is independently hydrogen, ($C_1$-$C_6$)alkyl or ($C_3$-$C_7$)carbocyclyl; and $R^2$ is ($C_1$-$C_6$)alkyl or ($C_3$-$C_7$)carbocyclyl.

It is to understood that the embodiments provided below are for compounds of formula III and all sub-formulas thereof. It is to be understood the two or more embodiments may be combined.

In one embodiment A is —$C(=O)N(R^{a1})$—$R^{1B}$, —($C_1$-$C_3$)alkyl-$C(=O)N(R^{a1})R^{1B}$, —($C_1$-$C_3$)alkyl-O—$R^{1B}$, or —O—$R^{1B}$.

In one embodiment A is —$C(=O)N(R^{a1})$—$R^{1B}$.

In one embodiment A is —($C_1$-$C_3$)alkyl-$C(=O)N(R^{a1})R^{1B}$.

In one embodiment $R^{a1}$ is hydrogen.

In one embodiment A is —O—$R^{1B}$.

In one embodiment $R^{2B}$ is hydrogen, halo, ($C_1$-$C_4$)alkyl, ($C_1$-$C_4$)haloalkyl, ($C_1$-$C_4$)alkoxy, or ($C_1$-$C_4$)haloalkoxy.

In one embodiment $R^{2B}$ is hydrogen.

In one embodiment $R^{3B}$ is aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy.

In one embodiment $R^{3B}$ is phenyl wherein the phenyl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy.

In one embodiment $R^{3B}$ is 4-fluorophenyl.

In one embodiment $R^{4B}$ is hydrogen, halo, ($C_1$-$C_6$)alkyl, ($C_1$-$C_4$)haloalkyl, ($C_1$-$C_6$)alkoxy, ($C_1$-$C_4$)haloalkoxy.

In one embodiment $R^{4B}$ is hydrogen.

In one embodiment $R^{5B}$ is aryl or heteroaryl wherein the aryl or heteroaryl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy.

In one embodiment $R^{5B}$ is phenyl wherein the phenyl is optionally substituted with one or more groups independently selected from halo, —$NO_2$, —CN, ($C_1$-$C_6$)alkyl, ($C_1$-$C_4$)haloalkyl, ($C_1$-$C_6$)alkoxy and ($C_1$-$C_4$)haloalkoxy.

In one embodiment $R^{5B}$ is 4-fluorophenyl.

In one embodiment $R^{6B}$ is hydrogen, halo, ($C_1$-$C_4$)alkyl, ($C_1$-$C_4$)haloalkyl, ($C_1$-$C_4$)alkoxy, or ($C_1$-$C_4$)haloalkoxy.

In one embodiment $R^{6B}$ is hydrogen.

In one embodiment the moiety:

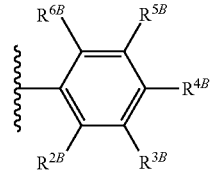

of the compound of formula III is:

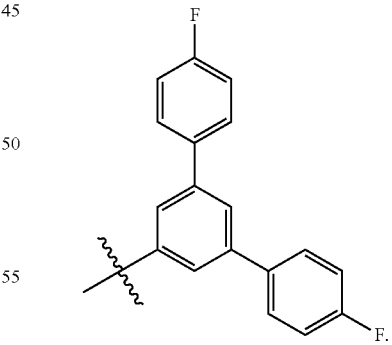

In one embodiment $R^{1B}$ is a 4-7 membered monocyclic heterocyclyl or 4-7 membered monocyclic heterocyclyl-($C_1$-$C_4$)alkyl-, wherein the 4-7 membered monocyclic heterocyclyl or 4-7 membered monocyclic heterocyclyl-($C_1$-$C_4$)alkyl- is optionally substituted independently with one or more groups selected from the group consisting of Z and —($C_1$-$C_6$)alkyl substituted with one or more Z, wherein each Z is $NR^{b2}R^{c2}$ and wherein the 4-7 membered monocyclic heterocyclyl or 4-7 membered monocyclic heterocyclyl-($C_1$-$C_4$)alkyl- is optionally substituted with one or more ($C_1$-$C_4$)alkyl.

In one embodiment $R^{1B}$ is a 4-7 membered monocyclic N-heterocyclyl or 4-7 membered monocyclic N-heterocyclyl-($C_1$-$C_4$)alkyl-, wherein the 4-7 membered monocyclic N-heterocyclyl or 4-7 membered monocyclic N-heterocyclyl-($C_1$-$C_4$)alkyl- is optionally substituted independently with one or more groups selected from the group consisting of Z and —($C_1$-$C_6$)alkyl substituted with one or more Z, wherein each Z is $NR^{b2}R^{c2}$ and wherein the 4-7 membered monocyclic N-heterocyclyl or 4-7 membered monocyclic N-heterocyclyl-($C_1$-$C_4$)alkyl- is optionally substituted with one or more ($C_1$-$C_4$)alkyl.

In one embodiment $R^{1B}$ is a pyrrolidinyl or pyrrolidinyl-($C_1$-$C_4$)alkyl-, wherein the pyrrolidinyl or pyrrolidinyl-($C_1$-$C_4$)alkyl- is optionally substituted independently with one or more groups selected from the group consisting of Z and —($C_1$-$C_6$)alkyl substituted with one or more Z, wherein each Z is $NR^{b2}R^{c2}$ and wherein the pyrrolidinyl or pyrrolidinyl-($C_1$-$C_4$)alkyl- is optionally substituted with one or more ($C_1$-$C_4$)alkyl.

In one embodiment $R^{1B}$ is a pyrrolidinyl or pyrrolidinyl-($CH_2$)—, wherein the pyrrolidinyl-($CH_2$)— is optionally substituted independently with one or more groups selected from the group consisting of Z and —($C_1$-$C_6$)alkyl substituted with one or more Z, wherein each Z is $NR^{b2}R^{c2}$ and wherein the pyrrolidinyl or pyrrolidinyl-($C_1$-$C_4$)alkyl- is optionally substituted with one or more ($C_1$-$C_4$)alkyl.

In one embodiment $R^{1B}$ is a pyrrolidinyl or pyrrolidinyl-($CH_2$)—, wherein the pyrrolidinyl-($CH_2$)— is optionally substituted independently with one or more groups selected from the group consisting of Z and —($C_1$-$C_4$)alkyl substituted with one or more Z, wherein each Z is $NR^{b2}R^{c2}$.

In one embodiment each $R^{b2}$ and $R^{c2}$ is hydrogen
In one embodiment $R^{1B}$ is:

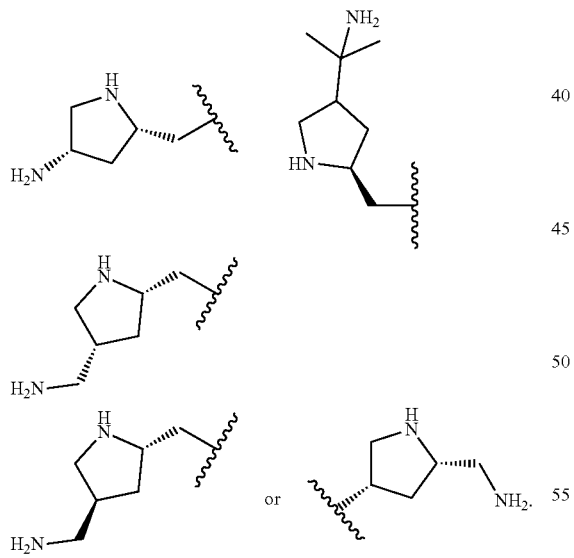

In one embodiment A is:

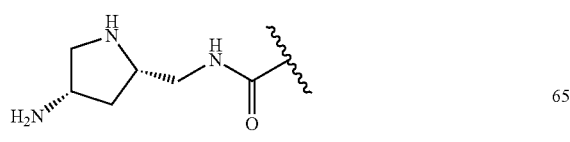

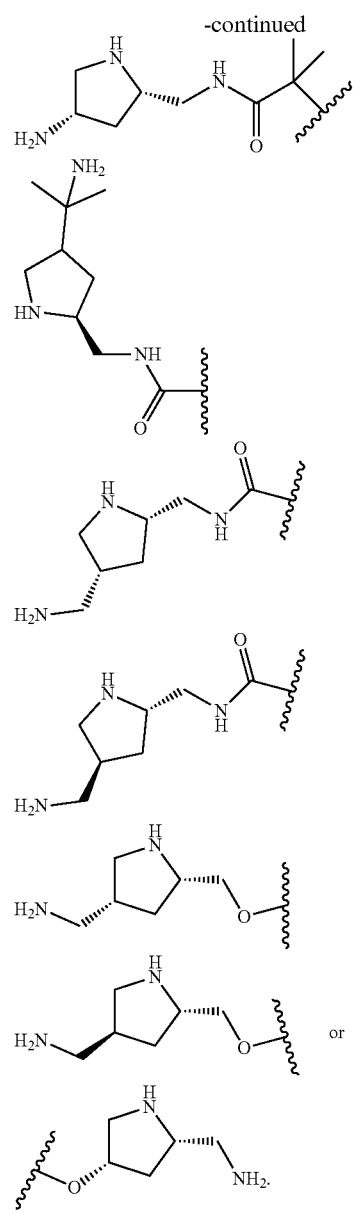

In one embodiment, the bacterial efflux pump inhibitor is a compound of formula IV:

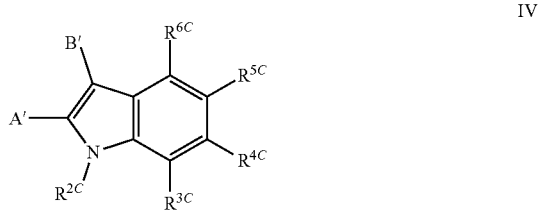

IV or a pharmaceutically acceptable salt thereof, wherein:
one of A' or B' is —C(=O)N($R^{a1}$)—$R^{1C}$, ($C_1$-$C_3$)alkyl-C(=O)N($R^{a1}$)$R^{1C}$, —($C_1$-$C_3$)alkyl-O—$R^{1C}$, —O—$R^{1C}$, —($C_1$-$C_3$)alkyl-N($R^{a1}$)—$R^{1C}$, —N($R^{a1}$)—$R^{1C}$, or $R^{1C}$ and the other of A' or B' is H, halogen, or ($C_1$-$C_4$)alkyl;

each $R^{1C}$ is independently:
(a) $(C_1\text{-}C_{14})$alkyl substituted with one or more groups selected from the group consisting of —$NR^{b2}R^{c2}$, —$NHNH_2$, —$C(=NR^{a2})(NR^{b2}R^{c2})$, —$NR^{a2}C(=NR^{a2})(R^2)$, and —$NR^{a2}C(=NR^{a2})(NR^{b2}R^{c2})$; and wherein $(C_1\text{-}C_{14})$alkyl is optionally substituted independently with one or more halo, $(C_1\text{-}C_4)$alkyl or $(C_3\text{-}C_7)$carbocyclyl; or
(b) $(C_3\text{-}C_7)$carbocyclyl, $(C_3\text{-}C_7)$carbocyclyl-$(C_1\text{-}C_4)$alkyl-, 4-7 membered monocyclic heterocyclyl, or 4-7 membered monocyclic heterocyclyl-$(C_1\text{-}C_4)$alkyl-, wherein each $(C_3\text{-}C_7)$carbocyclyl or $(C_3\text{-}C_7)$carbocyclyl-$(C_1\text{-}C_4)$alkyl- is independently substituted with one or more $Z^1$ or $Z^2$, and wherein each 4-7 membered monocyclic heterocyclyl or 4-7 membered monocyclic heterocyclyl-$(C_1\text{-}C_4)$alkyl- is independently optionally substituted with one or more $Z^1$ or $Z^2$, and wherein any $(C_3\text{-}C_7)$carbocyclyl, $(C_3\text{-}C_7)$carbocyclyl-$(C_1\text{-}C_4)$alkyl-, 4-7 membered monocyclic heterocyclyl, or 4-7 membered monocyclic heterocyclyl-$(C_1\text{-}C_4)$alkyl- of $R^1$ is independently optionally substituted independently with one or more halo, $(C_1\text{-}C_4)$alkyl or $(C_3\text{-}C_7)$carbocyclyl;

$R^{2C}$ is hydrogen, $(C_1\text{-}C_4)$alkyl or phenyl$(C_1\text{-}C_3)$alkyl-, wherein the phenyl is optionally substituted with one or more $(C_1\text{-}C_4)$alkyl, —$O(C_1\text{-}C_4)$alkyl, halogen, or —$NO_2$;

$R^{3C}$ is hydrogen, halo, $(C_1\text{-}C_4)$alkyl, $(C_1\text{-}C_4)$haloalkyl, $(C_1\text{-}C_4)$alkoxy, $(C_1\text{-}C_4)$haloalkoxy, aryl, or heteroaryl wherein the aryl or heteroaryl is optionally substituted with one or more groups independently selected from the group consisting of halo, —OH, —$NO_2$, —CN, $(C_1\text{-}C_4)$alkyl, $(C_1\text{-}C_4)$haloalkyl, $(C_1\text{-}C_4)$alkoxy, and $(C_1\text{-}C_4)$haloalkoxy;

$R^{4C}$ is hydrogen, halo, $(C_1\text{-}C_4)$alkyl, $(C_1\text{-}C_4)$haloalkyl, $(C_1\text{-}C_4)$alkoxy, $(C_1\text{-}C_4)$haloalkoxy, aryl, or heteroaryl wherein the aryl or heteroaryl is optionally substituted with one or more groups independently selected from the group consisting of halo, —OH, —$NO_2$, —CN, $(C_1\text{-}C_4)$alkyl, $(C_1\text{-}C_4)$haloalkyl, $(C_1\text{-}C_4)$alkoxy, and $(C_1\text{-}C_4)$haloalkoxy;

$R^{5C}$ is hydrogen, halo, $(C_1\text{-}C_4)$alkyl, $(C_1\text{-}C_4)$haloalkyl, $(C_1\text{-}C_4)$alkoxy, $(C_1\text{-}C_4)$haloalkoxy, aryl, or heteroaryl wherein the aryl or heteroaryl is optionally substituted with one or more groups independently selected from the group consisting of halo, —OH, —$NO_2$, —CN, $(C_1\text{-}C_4)$alkyl, $(C_1\text{-}C_4)$haloalkyl, $(C_1\text{-}C_4)$alkoxy, and $(C_1\text{-}C_4)$haloalkoxy;

$R^{6C}$ is hydrogen, halo, $(C_1\text{-}C_4)$alkyl, $(C_1\text{-}C_4)$haloalkyl, $(C_1\text{-}C_4)$alkoxy, $(C_1\text{-}C_4)$haloalkoxy, aryl, or heteroaryl wherein the aryl or heteroaryl is optionally substituted with one or more groups independently selected from the group consisting of halo, —OH, —$NO_2$, —CN, $(C_1\text{-}C_4)$alkyl, $(C_1\text{-}C_4)$haloalkyl, $(C_1\text{-}C_4)$alkoxy, and $(C_1\text{-}C_4)$haloalkoxy;

each $Z^1$ is independently selected from the group consisting of —$NR^{b3}R^{c3}$, —$NHNH_2$, —$C(=NR^{a3})(NR^{b3}R^{c3})$, —$NR^{a3}C(=NR^{a3})(R^{d3})$, and —$NR^{a3}C(=NR^{a3})(NR^{b3}R^{c3})$;

each $Z^2$ is independently —$(C_1\text{-}C_6)$alkyl substituted with one or more $Z^1$ and optionally substituted with one or more $Z^3$;

each $Z^3$ is independently halo or $(C_3\text{-}C_7)$carbocyclyl;

each $R^a$ is independently hydrogen, $(C_1\text{-}C_4)$alkyl or $(C_3\text{-}C_7)$carbocyclyl;

each $R^{a2}$ is independently hydrogen, $(C_1\text{-}C_4)$alkyl or $(C_3\text{-}C_7)$carbocyclyl;

each $R^{b2}$ and $R^{c2}$ is independently hydrogen, $(C_1\text{-}C_4)$alkyl or $(C_3\text{-}C_7)$carbocyclyl;

$R^{d2}$ is $(C_1\text{-}C_4)$alkyl or $(C_3\text{-}C_7)$carbocyclyl;

each $R^{a3}$ is independently hydrogen $(C_1\text{-}C_4)$alkyl or $(C_3\text{-}C_7)$carbocyclyl;

each $R^{b3}$ and $R^{c3}$ is independently hydrogen $(C_1\text{-}C_4)$alkyl or $(C_3\text{-}C_7)$carbocyclyl; and $R^{d3}$ is $(C_1\text{-}C_4)$alkyl or $(C_3\text{-}C_7)$carbocyclyl.

It is to be understood that the embodiments provided below are for compounds of formula IV and all sub-formulas thereof (e.g., formulas IVa, IVb). It is to be understood the two or more embodiments may be combined.

In one embodiment one of A' or B' is —$C(=O)N(R^{a1})$—$R^{1C}$ or —$(C_1\text{-}C_3)$alkyl-$C(=O)N(R^{a1})R^{1C}$, and the other of A' or B' is H, halogen, or $(C_1\text{-}C_6)$alkyl.

In one embodiment one of A' or B' is —$C(=O)N(R^a)$—$R^{1C}$, and the other of A' or B' is H, halogen, or $(C_1\text{-}C_6)$alkyl.

In one embodiment A' is —$C(=O)N(R^{a1})$—$R^{1C}$, and B' is H.

In one embodiment B' is —$C(=O)N(R^{a1})$—$R^{1C}$, and A' is H.

In one embodiment one of A' or B' is —$C(=O)N(R^{a1})$—$R^{1C}$ or —$(C_1\text{-}C_3)$alkyl-$C(=O)N(R^{a1})R^{1C}$, and the other of A' or B' is H.

In one embodiment one of A' or B' is —$C(=O)N(R^a)$—$R^{1C}$, and the other of A' or B' is H.

In one embodiment $R^{2C}$ is hydrogen, $(C_1\text{-}C_4)$alkyl or benzyl, wherein benzyl is optionally substituted with one or more $(C_1\text{-}C_4)$alkyl, —$O(C_1\text{-}C_4)$alkyl, halogen or —$NO_2$.

In one embodiment $R^{a1}$ is hydrogen.

In one embodiment $R^{2C}$ is hydrogen or $(C_1\text{-}C_4)$alkyl.

In one embodiment $R^{2C}$ is hydrogen.

In one embodiment $R^{2C}$ is hydrogen, methyl, or 4-fluorobenzyl.

In one embodiment a compound of formula IV is a compound formula IVa or IVb:

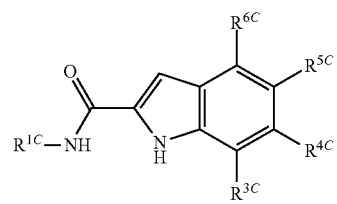

IVa

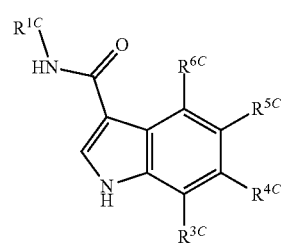

IVb or a pharmaceutically acceptable salt thereof.

In one embodiment $R^{3C}$ is hydrogen or aryl wherein the aryl is optionally substituted with one or more groups independently selected from the group consisting of halo, —OH, —$NO_2$, —CN, $(C_1\text{-}C_4)$alkyl, $(C_1\text{-}C_4)$haloalkyl, $(C_1\text{-}C_4)$alkoxy and $(C_1\text{-}C_4)$haloalkoxy.

In one embodiment $R^{3C}$ is hydrogen or phenyl wherein the phenyl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment R$^{3C}$ is hydrogen or 4-fluorophenyl.

In one embodiment R$^{4C}$ is hydrogen, aryl, or heteroaryl wherein the aryl or heteroaryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy.

In one embodiment R$^{4C}$ is hydrogen, phenyl, or pyridinyl wherein the phenyl or pyridinyl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy.

In one embodiment R$^{4C}$ is hydrogen, 4-nitrophenyl, 4-fluorophenyl, 3,4-difluorophenyl, 4-t-butylphenyl, 4-methoxyphenyl, pyridin-4-yl, 4-hydroxyphenyl, 4-chlorophenyl, or 4-cyanophenyl.

In one embodiment R$^{5C}$ is hydrogen or aryl wherein the aryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment R$^{5C}$ is hydrogen or phenyl wherein the phenyl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment R$^{5C}$ is hydrogen or 4-fluorophenyl.

In one embodiment R$^{6C}$ is hydrogen or aryl wherein the aryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment R$^{6C}$ is hydrogen or phenyl wherein the phenyl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy and (C$_1$-C$_4$)haloalkoxy.

In one embodiment R$^{6C}$ is hydrogen or 4-fluorophenyl.

In one embodiment R$^{1C}$ is (C$_1$-C$_{14}$)alkyl substituted with one or more groups independently selected from —NR$^{b2}$R$^{c2}$.

In one embodiment R$^{1C}$ is (C$_2$-C$_{10}$)alkyl substituted with one or more groups independently selected from —NR$^{b2}$R$^{c2}$.

In one embodiment R$^{1C}$ is (C$_1$-C$_{14}$)alkyl substituted with one or more groups independently selected from —NR$^{b2}$R$^{c2}$.

In one embodiment R$^{1C}$ is (C$_2$-C$_8$)alkyl substituted with two or more groups independently selected from —NR$^{b2}$R$^{c2}$.

In one embodiment R$^{1C}$ is (C$_4$-C$_8$)alkyl substituted with two or more groups independently selected from —NR$^{b2}$R$^{c2}$.

In one embodiment R$^{b2}$ and R$^{c2}$ are each hydrogen.

In one embodiment R$^{1C}$ is a 4-7 membered monocyclic heterocyclyl-(C$_1$-C$_4$)alkyl-, wherein the 4-7 membered monocyclic heterocyclyl-(C$_1$-C$_4$)alkyl- is substituted with one or more groups independently selected from the group consisting of Z and —(C$_1$-C$_6$)alkyl substituted with one or more Z, wherein each Z is independently selected from the group consisting of —NR$^{b3}$R$^{c3}$, —NHNH$_2$, —C(=NR$^{a3}$)(NR$^{b3}$R$^{c3}$), —NR$^{a3}$C(=NR$^{a3}$)(R$^{d3}$), and —NR$^{a3}$C(=NR$^{a3}$)(NR$^{b3}$R$^{c3}$) and wherein the 4-7 membered monocyclic heterocyclyl-(C$_1$-C$_4$)alkyl- is optionally substituted with one or more (C$_1$-C$_6$)alkyl.

In one embodiment R$^{1C}$ is a 4-7 membered monocyclic heterocyclyl-(C$_1$-C$_4$)alkyl-, wherein the 4-7 membered monocyclic heterocyclyl-(C$_1$-C$_4$)alkyl- is substituted with one or more groups independently selected from the group consisting of Z and (C$_1$-C$_6$)alkyl substituted with one or more Z, wherein each Z is independently —NR$^{b3}$R$^{c3}$ and wherein the 4-7 membered monocyclic heterocyclyl-(C$_1$-C$_4$)alkyl- is optionally substituted with one or more (C$_1$-C$_6$) alkyl.

In one embodiment R$^{1C}$ is pyrrolidinyl-(C$_1$-C$_4$)alkyl-, wherein the pyrrolidinyl-(C$_1$-C$_4$)alkyl- is substituted with one or more groups independently selected from the group consisting of Z and —(C$_1$-C$_6$)alkyl substituted with one or more Z, wherein each Z is independently —NR$^{b3}$R$^{c3}$ and wherein is pyrrolidinyl-(C$_1$-C$_4$)alkyl- is optionally substituted independently with one or more (C$_1$-C$_6$)alkyl In one embodiment R$^{1C}$ is pyrrolidinyl-(CH$_2$)—, wherein the pyrrolidinyl-(CH$_2$)— is substituted with one or more groups independently selected from the group consisting of Z and —(C$_1$-C$_6$)alkyl substituted with one or more Z, wherein each Z is independently —NR$^{b3}$R$^{c3}$ and wherein the pyrrolidinyl-(CH$_2$)— is optionally substituted independently with one or more (C$_1$-C$_6$)alkyl.

In one embodiment R$^{1C}$ is pyrrolidinyl-(CH$_2$)—, wherein the pyrrolidinyl-(CH$_2$)— is substituted on the pyrrolidinyl with an —(C$_1$-C$_6$)alkyl substituted with one or more —NR$^{b3}$R$^{c3}$.

In one embodiment R$^{b3}$ and R$^{c3}$ are each hydrogen.

In one embodiment R$^{1C}$ is:

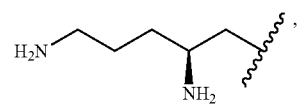

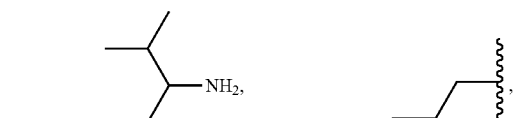

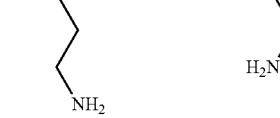

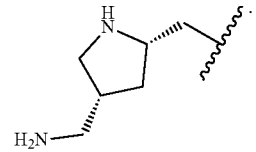

In one embodiment one of A' or B' is:

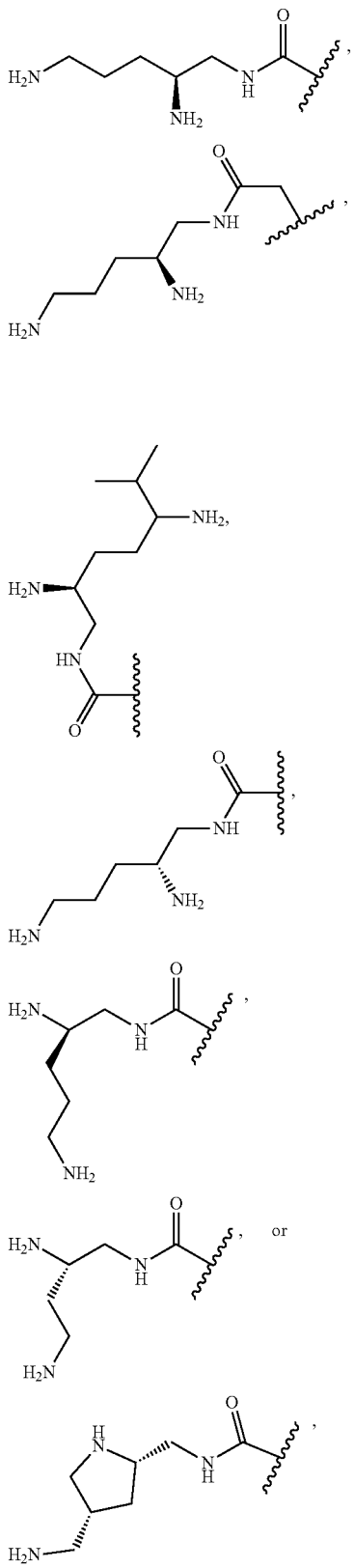

and the other of A' or B' is H.

In one embodiment, the bacterial efflux pump inhibitor is a compound of formula V:

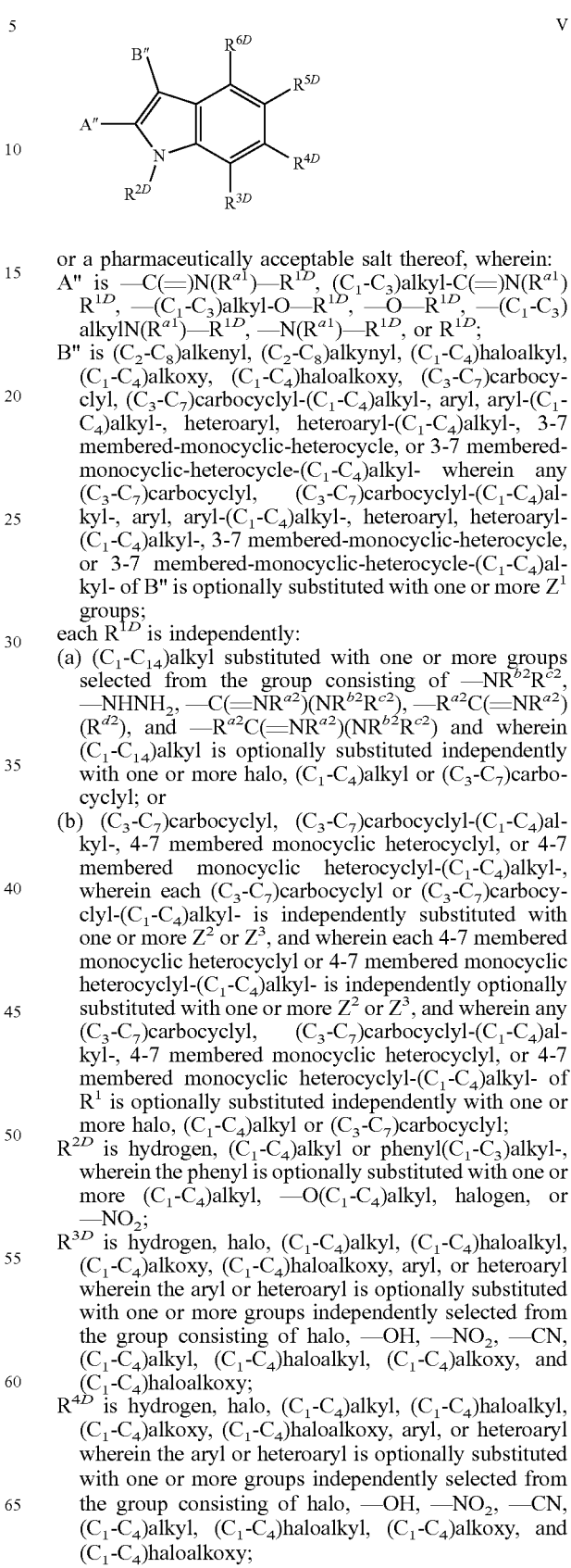

or a pharmaceutically acceptable salt thereof, wherein:
A" is —C(=)N(R$^{a1}$)—R$^{1D}$, (C$_1$-C$_3$)alkyl-C(=)N(R$^{a1}$)R$^{1D}$, —(C$_1$-C$_3$)alkyl-O—R$^{1D}$, —O—R$^{1D}$, —(C$_1$-C$_3$)alkylN(R$^{a1}$)—R$^{1D}$, —N(R$^{a1}$)—R$^{1D}$, or R$^{1D}$;

B" is (C$_2$-C$_8$)alkenyl, (C$_2$-C$_8$)alkynyl, (C$_1$-C$_4$)haloalkyl, (C$_1$-C$_4$)alkoxy, (C$_1$-C$_4$)haloalkoxy, (C$_3$-C$_7$)carbocyclyl, (C$_3$-C$_7$)carbocyclyl-(C$_1$-C$_4$)alkyl-, aryl, aryl-(C$_1$-C$_4$)alkyl-, heteroaryl, heteroaryl-(C$_1$-C$_4$)alkyl-, 3-7 membered-monocyclic-heterocycle, or 3-7 membered-monocyclic-heterocycle-(C$_1$-C$_4$)alkyl- wherein any (C$_3$-C$_7$)carbocyclyl, (C$_3$-C$_7$)carbocyclyl-(C$_1$-C$_4$)alkyl-, aryl, aryl-(C$_1$-C$_4$)alkyl-, heteroaryl, heteroaryl-(C$_1$-C$_4$)alkyl-, 3-7 membered-monocyclic-heterocycle, or 3-7 membered-monocyclic-heterocycle-(C$_1$-C$_4$)alkyl- of B" is optionally substituted with one or more Z$^1$ groups;

each R$^{1D}$ is independently:
(a) (C$_1$-C$_{14}$)alkyl substituted with one or more groups selected from the group consisting of —NR$^{b2}$R$^{c2}$, —NHNH$_2$, —C(=NR$^{a2}$)(NR$^{b2}$R$^{c2}$), —R$^{a2}$C(=NR$^{a2}$)(R$^{a2}$), and —R$^{a2}$C(=NR$^{a2}$)(NR$^{b2}$R$^{c2}$) and wherein (C$_1$-C$_{14}$)alkyl is optionally substituted independently with one or more halo, (C$_1$-C$_4$)alkyl or (C$_3$-C$_7$)carbocyclyl; or
(b) (C$_3$-C$_7$)carbocyclyl, (C$_3$-C$_7$)carbocyclyl-(C$_1$-C$_4$)alkyl-, 4-7 membered monocyclic heterocyclyl, or 4-7 membered monocyclic heterocyclyl-(C$_1$-C$_4$)alkyl-, wherein each (C$_3$-C$_7$)carbocyclyl or (C$_3$-C$_7$)carbocyclyl-(C$_1$-C$_4$)alkyl- is independently substituted with one or more Z$^2$ or Z$^3$, and wherein each 4-7 membered monocyclic heterocyclyl or 4-7 membered monocyclic heterocyclyl-(C$_1$-C$_4$)alkyl- is independently optionally substituted with one or more Z$^2$ or Z$^3$, and wherein any (C$_3$-C$_7$)carbocyclyl, (C$_3$-C$_7$)carbocyclyl-(C$_1$-C$_4$)alkyl-, 4-7 membered monocyclic heterocyclyl, or 4-7 membered monocyclic heterocyclyl-(C$_1$-C$_4$)alkyl- of R$^1$ is optionally substituted independently with one or more halo, (C$_1$-C$_4$)alkyl or (C$_3$-C$_7$)carbocyclyl;

R$^{2D}$ is hydrogen, (C$_1$-C$_4$)alkyl or phenyl(C$_1$-C$_3$)alkyl-, wherein the phenyl is optionally substituted with one or more (C$_1$-C$_4$)alkyl, —O(C$_1$-C$_4$)alkyl, halogen, or —NO$_2$;

R$^{3D}$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

R$^{4D}$ is hydrogen, halo, (C$_1$-C$_4$)alkyl, (C$_1$-C$_4$)haloalkyl, (C$_1$-C$_4$)alkoxy, (C$_1$-C$_4$)haloalkoxy, aryl, or heteroaryl wherein the aryl or heteroaryl is optionally substituted with one or more groups independently selected from the group consisting of halo, —OH, —NO$_2$, —CN, (C$_1$-C$_4$)alkyl, (C$_1$-C$_4$)haloalkyl, (C$_1$-C$_4$)alkoxy, and (C$_1$-C$_4$)haloalkoxy;

$R^{5D}$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy;

$R^{6D}$ is hydrogen, halo, $(C_1-C_4)$alkyl, $(C_1-C_4)$haloalkyl, $(C_1-C_4)$alkoxy, $(C_1-C_4)$haloalkoxy, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy;

each $Z^1$ is independently halo, —OH, —NO$_2$, —CN, $(C_1-C_4)$alkyl, $(C_1-C_4)$haloalkyl, $(C_1-C_4)$alkoxy, or $(C_1-C_4)$haloalkoxy;

each $Z^2$ is independently selected from the group consisting of —NR$^3$R$^3$, —NHNH$_2$, —C(=NR$^{a3}$)(NR$^{b3}$R$^{c3}$), —NR$^{a3}$C(=NR$^{a3}$)(R$^{d3}$), and —NR$^{a3}$C(=NR$^{a3}$)(NR$^{b3}$R$^{c3}$)

each $Z^3$ is independently —$(C_1-C_6)$alkyl substituted with one or more $Z^2$ and optionally substituted with one or more $Z^4$;

each $Z^4$ is independently halo or $(C_3-C_7)$carbocyclyl;

each $R^a$ is independently hydrogen, $(C_1-C_4)$alkyl or $(C_3-C_7)$carbocyclyl;

each $R^{a2}$ is independently hydrogen, $(C_1-C_4)$alkyl or $(C_3-C_7)$carbocyclyl;

each $R^{b2}$ and $R^{c2}$ is independently hydrogen, $(C_1-C_4)$alkyl or $(C_3-C_7)$carbocyclyl;

$R^{d2}$ is $(C_1-C_4)$alkyl or $(C_3-C_7)$carbocyclyl;

each $R^{a3}$ is independently hydrogen $(C_1-C_4)$alkyl or $(C_3-C_7)$carbocyclyl;

each $R^{b3}$ and $R^{c3}$ is independently hydrogen $(C_1-C_4)$alkyl or $(C_3-C_7)$carbocyclyl; and $R^{d3}$ is $(C_1-C_4)$alkyl or $(C_3-C_7)$carbocyclyl.

It is understood that the embodiments provided below are for compounds of formula V and all sub-formulas thereof (e.g., formulas Va). It is to be understood the two or more embodiments may be combined.

In one embodiment A" is —C(=O)N(R$^{a1}$)—R$^{1D}$.

In one embodiment R$^{a1}$ is hydrogen.

In one embodiment R$^{2D}$ is hydrogen or $(C_1-C_6)$alkyl.

In one embodiment R$^{2D}$ is hydrogen.

In one embodiment a compound of formula I is a compound of formula Va:

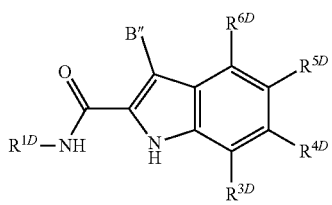

or a pharmaceutically acceptable salt thereof.

In one embodiment R$^{3D}$ is hydrogen, halo, $(C_1-C_4)$alkyl, $(C_1-C_4)$haloalkyl, $(C_1-C_4)$alkoxy, or $(C_1-C_4)$haloalkoxy.

In one embodiment R$^{3D}$ is hydrogen.

In one embodiment R$^{4D}$ is hydrogen, aryl, or heteroaryl wherein the aryl or heteroaryl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy.

In one embodiment R$^{4D}$ is phenyl wherein the phenyl is optionally substituted with one or more groups independently selected from the group consisting of halo, —OH, —NO$_2$, —CN, $(C_1-C_4)$alkyl, $(C_1-C_4)$haloalkyl, $(C_1-C_4)$alkoxy, and $(C_1-C_4)$haloalkoxy.

In one embodiment R$^{4D}$ is phenyl wherein the phenyl is optionally substituted with one or more halo.

In one embodiment R$^{4D}$ is 4-fluorophenyl.

In one embodiment R$^{5D}$ is hydrogen, halo, $(C_1-C_4)$alkyl, $(C_1-C_4)$haloalkyl, $(C_1-C_4)$alkoxy, or $(C_1-C_4)$haloalkoxy.

In one embodiment R$^{5D}$ is hydrogen.

In one embodiment R$^{6D}$ is hydrogen, halo, $(C_1-C_4)$alkyl, $(C_1-C_4)$haloalkyl, $(C_1-C_4)$alkoxy, or $(C_1-C_4)$haloalkoxy.

In one embodiment R$^{6D}$ is hydrogen.

In one embodiment B" is $(C_3-C_7)$carbocyclyl, $(C_3-C_7)$carbocyclyl-$(C_1-C_4)$alkyl-, aryl, aryl-$(C_1-C_4)$alkyl-, heteroaryl, or heteroaryl-$(C_1-C_4)$alkyl-, wherein any $C_3-C_7$) carbocyclyl, $(C_3-C_7)$carbocyclyl-$(C_1-C_4)$alkyl-, aryl, aryl-$(C_1-C_4)$alkyl-, heteroaryl, or heteroaryl-$(C_1-C_4)$alkyl- of B" is optionally substituted with one or more $Z^1$ groups.

In one embodiment B" is $(C_3-C_7)$carbocyclyl, aryl, aryl-$(C_1-C_4)$alkyl-, or heteroaryl wherein any $(C_3-C_7)$carbocyclyl, aryl, aryl-$(C_1-C_4)$alkyl-, or heteroaryl, of B" is optionally substituted with one or more $Z^1$ groups.

In one embodiment B" is $(C_3-C_7)$carbocyclyl, phenyl, phenyl-$(C_1-C_4)$alkyl-, or 5-6 membered heteroaryl wherein any $(C_3-C_7)$carbocyclyl, phenyl, phenyl-$(C_1-C_4)$alkyl-, or 5-6 membered heteroaryl of B" is optionally substituted with one or more $Z^1$ groups.

In one embodiment B" is $(C_3-C_7)$carbocyclyl, phenyl, phenyl-$(C_1-C_4)$alkyl-, or 5-6 membered heteroaryl wherein any $(C_3-C_7)$carbocyclyl, phenyl, phenyl-$(C_1-C_4)$alkyl-, or 5-6 membered heteroaryl of B" is optionally substituted with one or more $Z^1$ groups.

In one embodiment B" is $(C_3-C_7)$carbocyclyl, phenyl, phenyl-$(C_1-C_4)$alkyl-, or 6 membered heteroaryl wherein any $(C_3-C_7)$carbocyclyl, phenyl, phenyl-$(C_1-C_4)$alkyl-, or 6 membered heteroaryl of B" is optionally substituted with one or more $Z^1$ groups.

In one embodiment B" is $(C_3-C_7)$carbocyclyl, phenyl, phenyl-$(CH_2)$—, or pyridinyl wherein any phenyl, phenyl-$(CH_2)$—, or pyridinyl of B" is optionally substituted with one or more $Z^1$ groups.

In one embodiment each $Z^1$ is independently halo, —OH, or $(C_1-C_4)$haloalkyl.

In one embodiment B" is 4-fluorophenyl, cyclopropyl, benzyl, pyrdin-4-yl, 4-hydroxyphenyl, or 4-trifluoromethylphenyl.

In one embodiment R$^{1D}$ is $(C_1-C_{14})$alkyl substituted with one or more groups independently selected from —NR$^{b2}$R$^{c2}$ and wherein the $(C_1-C_{14})$alkyl is optionally substituted with one or more $(C_3-C_7)$carbocyclyl.

In one embodiment R$^{1D}$ is $(C_2-C_{10})$alkyl substituted with one or more groups independently selected from —NR$^{b2}$R$^{c2}$ and wherein the $(C_2-C_{10})$alkyl is optionally substituted with one or more $(C_3-C_7)$carbocyclyl.

In one embodiment R$^{1D}$ is $(C_4-C_8)$alkyl substituted with two or more groups independently selected from —NR$^{b2}$R$^{c2}$.

In one embodiment R$^{b2}$ and R$^{c2}$ are each hydrogen.

In one embodiment R$^{1D}$ is a 4-7 membered monocyclic heterocyclyl-$(C_1-C_4)$alkyl-, wherein the 4-7 membered monocyclic heterocyclyl-$(C_1-C_4)$alkyl- is substituted with one or more groups independently selected from the group consisting of Z and —$(C_1-C_6)$alkyl substituted with one or more Z, wherein each Z is independently selected from the group consisting of —NR$^{b3}$R$^{c3}$, —NHNH$_2$, —C(=NR$^{a3}$)(NR$^{b3}$R$^{c3}$), —NR$^{a3}$C(=NR$^{a3}$)(R$^{a3}$), and —NR$^{a3}$C(=NR$^{a3}$)(NR$^{b3}$R$^{c3}$) and wherein the 4-7 membered monocyclic heterocyclyl-(C$_1$-C$_4$)alkyl- is optionally substituted with one or more (C$_1$-C$_6$)alkyl.

In one embodiment R$^{1D}$ is a 4-7 membered monocyclic heterocyclyl-(C$_1$-C$_4$)alkyl-, wherein the 4-7 membered monocyclic heterocyclyl-(C$_1$-C$_4$)alkyl- is substituted with one or more groups independently selected from the group consisting of Z and (C$_1$-C$_6$)alkyl substituted with one or more Z, wherein each Z is independently —NR$^{b3}$R$^{c3}$ and wherein the 4-7 membered monocyclic heterocyclyl-(C$_1$-C$_4$)alkyl- is optionally substituted with one or more (C$_1$-C$_6$)alkyl.

In one embodiment R$^{1D}$ is pyrrolidinyl-(C$_1$-C$_4$)alkyl-, wherein the pyrrolidinyl-(C$_1$-C$_4$)alkyl- is substituted with one or more groups independently selected from the group consisting of Z and —(C$_1$-C$_6$)alkyl substituted with one or more Z, wherein each Z is independently —NR$^{b3}$R$^{c3}$ and wherein is pyrrolidinyl-(C$_1$-C$_4$)alkyl- is optionally substituted independently with one or more (C$_1$-C$_6$)alkyl In one embodiment R$^{1D}$ is pyrrolidinyl-(CH$_2$)—, wherein the pyrrolidinyl-(CH$_2$)— is substituted with one or more groups independently selected from the group consisting of Z and —(C$_1$-C$_6$)alkyl substituted with one or more Z, wherein each Z is independently —NR$^{b3}$R$^{c3}$ and wherein the pyrrolidinyl-(CH$_2$)— is optionally substituted independently with one or more (C$_1$-C$_6$)alkyl.

In one embodiment R$^{1D}$ is pyrrolidinyl-(CH$_2$)—, wherein the pyrrolidinyl-(CH$_2$)— is substituted on the pyrrolidinyl with —(C$_1$-C$_6$)alkyl substituted with one or more —NR$^{b3}$R$^{c3}$.

In one embodiment R$^{b3}$ and R$^{c3}$ are each hydrogen.

In one embodiment R$^{1D}$ is:

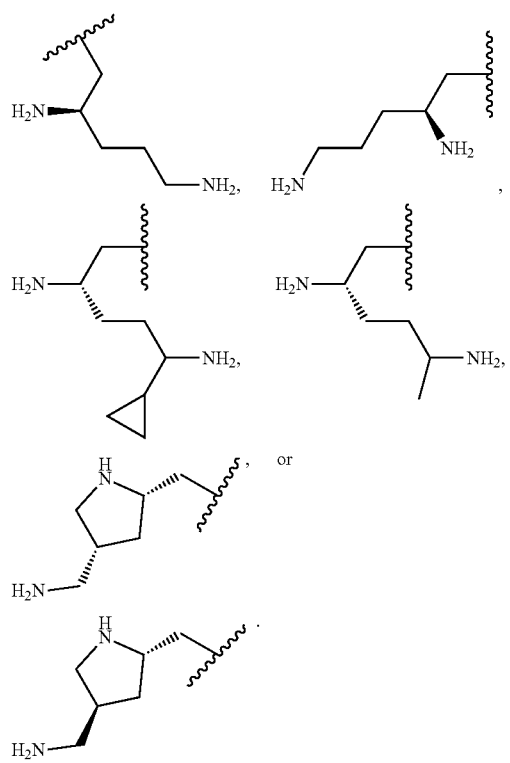

In one embodiment A" is:

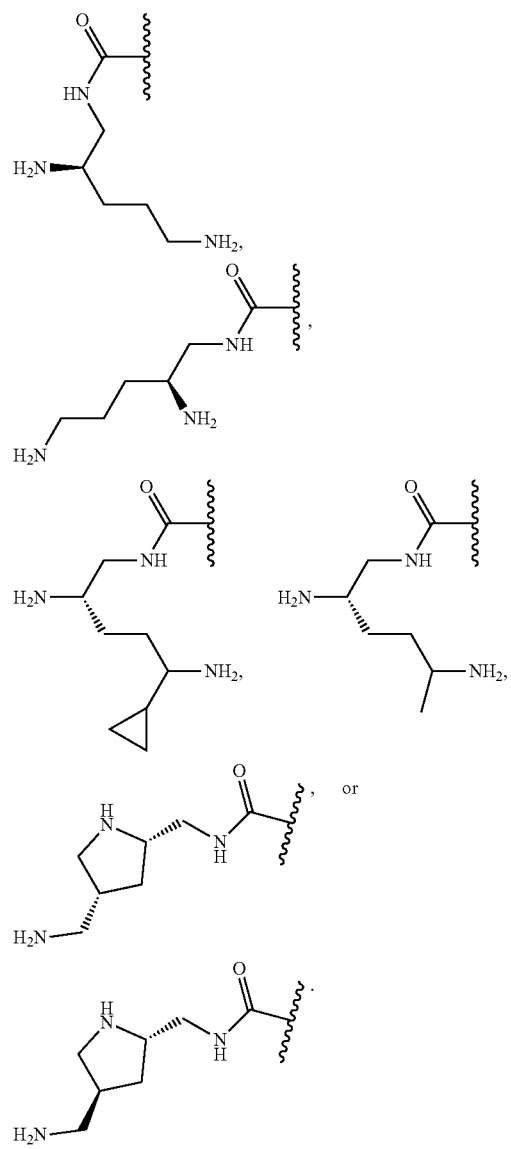

Generally, the bacterial efflux pump inhibitors discussed here can be prepared as illustrated in the following General Methods and Schemes as well as U.S. Patent Application Publication US2016/0271082 which document is hereby incorporated by reference in its entirety. It is understood that variable groups shown below (e.g., R) can represent the final corresponding groups present in a final compound or that these groups can represent groups that can be converted to the final corresponding groups present in a final compound at a convenient point in a synthetic sequence. For example, the variable groups can contain one or more protecting groups that can be removed at a convenient point in a synthetic sequence to provide the final corresponding groups in the final compound. The reagents and conditions shown are exemplary and non-limiting. Other reagents and conditions can be used in the general synthetic schemes.

Schemes 14, 15 and 16 illustrate some general methods for the preparation of substituted 1[H]-indole carboxamides.

Scheme 14

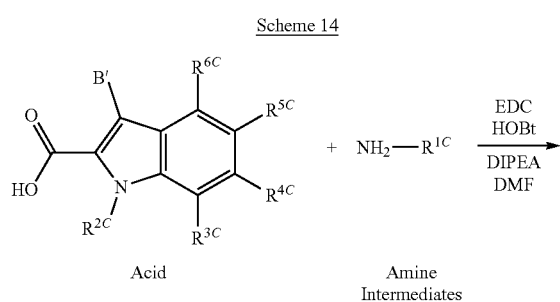

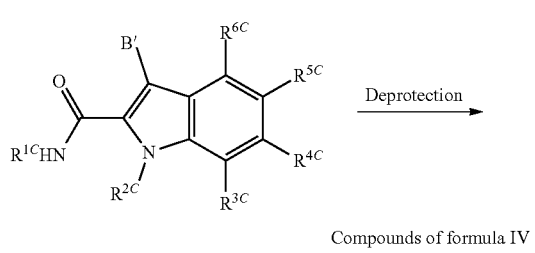

Compounds of formula IV

Scheme 15

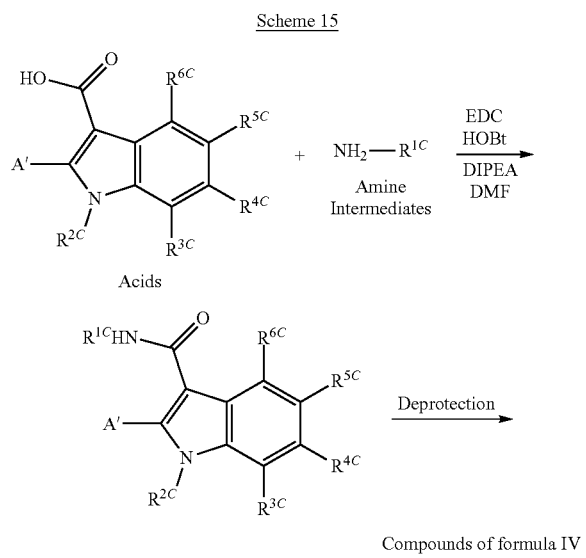

Compounds of formula IV

Scheme 16

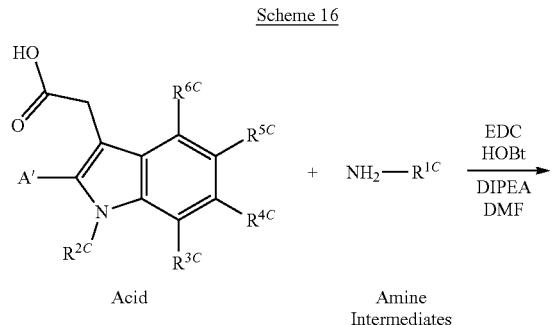

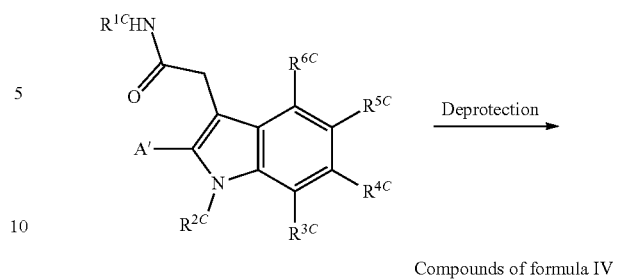

Compounds of formula IV

Scheme 17 illustrates some a general method for the preparation of certain efflux pump inhibitors (e.g., compounds of formula III).

Scheme 17

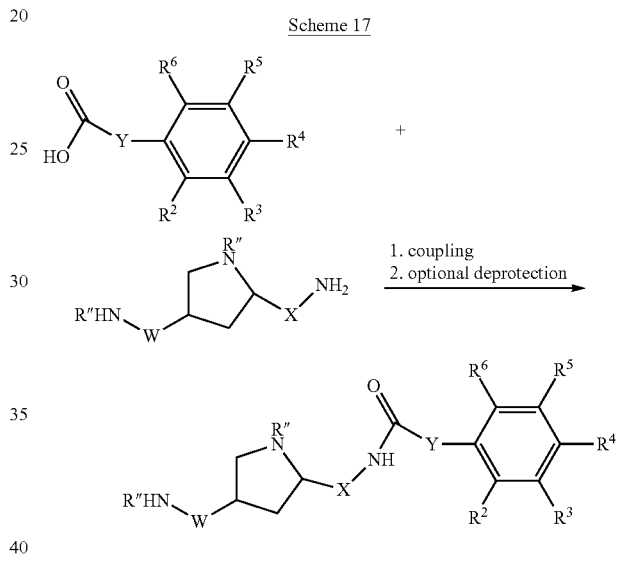

(each R″ is a protecting group, hydrogen or ($C_1$-$C_4$)alkyl; W is a —($C_1$-$C_6$)alkyl or absent; X is —($C_1$-$C_4$)alkyl- or absent; and Y is a —($C_1$-$C_3$)alkyl- or absent)

Schemes 18 and 19 illustrate some general methods for the preparation of substituted indole carboxamide efflux pump inhibitors.

Scheme 18

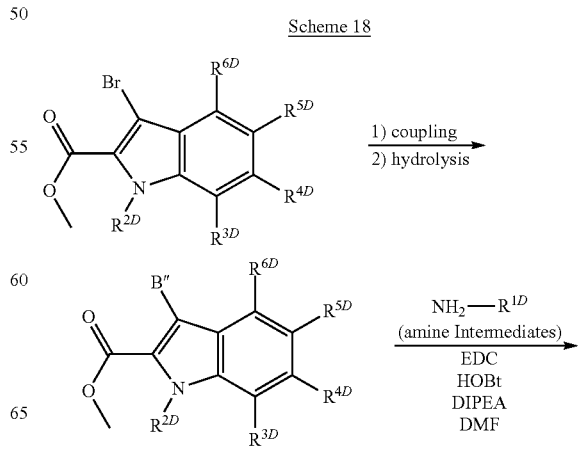

-continued

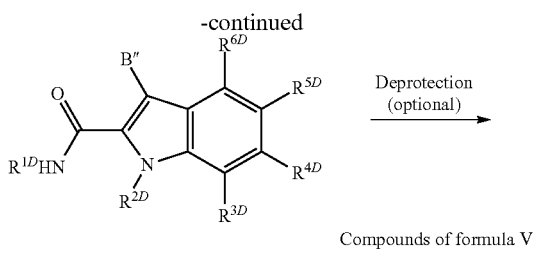

Compounds of formula V

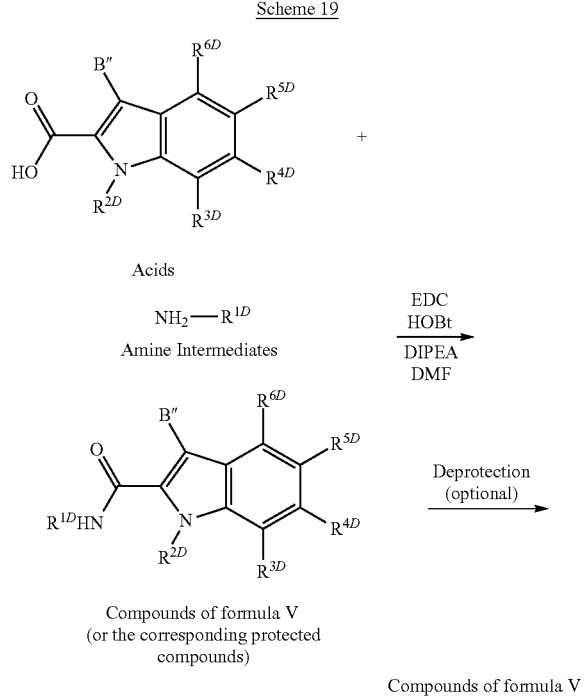

As used herein, the term "minimum inhibitory concentration (MIC)" refers to the lowest concentration of a compound (e.g., an antibiotic) that prevents visible growth of a bacterium. Assays for measuring the MIC of a compound are known in the art, for example, as described herein. As used herein, the term "intrinsic MIC" refers the MIC of a compound (e.g., an antibiotic) for the particular bacterial species that has not been pre-exposed to the compound.

As used herein, the term "sub-inhibitory concentration" refers to a concentration of the antibiotic that does not reduce the visible growth of the bacteria. In certain embodiments, the sub-inhibitory concentration is ½×MIC of the antibiotic. In certain embodiments, the sub-inhibitory concentration of the antibiotic is a concentration that is capable of inducing the expression of one or more efflux pumps in the bacteria.

As used herein, the term "inhibitory concentration" refers to a concentration of the antibiotic that reduces the visible growth of the bacteria. In certain embodiments, this concentration is the intrinsic MIC of the antibiotic.

In certain embodiments the compound of formula I is an effective antibiotic when administered alone.

In certain embodiments, the combination of the compound of formula I and a bacterial efflux pump inhibitor is a synergistic combination.

In certain embodiments, the animal is a non-human animal. For example, in certain embodiments, the animal is a mouse.

An efflux pump inhibitor is a compound that interferes with the ability of an efflux pump to export a substrate. The inhibitor may have intrinsic antibacterial properties of its own. The compounds disclosed herein may be useful for treating bacterial infections (e.g., Gram-negative and Gram-positive) when administered with an bacterial efflux pump inhibitor.

In one embodiment the bacterial infection being treated is a Gram-negative bacterial strain infection. In one embodiment the Gram-negative bacterial strain is selected from the group consisting of *Acinetobacter baumannii, Acinetobacter calcoaceticus, Acinetobacter haemolyticus, Acinetobacter lwoffi, Actinobacillus actinomycetemcomitans, Aeromonas hydrophilia, Aggregatibacter actinomycetemcomitans, Agrobacterium tumefaciens, Bacteroides distasonis, Bacteroides eggerthii, Bacteroides forsythus, Bacteroides fragilis, Bacteroides ovalus, Bacteroides splanchnicus, Bacteroides thetaiotaomicron, Bacteroides unformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coi, Campylobacter fetus, Campylobacter jejuni, Caulobacter crescentus, Chlamydia trachomatis, Citrobacter diversus, Citrobacter freundii, Enterobacter aerogenes, Enterobacter asburiae, Enterobacter cloacae, Enterobacter sakazakii, Escherchia coli, Francisella tularensis, Fusobacterium nucleatum, Gardnerella vaginalis, Haemophilus ducreyi, Haemophilus haemolyticus, Haemophilus influenzae, Haemophilus parahaemolyticus, Haemophilus parainfluenzae, Helicobacter pylori, Kingella denitrificans, Kingella indologenes, Kingella kingae, Kingella oralis, Klebsiella oxytoca, Klebsiella pneumoniae, Klebsiella rhinoscleromatis, Legionella pneumophila, Listeria monocytogenes, Moraxella bovis, Moraxella catarrhalis, Moraxella lacunata, Morganella morganii, Neisseria gonorrhoeae, Neisseria meningitidis, Pantoea agglomerans, Pasteurella canis, Pasteurella haemolytica, Pasteurella multocida, Pasteurella tularensis, Porphyromonas gingivalis, Proteus mirabilis, Proteus vulgaris, Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella jlexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis* and *Yersinia pseudotuberculosis*.

In one embodiment the bacterial infection being treated is a Gram-positive bacterial strain infection. In one embodiment the Gram-positive bacterial strain is selected from the group consisting of *Actinomyces naeslundii, Actinomyces viscosus, Bacillus anthracis, Bacillus cereus, Bacillus subtilis, Clostridium difficile, Corynebacterium diphtheriae, Corynebacterium ulcerans, Enterococcus faecalis, Enterococcus faecium, Micrococcus luteus, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans,*

*Streptococcus pneumoniae, Streptococcus pyogenes, Streptococcus salivarius* and *Streptococcus sanguis*.

In one embodiment, the animal is infected with *P. aeruginosa*.

In one embodiment, the animal is infected with *E. coli*.

In one embodiment, the animal is infected with *K. pneumoniae*.

In one embodiment, the animal is infected with *A. baumannii*.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, an antimicrobial (for example, an aminoglycoside, an antifungal, an antiparasitic, an antiviral, a carbapenem, a cephalosporin (e.g., cefepime), a fluoroquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropoietin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

It will also be appreciated by those skilled in the art that certain compounds of the invention can exist in more than one tautomeric form. For example, a substituent of formula —NH—C(=O)H in a compound of formula (I) could exist in tautomeric form as —N=C(OH)H. The present invention encompasses all tautomeric forms of a compound of formula I as well as mixtures thereof that can exist in equilibrium with non-charged and charged entities depending upon pH, which possess the useful properties described herein In cases where compounds are sufficiently basic or acidic, a salt of a compound of formula I can be useful as an intermediate for isolating or purifying a compound of formula I.

Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $H_2PO_4^-$, $CF_3SO_3^-$, $p\text{-}CH_3C_6H_4SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well-known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1 to about 500 mg/kg, e.g., from about 5 to about 400 mg/kg of body weight per day, such as 1 to about 250 mg per kilogram body weight of the recipient per day.

The compound is conveniently formulated in unit dosage form; for example, containing 5 to 500 mg, 10 to 400 mg, or 5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Co-administration of a compound disclosed herein with one or more other active therapeutic agents (e.g., antibacterial agents) generally refers to simultaneous or sequential administration of a compound disclosed herein and one or more other active therapeutic agents, such that therapeutically effective amounts of disclosed herein and one or more other active therapeutic agents are both present in the body of the patient.

The ability of a compound to produce an antibiotic effect can be determined using a method as described in Example 11. Data for representative compounds used in combination with the bacterial efflux pump inhibitor (EPI) N-(((2S,4R)-4-(aminomethyl)pyrrolidin-2-yl)methyl)-6-(4-fluorophenyl)-1H-indole-2-carboxamide is shown in Table 1.

TABLE 1

| Example | Structure | MIC (wo EPI/ w EPI) P. Aeruginosa PAO1 | |
|---|---|---|---|
| | | Intrinsic MIC | MIC in the Presence of EPI* |
| 1 | 1-(5-bromo-1H-indol-2-yl)ethan-1-amine | 128 | 8 |
| 2 | 1-(5-bromo-1H-indol-2-yl)pentan-1-amine | >256 | 64 |
| 3 | N-methyl-1-(5-bromo-1H-indol-2-yl)ethan-1-amine | >256 | 64 |
| 4 | 1-(1H-indol-2-yl)ethan-1-amine | >256 | 128 |
| 5 | 1-(5-bromo-1-methyl-1H-indol-2-yl)ethan-1-amine | >256 | 64 |
| 6 | 1-(5-bromo-1H-indol-2-yl)ethane-1,2-diamine | 256 | 128 |

TABLE 1-continued

| Example | Structure | MIC (wo EPI/ w EPI) P. Aeruginosa PA01 | |
|---|---|---|---|
| | | Intrinsic MIC | MIC in the Presence of EPI* |
| 7 | 1-(5-fluoro-1H-indol-2-yl)ethanamine | 256 | 16 |
| 8 | 1-(5-methoxy-1H-indol-2-yl)ethanamine | >256 | 256 |
| 9 | 1-(5-trifluoromethyl-1H-indol-2-yl)ethanamine | >256 | 16 |
| 10 | 1-(6-bromo-1H-indol-2-yl)ethanamine | >256 | 32 |
| 11 | 1-(5-trifluoromethoxy-1H-indol-2-yl)ethanamine | >256 | 64 |
| 12 | N,N-dimethyl-1-(1H-indol-2-yl)ethanamine | >256 | 256 |

TABLE 1-continued
| Example | Structure | MIC (wo EPI/ w EPI) P. Aeruginosa PAO1 | |
|---|---|---|---|
| | | Intrinsic MIC | MIC in the Presence of EPI* |
| 13 | 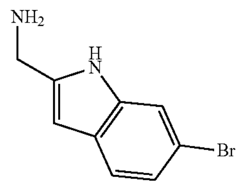 [SMILES: NCc1cc2ccc(Br)cc2[nH]1] | 64 | 16 |
| 14 | 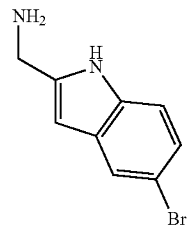 [SMILES: NCc1cc2cc(Br)ccc2[nH]1] | 128 | 8 |
| 15 | 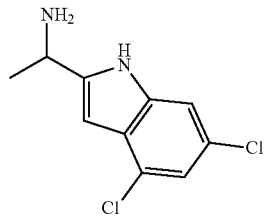 | 256 | 16 |
| 16 | 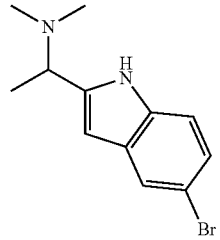 | 256 | 64 |
| 17 | 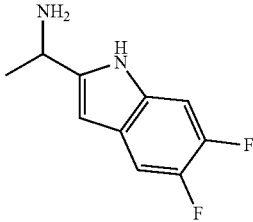 | 256 | 8 |
| 18 | 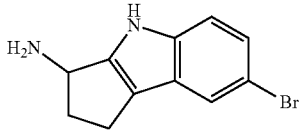 [SMILES: NC1CCc2c1[nH]c1ccc(Br)cc21] | 128 | 2 |
| 19 | 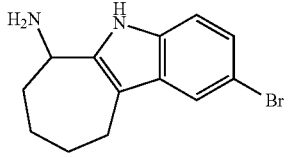 [SMILES: NC1CCCCc2c1[nH]c1ccc(Br)cc21] | 128 | 4 |

TABLE 1-continued

| | | MIC (wo EPI/ w EPI) *P. Aeruginosa* PAO1 | |
|---|---|---|---|
| Example | Structure | Intrinsic MIC | MIC in the Presence of EPI* |
| 20 | 1,2-dichloro cyclohepta[b]indole with NH₂ | 32 | 1 |
| 21 | 2,3-dichloro cyclohepta[b]indole with NH₂ | 256 | 32 |
| 22 | 6,7-dichloro cyclopenta[b]indole with NH₂ | 32 | 1 |
| 23 | 7,8-dichloro cyclopenta[b]indole with NH₂ | 64 | 8 |
| 24 | H₂N-propyl-NH-CH(CH₃)-(5-bromoindol-2-yl) | 64(128) | 128 |
| 25 | 4,5-dichlorothiophene-2-carboxamide-propyl-NH-CH(CH₃)-(5-bromoindol-2-yl) | >256 | 16 |
| 26 | 5-chlorofuran-2-carboxamide-propyl-NH-CH(CH₃)-(5-bromoindol-2-yl) | >256 | 16 |

TABLE 1-continued

| Example | Structure | MIC (wo EPI/ w EPI) *P. Aeruginosa* PAO1 | |
|---|---|---|---|
| | | Intrinsic MIC | MIC in the Presence of EPI* |
| 27 | (5-chlorothiophene-2-carboxamide linked via propyl-NH to 1-(5-bromo-1H-indol-2-yl)ethyl) | 32(>256) | 64 |
| 28 | (3-aminopropyl-NH on cyclohepta[b]indole, Br-substituted) | 64(32) | 32 |
| 29 | (3-aminopropyl-NH on cyclopenta[b]indole, Br-substituted) | 64(128) | 128 |
| 30 | (5-bromoindol-2-yl ethyl-NH-propyl-NH-C(O)-3,4-dichlorophenyl) | >256 | 32 |
| 31 | (5-bromoindol-2-yl ethyl-NH-propyl-NH-C(O)-cyclohexyl) | >256 | 128 |
| 32 | (5-bromoindol-2-yl ethyl-NH-butyl) | >256 | 64 |
| 33 | (5-bromoindol-2-yl ethyl-NH-CH2CH2-phenyl) | >256 | 32 |

TABLE 1-continued
| Example | Structure | MIC (wo EPI/ w EPI) P. Aeruginosa PAO1 | |
|---|---|---|---|
| | | Intrinsic MIC | MIC in the Presence of EPI* |
| 34 | 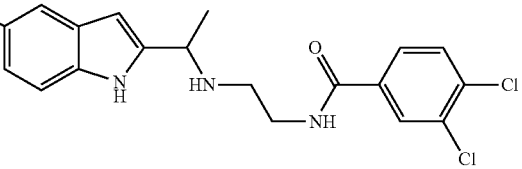 | >256 | 32 |
| 35 | 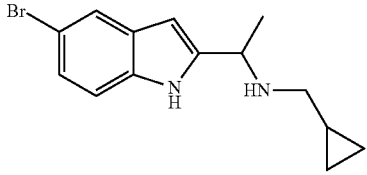 [SMILES: CC(NCC1CC1)c1cc2cc(Br)ccc2[nH]1] | >256 | 256 |
| 36 | 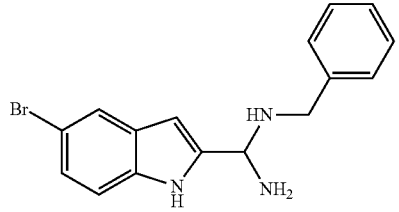 [SMILES: NC(NCc1ccccc1)c1cc2cc(Br)ccc2[nH]1] | >256 | 32 |
| 37 | 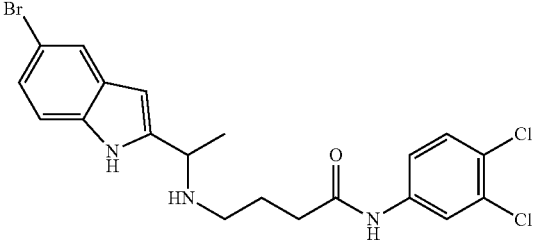 [SMILES: CC(NCCCC(=O)Nc1ccc(Cl)c(Cl)c1)c1cc2cc(Br)ccc2[nH]1] | >256 | 16 |
| 38 | 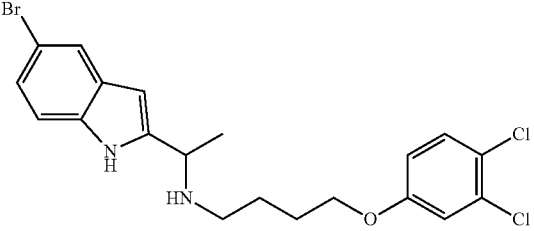 [SMILES: CC(NCCCCOc1ccc(Cl)c(Cl)c1)c1cc2cc(Br)ccc2[nH]1] | >256 | 16 |
| 39 | 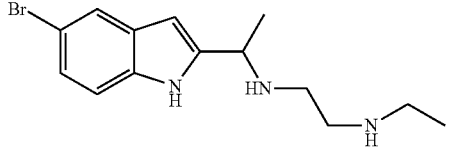 [SMILES: CCNCCNC(C)c1cc2cc(Br)ccc2[nH]1] | >256 | >256 |
*In the presence of 12.5 μg/ml of N-(((2S,4R)-4-(aminomethyl)pyrrolidin-2-yl)methyl)-6-(4-fluorophenyl)-1H-indole-2-carboxamide.

The MICs obtained for representative compounds against *E. coli, K. pneumoniae* and *A. baumannii* are provided in Table 2.

TABLE 2

| Example | Structure | E. coli ATCC 25922 | K. pneumoniae ATCC 10031 Intrinsic MIC (ug/ml) | A. baumannii ATCC 19606 |
|---|---|---|---|---|
| 1 | 1-(5-bromo-1H-indol-2-yl)ethan-1-amine | 128 | 64 | 128 |
| 2 | 1-(5-bromo-1H-indol-2-yl)pentan-1-amine | 16 | 16 | 32 |
| 3 | 1-(5-bromo-1H-indol-2-yl)-N-methylethan-1-amine | 256 | 128 | 64 |
| 4 | 1-(1H-indol-2-yl)ethan-1-amine | >256 | >256 | >256 |
| 5 | 1-(5-bromo-1-methyl-1H-indol-2-yl)ethan-1-amine | 128 | 64 | 128 |
| 6 | 1-(5-bromo-1H-indol-2-yl)pentan-1-amine isomer | 128 | 64 | 128 |

TABLE 2-continued

| Example | Structure | E. coli ATCC 25922 | K. pneumoniae ATCC 10031 Intrinsic MIC (ug/ml) | A. baumannii ATCC 19606 |
|---|---|---|---|---|
| 7 | 1-(5-fluoro-1H-indol-2-yl)ethan-1-amine | >256 | >256 | >256 |
| 8 | 1-(5-methoxy-1H-indol-2-yl)ethan-1-amine | >256 | >256 | 256 |
| 9 | 1-(5-(trifluoromethyl)-1H-indol-2-yl)ethan-1-amine | 128 | 64 | 64 |
| 10 | 1-(6-bromo-1H-indol-2-yl)ethan-1-amine | 256 | 128 | 128 |
| 11 | 1-(5-(trifluoromethoxy)-1H-indol-2-yl)ethan-1-amine | 128 | 64 | 64 |
| 12 | N,N-dimethyl-1-(1H-indol-2-yl)ethan-1-amine | >256 | >256 | >256 |
| 13 | (6-bromo-1H-indol-2-yl)methanamine | 256 | 256 | 128 |

TABLE 2-continued

| Example | Structure | E. coli ATCC 25922 | K. pneumoniae ATCC 10031 Intrinsic MIC (ug/ml) | A. baumannii ATCC 19606 |
|---|---|---|---|---|
| 14 | 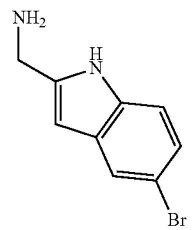 [SMILES: NCc1cc2cc(Br)ccc2[nH]1] | 128 | 64 | 64 |
| 15 | 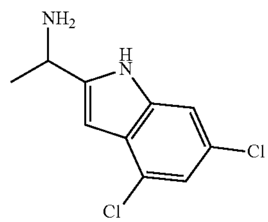 | 128 | 64 | 32 |
| 16 | 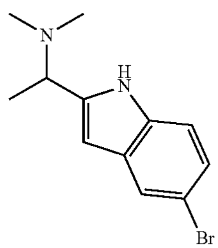 | 256 | 256 | 128 |
| 17 | 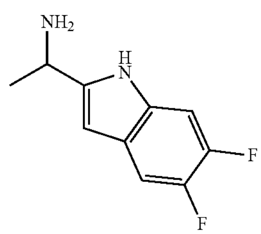 | 256 | 128 | 128 |
| 18 | 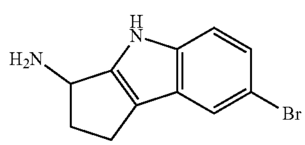 [SMILES: NC1CCc2c1[nH]c1ccc(Br)cc21] | 32 | 32 | 64 |
| 19 | 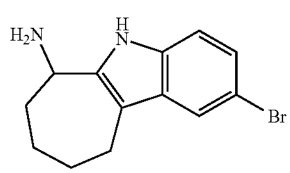 [SMILES: NC1CCCCc2c1[nH]c1ccc(Br)cc21] | 16 | 16 | 16 |
| 20 | 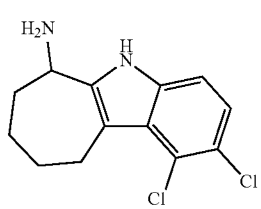 [SMILES: NC1CCCCc2c1[nH]c1ccc(Cl)c(Cl)c21] | 8 | 2 | 8 |

TABLE 2-continued

| Example | Structure | E. coli ATCC 25922 | K. pneumoniae ATCC 10031 Intrinsic MIC (ug/ml) | A. baumannii ATCC 19606 |
|---|---|---|---|---|
| 21 | (structure: 8-amino-2,3-dichloro-cyclohepta[b]indole) | 16 | 8 | 16 |
| 22 | (structure: 3-amino-7,8-dichloro-cyclopenta[b]indole) | 16 | 8 | 8 |
| 23 | (structure: 3-amino-6,8-dichloro-cyclopenta[b]indole) | 16 | 8 | 16 |
| 24 | (structure: N-(3-aminopropyl)-1-(5-bromo-1H-indol-2-yl)ethanamine) | 128 | 64 | 256 |
| 25 | (structure: 4,5-dichloro-N-(3-((1-(5-bromo-1H-indol-2-yl)ethyl)amino)propyl)thiophene-2-carboxamide) | 8 | 1 | 16 |
| 26 | (structure: 5-chloro-N-(3-((1-(5-bromo-1H-indol-2-yl)ethyl)amino)propyl)furan-2-carboxamide) | 64 | 16 | 128 |
| 27 | (structure: 5-chloro-N-(3-((1-(5-bromo-1H-indol-2-yl)ethyl)amino)propyl)thiophene-2-carboxamide) | 32 | 8 | 32 |
| 28 | (structure: N-(3-aminopropyl)-8-bromo-cyclohepta[b]indol-6-amine) | 16 | 8 | 32 |

TABLE 2-continued

| Example | Structure | E. coli ATCC 25922 | K. pneumoniae ATCC 10031 Intrinsic MIC (ug/ml) | A. baumannii ATCC 19606 |
|---|---|---|---|---|
| 29 | 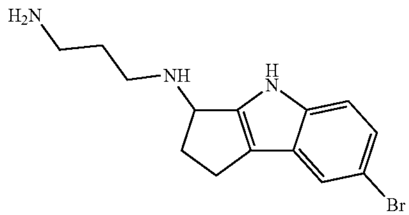 [SMILES: NCCCNC1CCc2c1[nH]c1ccc(Br)cc21] | 64 | 32 | 256 |
| 30 | 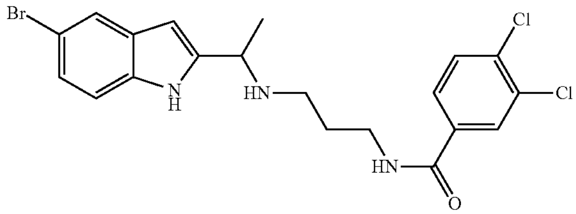 [SMILES: CC(NCCCNC(=O)c1ccc(Cl)c(Cl)c1)c1cc2cc(Br)ccc2[nH]1] | 32 | 4 | 64 |
| 31 | 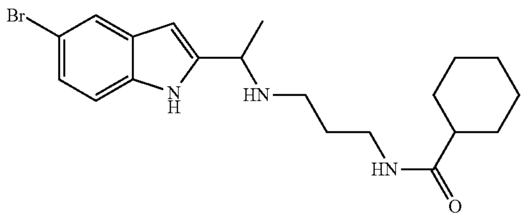 [SMILES: CC(NCCCNC(=O)C1CCCCC1)c1cc2cc(Br)ccc2[nH]1] | 64 | 16 | 64 |
| 32 | 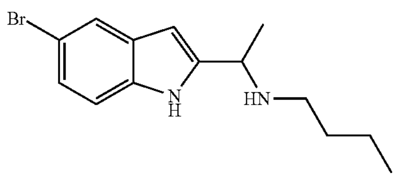 [SMILES: CCCCNC(C)c1cc2cc(Br)ccc2[nH]1] | 32 | 16 | 64 |
| 33 | 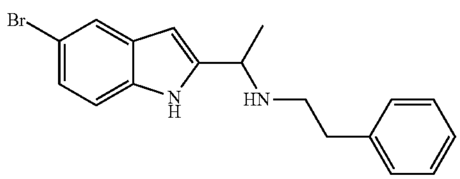 [SMILES: CC(NCCc1ccccc1)c1cc2cc(Br)ccc2[nH]1] | 16 | 4 | 32 |
| 34 | 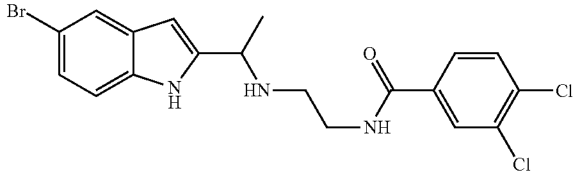 [SMILES: CC(NCCNC(=O)c1ccc(Cl)c(Cl)c1)c1cc2cc(Br)ccc2[nH]1] | 32 | 4 | 64 |
| 35 | 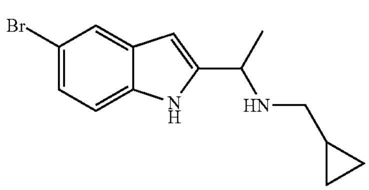 [SMILES: CC(NCC1CC1)c1cc2cc(Br)ccc2[nH]1] | 128 | 64 | 128 |

TABLE 2-continued
| Example | Structure | E. coli ATCC 25922 | K. pneumoniae ATCC 10031 Intrinsic MIC (ug/ml) | A. baumannii ATCC 19606 |
|---|---|---|---|---|
| 36 | 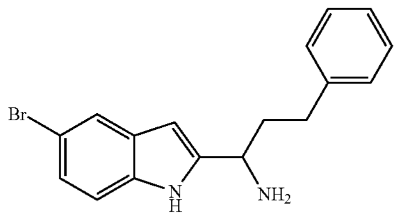 [SMILES: NC(CCc1ccccc1)c1cc2cc(Br)ccc2[nH]1] | 16 | 8 | 32 |
| 37 | 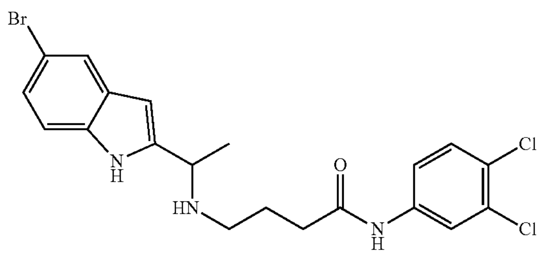 [SMILES: CC(NCCCC(=O)Nc1ccc(Cl)c(Cl)c1)c1cc2cc(Br)ccc2[nH]1] | 16 | 4 | 32 |
| 38 | 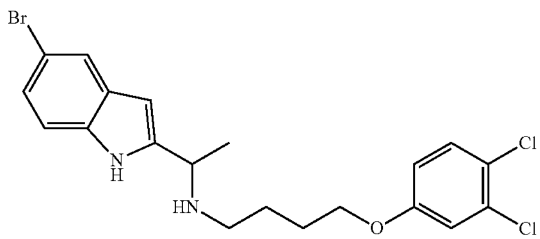 [SMILES: CC(NCCCCOc1ccc(Cl)c(Cl)c1)c1cc2cc(Br)ccc2[nH]1] | 16 | 4 | 64 |
| 39 | 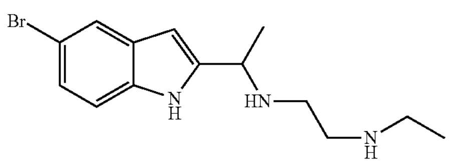 [SMILES: CCNCCNC(C)c1cc2cc(Br)ccc2[nH]1] | 256 | 128 | 256 |
The invention will now be illustrated by the following non-limiting examples.
Example 1. Preparation of 1-(5-bromo-1H-indol-2-yl)ethan-1-amine
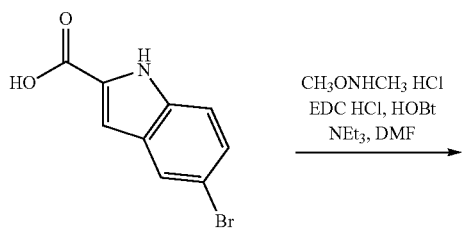
-continued
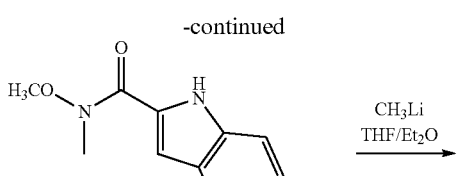
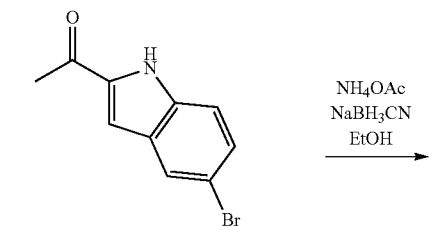

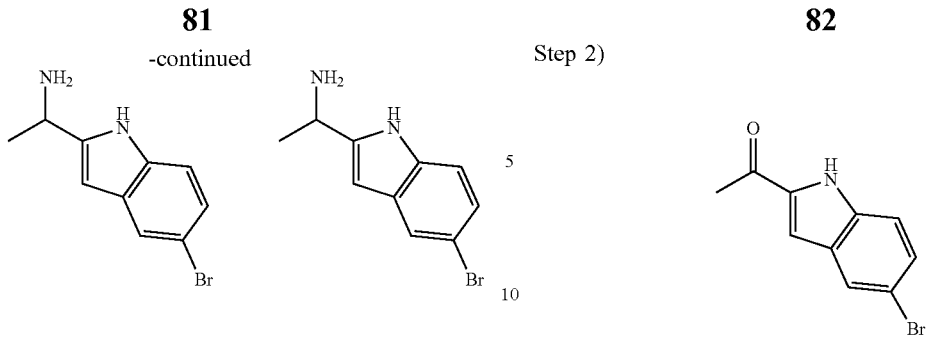

1-(5-Bromo-1H-indol-2-yl)ethan-1-amine 1-(5-Bromo-1H-indol-2-yl)ethan-1-one (95 mg, 0.40 mmol), ammonium acetate (308 mg, 4.00 mmol) and sodium cyanoborohydride (126 mg, 2.00 mmol) were dissolved in ethanol (5 mL). The mixture was stirred for overnight at 60° C. The reaction mixture was diluted with ethyl acetate. The organic layer was washed with 10% NaOH and brine, and it was dried over $Na_2SO_4$. The organic layer was concentrated under reduced pressure. The residue was purified on an ISCO chromatograph (0-10% methanol/dichloromethane+0.1% $NH_4OH$) to give the product as a yellow oil (32 mg, 33%); $^1H$ NMR (300 MHz) (DMSO-$d_6$) δ 11.07 (bs, 1H), 7.57 (d, J=2 Hz, 1H), 7.24 (d, J=9 Hz, 1H), 7.08 (dd, J=8 Hz, J=2 Hz, 1H), 6.18 (s, 1H), 4.11-4.04 (m, 1H), 1.34 (d, J=7 Hz, 3H); LC/MS RT=2.50 (M–H⁻: 237/239).

The requisite intermediate was prepared as follows:

Step 1)

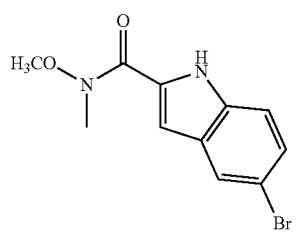 [SMILES: CON(C)C(=O)c1cc2cc(Br)ccc2[nH]1]

5-Bromo-N-methoxy-N-methyl-1H-indole-2-carboxamide

5-Bromo-1H-indole-2-carboxylic acid (1.0 g, 4.17 mmol), N,O-dimethylhydroxylamine hydrochloride (611 mg, 6.26 mmol), HOBt (563 mg, 4.17 mmol), EDC hydrochloride (1.68 g, 8.76 mmol) and triethylamine (2.32 mL, 16.68 mmol) were dissolved in anhydrous dimethylformamide (40 mL). The mixture was stirred for overnight at room temperature. The reaction mixture was diluted with ethyl acetate, and the organic layer was washed with water, saturated $NH_4Cl$, 10% NaOH and brine. The organic layer was dried over $Na_2SO_4$, and it was concentrated under reduced pressure. The residue was purified on an ISCO chromatograph (0-100% ethyl acetate/hexane) to give product as a white solid (800 mg, 68%); $^1H$ NMR (300 MHz) (CDCl$_3$) δ 9.33 (bs, 1H), 7.83 (s, 1H), 7.38 (dd, J=9 Hz, J=1 Hz, 1H), 7.31 (d, J=9 Hz, 1H), 7.15 (s, 1H), 3.85 (s, 3H), 3.43 (s, 3H).

Step 2)

1-(5-Bromo-1H-indol-2-yl)ethan-1-one

5-Bromo-N-methoxy-N-methyl-1H-indole-2-carboxamide (600 mg, 2.12 mmol) was dissolved in anhydrous tetrahydrofuran (50 mL). The mixture was cooled to −78° C., and, then, a solution of 1.6 M methyllithium in diethyl ether (4.00 mL, 6.36 mmol) was added. The mixture was stirred for 2 hours at −78° C. An additional solution of 1.6 M methyllithium in diethyl ether (4.00 mL, 6.36 mmol) was added. The mixture was stirred for an hour at −78° C. The reaction was stopped by addition of water (10 mL). After removal of the solvent, the reaction mixture was diluted with ethyl acetate. The organic layer was washed with saturated $NH_4Cl$ and brine, and it was dried over $Na_2SO_4$. The organic layer was concentrated under reduced pressure. The residue was purified on an ISCO chromatograph (0-20% ethyl acetate/hexane) to give product as a white solid (344 mg, 68%); $^1H$ NMR (300 MHz) (CDCl$_3$) δ 9.19 (bs, 1H), 7.85 (s, 1H), 7.42 (dd, J=9 Hz, J=2 Hz, 1H), 7.31 (d, J=8 Hz, 1H), 7.12 (s, 1H), 2.60 (s, 3H).

Example 2. Preparation of 1-(5-bromo-1H-indol-2-yl)pentan-1-aminium chloride

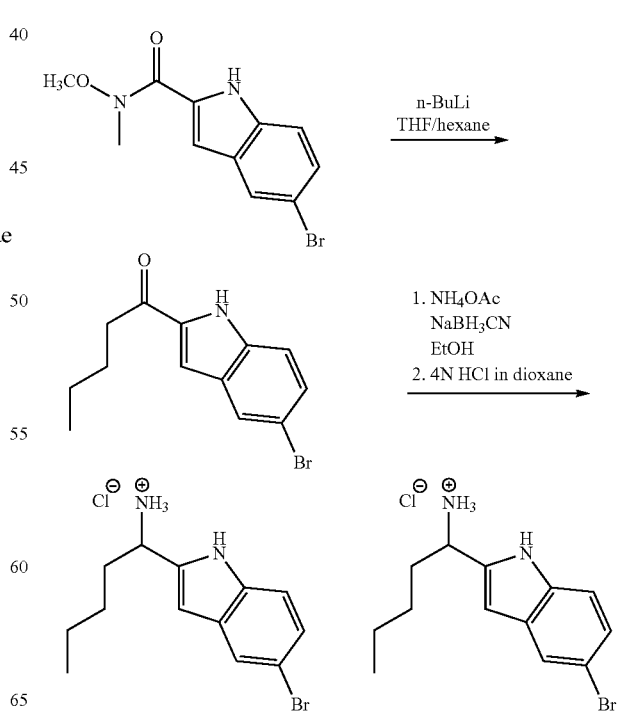

1-(5-Bromo-1H-indol-2-yl)pentan-1-aminium chloride 1-(5-Bromo-1H-indol-2-yl)pentan-1-one (100 mg, 0.36 mmol), ammonium acetate (277 mg, 3.60 mmol) and sodium cyanoborohydride (113 mg, 1.80 mmol) were dissolved in ethanol (5 mL). The mixture was stirred for overnight at 60° C. The reaction mixture was diluted with ethyl acetate. The organic layer was washed with 10% NaOH and brine, and it was dried over $Na_2SO_4$. The organic layer was concentrated under reduced pressure. The residue was purified on an ISCO chromatograph (0-10% methanol/dichloromethane+0.1% $NH_4OH$) to give crude 1-(5-bromo-1H-indol-2-yl)pentan-1-amine. The crude material was treated with 4N HCl in dioxane, and it was stirred for 15 min at 0° C. After removal of solvent, it was suspended in ethyl acetate. The resulted suspension was filtered to give the product as a white solid (9 mg, 8%); $^1$H NMR (300 MHz) (DMSO-$d_6$) δ 11.57 (bs, 1H), 8.56 (bs, 3H), 7.73 (s, 1H), 7.35 (d, J=9 Hz, 1H), 7.20 (dd, J=8 Hz, J=2 Hz, 1H), 6.53 (s, 1H), 4.38-4.37 (m, 1H), 1.99-1.92 (m, 2H), 1.30-1.09 (m, 4H), 0.80 (t, J=7 Hz, 3H); LC/MS RT=2.74 (M–H$^-$: 279/281).

The requisite intermediate was prepared as follows:

Step 1)

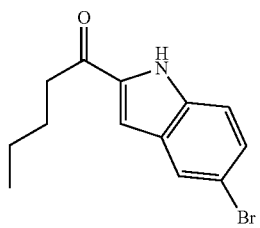 [SMILES: CCCCC(=O)c1cc2cc(Br)ccc2[nH]1]

1-(5-Bromo-1H-indol-2-yl)pentan-1-one

5-Bromo-N-methoxy-N-methyl-1H-indole-2-carboxamide (200 mg, 0.71 mmol) was dissolved in anhydrous tetrahydrofuran (15 mL). The mixture was cooled to −78° C., and, then, a solution of 2.5 M n-butyllithium in hexane (0.71 mL, 1.78 mmol) was added. The mixture was stirred for an hour at −78° C. The reaction was stopped by addition of water (10 mL). After removal of the solvent, the reaction mixture was diluted with ethyl acetate. The organic layer was washed with saturated $NH_4Cl$ and brine, and it was dried over $Na_2SO_4$. The organic layer was concentrated under reduced pressure. The residue was purified on an ISCO chromatograph (0-50% ethyl acetate/hexane) to give product as a white solid (167 mg, 84%); $^1$H NMR (300 MHz) (CDCl$_3$) δ 9.37 (bs, 1H), 7.84 (s, 1H), 7.42 (dd, J=9 Hz, J=1 Hz, 1H), 7.32 (d, J=9 Hz, 1H), 7.12 (s, 1H), 2.97-2.92 (m, 2H), 1.79-1.72 (m, 2H), 1.47-1.39 (m, 2H), 0.99-0.93 (m, 3H).

Example 3. Preparation of 1-(5-bromo-1H-indol-2-yl)-N-methylethan-1-amine

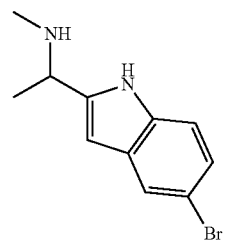

1-(5-Bromo-1H-indol-2-yl)-N-methylethan-1-amine

To a mixture of 1-(5-bromo-1H-indol-2-yl)ethan-1-one (50 mg, 0.21 mmol) in ethanol (5 mL), a solution of 2.0 M methylamine in tetrahydrofuran (1.05 mL, 2.10 mmol) was added. The mixture was treated with catalytic amount of acetic acid, and it was stirred for an hour at 60° C. Then, the mixture was treated with sodium cyanoborohydride (66 mg, 1.05 mmol), and it was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over $Na_2SO_4$. The organic layer was concentrated under reduced pressure, and the residue was purified on an ISCO chromatograph (0-10% methanol/dichloromethane+0.1% $NH_4OH$) to give the product as a colorless oil (53 mg, 100%); $^1$H NMR (300 MHz) (CDCl$_3$) δ 9.79 (bs, 1H), 7.67 (s, 1H), 7.27-7.26 (m, 2H), 6.41 (s, 1H), 4.35-4.32 (m, 1H), 2.43 (s, 3H), 1.71 (d, J=7 Hz, 3H); LC/MS RT=2.60 (M–H$^-$; 251/253).

Example 4. Preparation of 1-(1H-indol-2-yl)ethan-1-amine

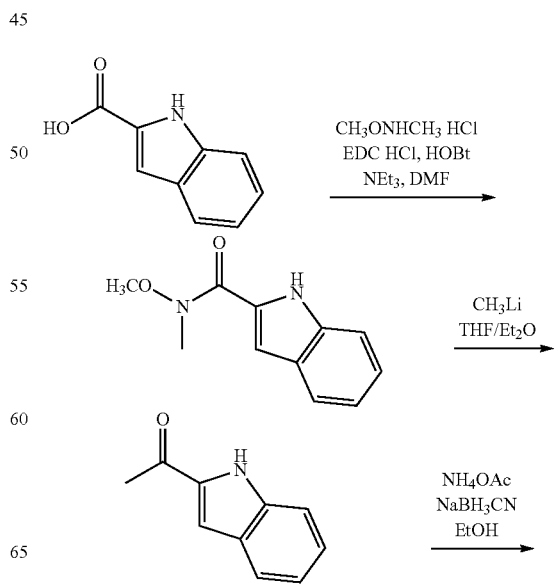

-continued

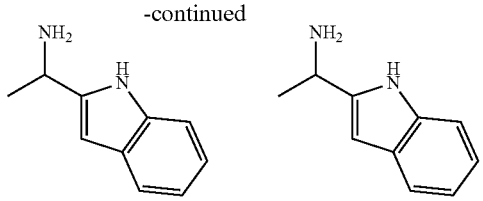

1-(1H-Indol-2-yl)ethan-1-amine 1-(1H-Indol-2-yl)ethan-1-one (100 mg, 0.63 mmol), ammonium acetate (486 mg, 6.30 mmol) and sodium cyanoborohydride (198 mg, 3.15 mmol) were dissolved in ethanol (10 mL). The mixture was stirred for overnight at 60° C. The reaction mixture was diluted with ethyl acetate. The organic layer was washed with 10% NaOH and brine, and it was dried over $Na_2SO_4$. The organic layer was concentrated under reduced pressure. The residue was purified on an ISCO chromatograph (100% dichloromethane followed by 10% methanol/dichloromethane+0.1% $NH_4OH$) to give the product as a colorless oil (85 mg, 84%); $^1$H NMR (300 MHz) ($CD_3OD$) δ 7.44 (d, J=8 Hz, 1H), 7.29 (d, J=8 Hz, 1H), 7.03 (t, J=8 Hz, 1H), 6.94 (t, J=7 Hz, 1H), 6.29 (s, 1H), 4.24-4.17 (m, 1H), 1.51 (d, J=7 Hz, 3H); LC/MS RT=2.19 (M–H⁻: 159).
The requisite intermediate was prepared as follows:
Step 1)

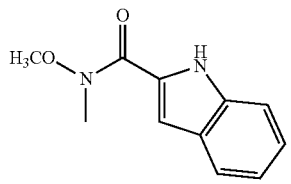

N-Methoxy-N-methyl-1H-indole-2-carboxamide

1H-Indole-2-carboxylic acid (1.0 g, 6.21 mmol), N,O-dimethylhydroxylamine hydrochloride (909 mg, 9.32 mmol), HOBt (839 mg, 6.21 mmol), EDC hydrochloride (2.5 g, 13.04 mmol) and triethylamine (3.46 mL, 24.84 mmol) were dissolved in anhydrous dimethylformamide (40 mL). The mixture was stirred for overnight at room temperature. The reaction mixture was diluted with ethyl acetate, and the organic layer was washed with water, saturated $NH_4Cl$, 10% NaOH and brine. The organic layer was dried over $Na_2SO_4$, and it was concentrated under reduced pressure. The residue was purified on an ISCO chromatograph (0-30% ethyl acetate/hexane) to give product as a white solid (450 mg, 35%); $^1$H NMR (300 MHz) ($CDCl_3$) δ 9.30 (bs, 1H), 7.70 (d, J=8 Hz, 1H), 7.44 (d, J=8 Hz, 1H), 7.31 (t, J=8 Hz, 1H), 7.25 (s, 1H), 7.14 (t, J=8 Hz, 1H), 3.85 (s, 3H), 3.44 (s, 3H).
Step 2)

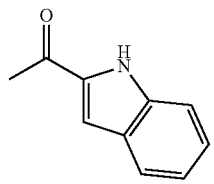

1-(1H-Indol-2-yl)ethan-1-one

N-Methoxy-N-methyl-1H-indole-2-carboxamide (450 mg, 2.20 mmol) was dissolved in anhydrous tetrahydrofuran (50 mL). The mixture was cooled to –78° C., and, then, a solution of 1.6 M methyllithium in diethyl ether (4.13 mL, 6.60 mmol) was added. The mixture was stirred for 2 hours at –78° C. An additional solution of 1.6 M methyllithium in diethyl ether (4.13 mL, 6.60 mmol) was added. The mixture was stirred for an hour at –78° C. The reaction was stopped by addition of water (10 mL). After removal of the solvent, the reaction mixture was diluted with ethyl acetate. The organic layer was washed with saturated $NH_4Cl$ and brine, and it was dried over $Na_2SO_4$. The organic layer was concentrated under reduced pressure. The residue was purified on an ISCO chromatograph (0-20% ethyl acetate/hexane) to give product as a white solid (290 mg, 83%); $^1$H NMR (300 MHz) ($CDCl_3$) δ 9.37 (bs, 1H), 7.72 (d, J=8 Hz, 1H), 7.45 (d, J=8 Hz, 1H), 7.38-7.33 (m, 1H), 7.22-7.14 (m, 2H), 2.62 (s, 3H).

Example 5. Preparation of 1-(5-bromo-1-methyl-1H-indol-2-yl)ethan-1-amine

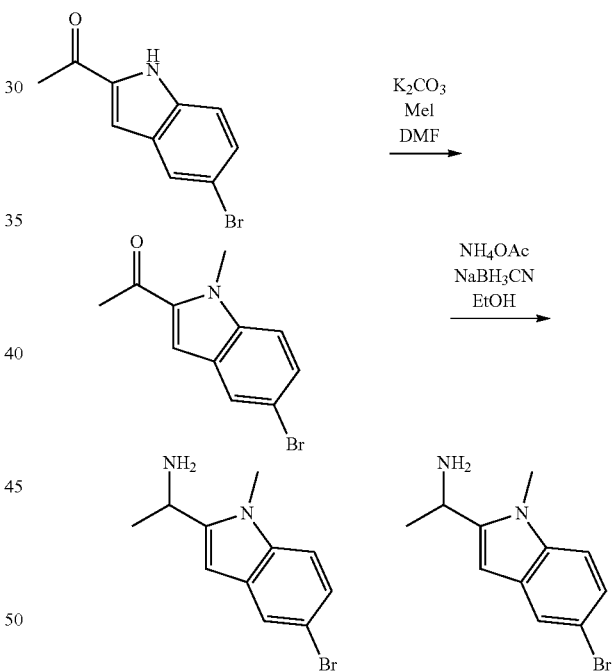

1-(5-Bromo-1-methyl-1H-indol-2-yl)ethan-1-amine 1-(5-Bromo-1-methyl-1H-indol-2-yl)ethan-1-one (91 mg, 0.36 mmol), ammonium acetate (277 mg, 3.60 mmol) and sodium cyanoborohydride (113 mg, 1.80 mmol) were dissolved in ethanol (10 mL). Then, catalytic amount of acetic acid was added. The mixture was stirred for overnight at 60° C. The reaction mixture was diluted with ethyl acetate. The organic layer was washed with 10% NaOH and brine, and it was dried over $Na_2SO_4$. The organic layer was concentrated under reduced pressure. The residue was purified on an ISCO chromatograph (0-10% methanol/dichloromethane+ 0.1% $NH_4OH$) to give the product as a white solid (57 mg, 63%); $^1$H NMR (300 MHz) (CD$_3$OD) δ 7.62 (d, J=2 Hz, 1H), 7.28 (d, J=9 Hz, 1H), 7.21 (dd, J=9 Hz, J=2 Hz, 1H), 6.44 (s, 1H), 4.44-4.38 (m, 1H), 3.75 (s, 3H), 1.56 (d, J=7 Hz, 3H); LC/MS RT=2.49 (M-NH$_2$$^+$: 236/238).

The requisite intermediate was prepared as follows:
Step 1)

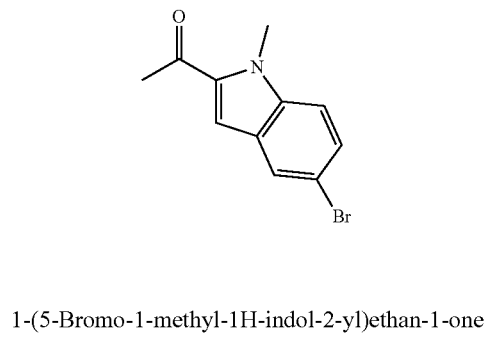

1-(5-Bromo-1-methyl-1H-indol-2-yl)ethan-1-one 1-(5-Bromo-1H-indol-2-yl)ethan-1-one (100 mg, 0.42 mmol), K$_2$CO$_3$ (116 mg, 0.84 mmol) and methyl iodide (52 µL, 0.84 mmol) were dissolved in anhydrous dimethylformamide (5 mL). The mixture was stirred for 3 hours at 60° C. After the mixture was cooled to room temperature, it was diluted with ethyl acetate. The organic layer was washed with water and brine, and it was concentrated under reduced pressure. The residue was purified on an ISCO chromatograph (0-50% ethyl acetate/hexane) to give product as a white solid (91 mg, 86%); $^1$H NMR (300 MHz) (CDCl$_3$) δ 7.82 (d, J=2 Hz, 1H), 7.45 (dd, J=9 Hz, J=2 Hz, 1H), 7.27 (d, J=9 Hz, 1H), 7.20 (s, 1H), 4.05 (s, 3H), 2.61 (s, 3H).

Example 6. Preparation of 1-(5-bromo-1H-indol-2-yl)ethane-1,2-diamine

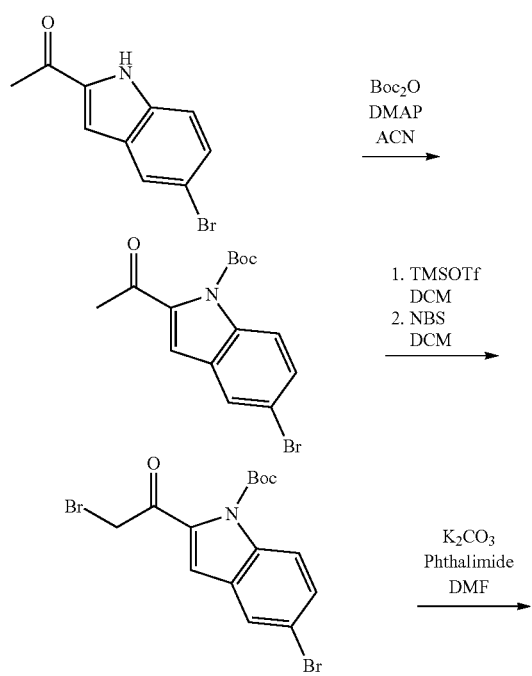

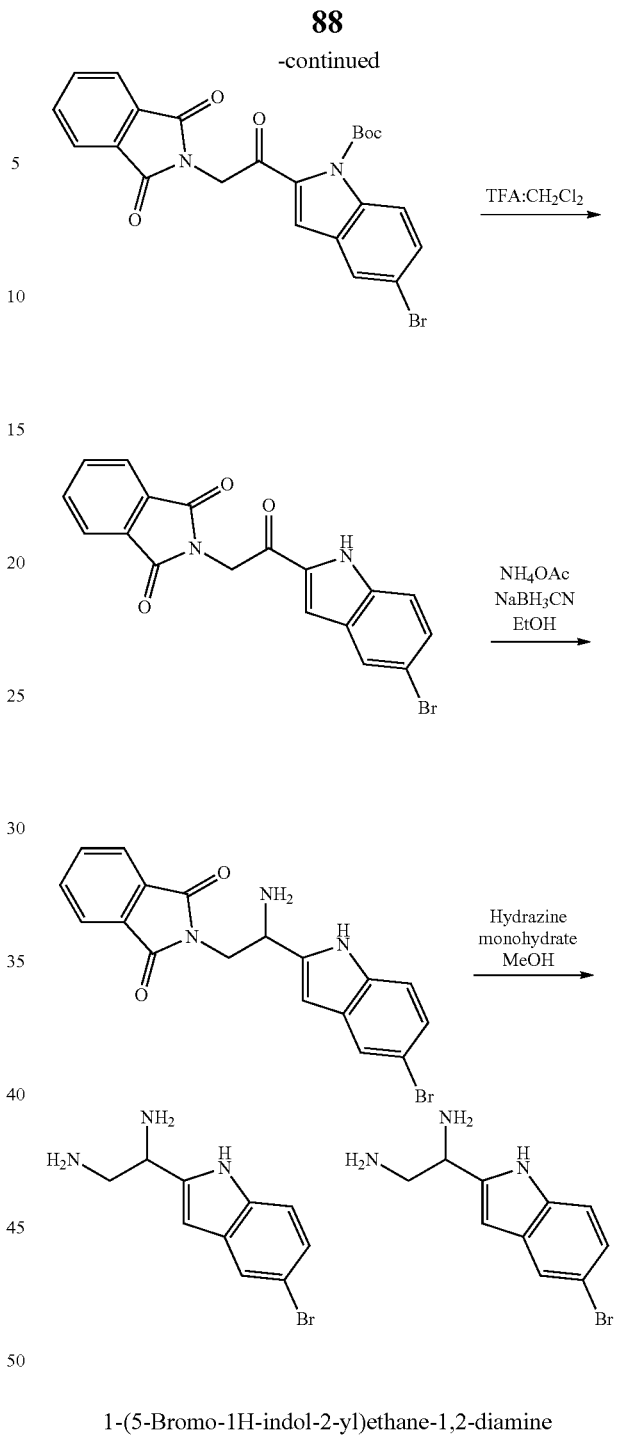

1-(5-Bromo-1H-indol-2-yl)ethane-1,2-diamine 2-(2-Amino-2-(5-bromo-1H-indol-2-yl)ethyl)isoindoline-1,3-dione (45 mg, 0.12 mmol) and hydrazine monohydrate were dissolved in methanol (5 mL), and it was stirred for overnight at room temperature. The mixture was then refluxed for an hour. The resulted suspension was filtered, and it was excessively washed with methanol. The filtrate was concentrated under reduced pressure, and it was purified on an ISCO chromatograph (0-10% methanol/dichloromethane+0.1% NH$_4$OH) to give product as a colorless oil (15 mg, 50%); $^1$H NMR (300 MHz) (CD$_3$OD) δ 7.61 (d, J=2 Hz, 1H), 7.24 (d, J=8 Hz, 1H), 7.15 (dd, J=8 Hz, J=2 Hz, 1H), 6.35 (s, 1H), 4.08-4.07 (m, 1H), 3.02 (d, J=6 Hz, 1H), 2.95 (d, J=7 Hz, 1H); LC/MS RT=2.05 (M–H$^−$: 252/254).

The requisite intermediate was prepared as follows:
Step 1)

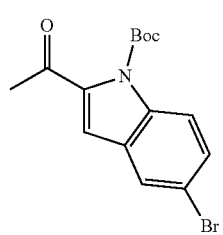 [SMILES: CC(=O)c1cc2cc(Br)ccc2n1C(=O)OC(C)(C)C]

t-Butyl 2-acetyl-5-bromo-1H-indole-1-carboxylate 1-(5-Bromo-1H-indol-2-yl)ethan-1-one (200 mg, 0.84 mmol), Boc anhydride (367 mg, 1.68 mmol) and DMAP (103 mg, 0.84 mmol) were dissolved in acetonitrile, and it was stirred for 3 hours at room temperature. The reaction mixture was diluted with ethyl acetate, and it was washed with saturated NH$_4$Cl and brine. The organic layer was dried over Na$_2$SO$_4$, and it was concentrated under reduced pressure. The residue was purified on an ISCO chromatograph (0-10% ethyl acetate/hexane) to give the product as a colorless oil (219 mg, 77%); $^1$H NMR (300 MHz) (CDCl$_3$) δ 7.93 (d, J=10 Hz, 1H), 7.75 (d, J=2 Hz, 1H), 7.50 (dd, J=9 Hz, J=2 Hz, 1H), 6.97 (s, 1H), 2.56 (s, 3H), 1.62 (s, 9H).

Step 2)

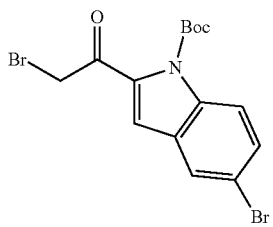 [SMILES: CC(C)(C)OC(=O)n1c(C(=O)CBr)cc2cc(Br)ccc21]

t-Butyl 5-bromo-2-(2-bromoacetyl)-1H-indole-1-carboxylate t-Butyl 2-acetyl-5-bromo-1H-indole-1-carboxylate (215 mg, 0.64 mmol), triethylamine (0.45 mL, 3.2 mmol) and trimethylsilyl trifluoromethanesulfonate (0.23 mL, 1.28 mmol) were dissolved in dichloromethane (10 mL), and it was stirred for an hour at 0° C. The reaction mixture was then diluted with ethyl acetate, and it was washed with saturated NaHCO$_3$ and brine. The organic layer was dried over Na$_2$SO$_4$, and it was concentrated under reduced pressure. The residue was dissolved in dichloromethane (10 mL), and N-bromosuccinimide (114 mg, 0.64) was added at 0° C. The mixture was stirred for an hour at the temperature. The reaction mixture was then diluted with ethyl acetate, and it was washed with saturated NaHCO$_3$ and brine. The organic layer was dried over Na$_2$SO$_4$, and it was concentrated under reduced pressure. The residue was purified on an ISCO chromatograph (0-10% ethyl acetate/hexane) to give the product as a colorless oil (169 mg, 63%); $^1$H NMR (300 MHz) (CDCl$_3$) δ 7.94 (d, J=9 Hz, 1H), 7.77 (d, J=2 Hz, 1H), 7.53 (dd, J=9 Hz, J=2 Hz, 1H), 7.03 (s, 1H), 4.35 (s, 2H), 1.62 (s, 9H).

Step 3)

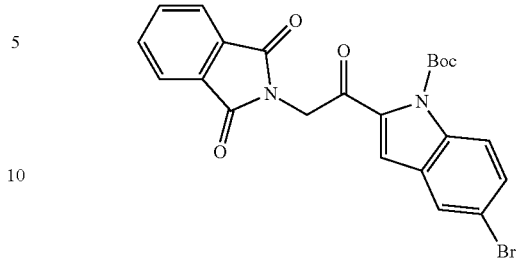

t-Butyl 5-bromo-2-(2-(1,3-dioxoisoindolin-2-yl)acetyl)-1H-indole-1-carboxylate

To a solution of phthalimide (63 mg, 0.43 mmol) and K$_2$CO$_3$ (62 mg, 0.45 mmol) in anhydrous dimethylformamide (10 mL), t-butyl 5-bromo-2-(2-bromoacetyl)-1H-indole-1-carboxylate (169 mg, 0.41 mmol) was added. The mixture was stirred for 2 hours at room temperature. The reaction mixture was then diluted with ethyl acetate, and it was washed with water and brine. The organic layer was dried over Na$_2$SO$_4$, and it was concentrated under reduced pressure. The residue was purified on an ISCO chromatograph (0-50% ethyl acetate/hexane) to give the product as a yellow oil (165 mg, 83%); $^1$H NMR (300 MHz) (CDCl$_3$) δ 7.99-7.95 (m, 1H), 7.92-7.87 (m, 2H), 7.79-7.73 (m, 3H), 7.52 (dd, J=9 Hz, J=2 Hz, 1H), 7.27 (s, 1H), 4.97 (s, 2H), 1.58 (s, 9H).

Step 4)

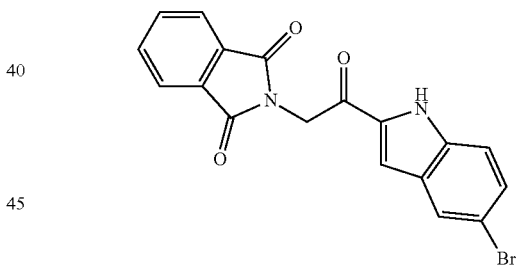

2-(2-(5-Bromo-1H-indol-2-yl)-2-oxoethyl)isoindoline-1,3-dione t-Butyl 5-bromo-2-(2-(1,3-dioxoisoindolin-2-yl)acetyl)-1H-indole-1-carboxylate (165 mg, 0.34 mmol) was dissolved in a mixture of trifluoracetic acid (1 mL) and dichloromethane (5 mL), and it was stirred for an hour at room temperature. After removal of solvent, it was diluted with ethyl acetate. The organic layer was washed with 10% NaOH and brine, and it was dried over Na$_2$SO$_4$. The organic layer was concentrated under reduced pressure, and the residue was purified on an ISCO chromatograph (0-100% ethyl acetate/hexane) to give the product as a white solid (130 mg, 100%); $^1$H NMR (300 MHz) (DMSO-d$_6$) δ 12.13 (bs, 1H), 7.97-7.88 (m, 7H), 7.62 (s, 1H), 5.16 (s, 2H).

Step 5)

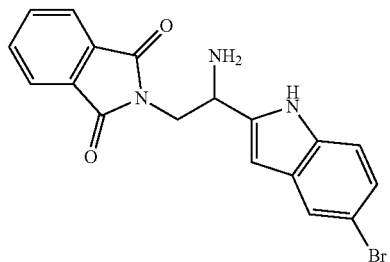 [SMILES: NC(CN1C(=O)c2ccccc2C1=O)c1cc2cc(Br)ccc2[nH]1]

2-(2-Amino-2-(5-bromo-1H-indol-2-yl)ethyl)isoindoline-1,3-dione 2-(2-(5-Bromo-1H-indol-2-yl)-2-oxoethyl)isoindoline-1,3-dione (130 mg, 0.34 mmol), ammonium acetate (262 mg, 3.40 mmol) and sodium cyanoborohydride (107 mg, 1.70 mmol) were dissolved in ethanol (10 mL). The mixture was stirred for overnight at 60° C. The reaction mixture was diluted with ethyl acetate. The organic layer was washed with 10% NaOH and brine, and it was dried over Na₂SO₄. The organic layer was concentrated under reduced pressure. The residue was purified on an ISCO chromatograph (0-10% methanol/dichloromethane+0.1% NH₄OH) to give the product as a yellow oil 50 mg, 38%); $^1$H NMR (300 MHz) (CDCl₃) δ 7.91 (bs, 1H), 7.82-7.79 (m, 2H), 7.72-7.69 (m, 2H), 7.62 (s, 1H), 7.26-7.22 (m, 2H), 6.43 (s, 1H), 4.73-4.69 (m, 1H), 4.13-4.03 (m, 2H).

Example 7. Preparation of 1-(5-fluoro-1H-indol-2-yl)ethan-1-amine

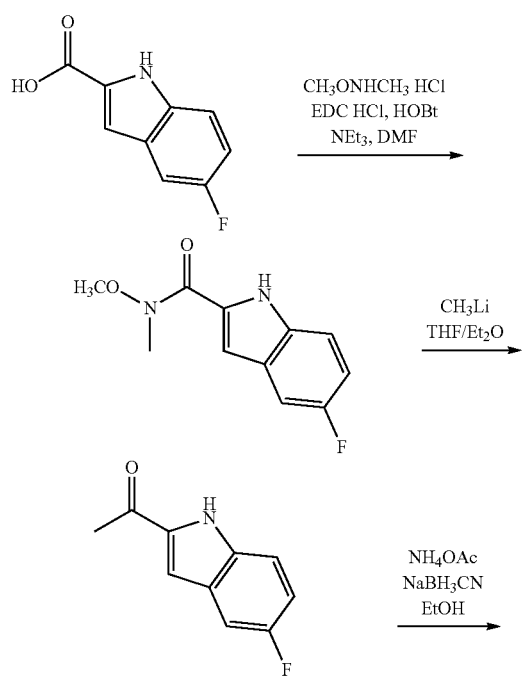

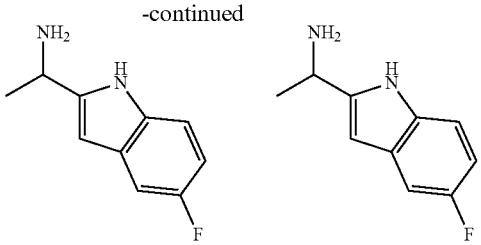

1-(5-Fluoro-1H-indol-2-yl)ethan-1-amine 1-(5-Fluoro-1H-indol-2-yl)ethan-1-one (100 mg, 0.56 mmol), ammonium acetate (432 mg, 5.60 mmol) and sodium cyanoborohydride (176 mg, 2.80 mmol) were dissolved in ethanol (10 mL). The mixture was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over Na₂SO₄. The organic layer was concentrated under reduced pressure, and the residue was purified on an ISCO chromatograph (0-10% methanol/dichloromethane+0.1% NH₄OH) to give the product as a white solid (61 mg, 60%); $^1$H NMR (300 MHz) (CD₃OD) δ 7.25-7.21 (m, 1H), 7.10 (d, J=8 Hz, 1H), 6.79 (t, J=8 Hz, 1H), 6.28 (s, 1H), 4.22-4.17 (m, 1H), 1.49 (d, J=6 Hz, 3H); LC/MS RT=2.33 (M−H⁻: 177).

The requisite intermediate was prepared as follows:

Step 1)

5-Fluoro-N-methoxy-N-methyl-1H-indole-2-carboxamide

5-Fluoro-1H-indole-2-carboxylic acid (1.0 g, 5.58 mmol), N,O-dimethylhydroxylamine hydrochloride (816 mg, 8.37 mmol), HOBt (754 mg, 5.58 mmol), EDC hydrochloride (2.25 g, 11.7 mmol) and triethylamine (3.11 mL, 22.3 mmol) were dissolved in anhydrous dimethylformamide (50 mL). The mixture was stirred for overnight at room temperature. The reaction mixture was diluted with ethyl acetate, and the organic layer was washed with water, saturated NH₄Cl, 10% NaOH and brine. The organic layer was dried over Na₂SO₄, and it was concentrated under reduced pressure. The residue was purified on an ISCO chromatograph (0-50% ethyl acetate/hexane) to give product as a white solid (770 mg, 62%); $^1$H NMR (300 MHz) (CDCl₃) δ 9.94 (bs, 1H), 7.41-7.36 (m, 1H), 7.32 (dd, J=9 Hz, J=2 Hz, 1H), 7.19 (s, 1H), 7.06 (td, J=9 Hz, J=3 Hz, 1H), 3.85 (s, 3H), 3.46 (s, 3H).

Step 2)

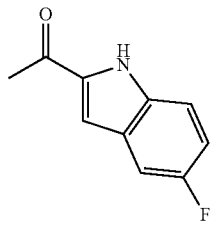

1-(5-Fluoro-1H-indol-2-yl)ethan-1-one

5-Fluoro-N-methoxy-N-methyl-1H-indole-2-carboxamide (300 mg, 1.35 mmol) was dissolved in anhydrous tetrahydrofuran (25 mL). The mixture was cooled to −78° C., and, then, a solution of 1.6 M methyllithium in diethyl ether (2.53 mL, 4.05 mmol) was added. The mixture was stirred for 2 hours at −78° C. The reaction was stopped by addition of water (10 mL). After removal of the solvent, the reaction mixture was diluted with ethyl acetate. The organic layer was washed with saturated $NH_4Cl$ and brine, and it was dried over $Na_2SO_4$. The organic layer was concentrated under reduced pressure. The residue was purified on an ISCO chromatograph (0-20% ethyl acetate/hexane) to give product as a white solid (220 mg, 92%); $^1$H NMR (300 MHz) (CDCl$_3$) δ 9.18 (bs, 1H), 7.39-7.32 (m, 2H), 7.16-7.08 (m, 2H), 2.60 (s, 3H).

Example 8. Preparation of 1-(5-methoxy-1H-indol-2-yl)ethan-1-amine

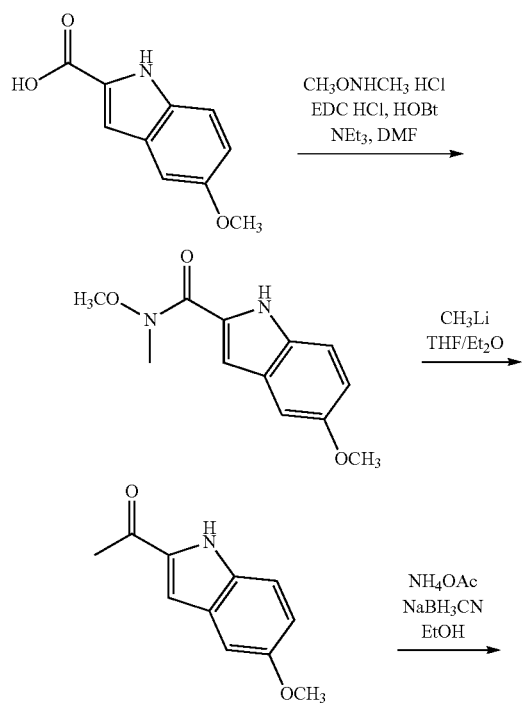

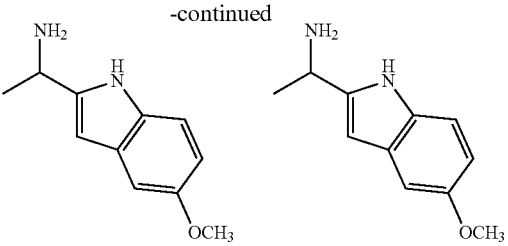

1-(5-Methoxy-1H-indol-2-yl)ethan-1-amine 1-(5-Methoxy-1H-indol-2-yl)ethan-1-one (100 mg, 0.42 mmol), ammonium acetate (324 mg, 4.20 mmol) and sodium cyanoborohydride (132 mg, 2.10 mmol) were dissolved in ethanol (10 mL). The mixture was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over $Na_2SO_4$. The organic layer was concentrated under reduced pressure, and the residue was purified on an ISCO chromatograph (0-10% methanol/dichloromethane+0.1% $NH_4OH$) to give the product as a white solid (58 mg, 58%); $^1$H NMR (300 MHz) (DMSO-d$_6$) δ 10.66 (bs, 1H), 7.15 (d, J=9 Hz, 1H), 6.90 (d, J=2 Hz, 1H), 6.61 (dd, J=9 Hz, J=2 Hz, 1H), 6.09 (s, 1H), 4.08-4.02 (m, 1H), 3.69 (s, 3H), 1.33 (d, J=6 Hz, 3H); LC/MS RT=2.17 (M−H$^-$: 189).

The requisite intermediate was prepared as follows:

Step 1)

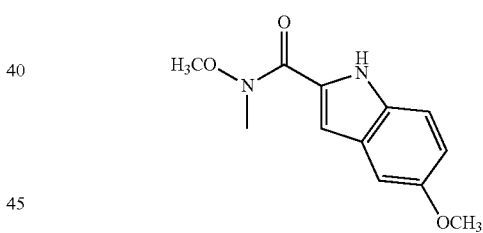

N,5-Dimethoxy-N-methyl-1H-indole-2-carboxamide

5-Methoxy-1H-indole-2-carboxylic acid (1.0 g, 5.23 mmol), N, O-dimethylhydroxylamine hydrochloride (766 mg, 7.85 mmol), HOBt (707 mg, 5.23 mmol), EDC hydrochloride (2.10 g, 10.98 mmol) and triethylamine (2.92 mL, 20.92 mmol) were dissolved in anhydrous dimethylformamide (50 mL). The mixture was stirred for overnight at room temperature. The reaction mixture was diluted with ethyl acetate, and the organic layer was washed with water, saturated $NH_4Cl$, 10% NaOH and brine. The organic layer was dried over $Na_2SO_4$, and it was concentrated under reduced pressure. The residue was purified on an ISCO chromatograph (0-50% ethyl acetate/hexane) to give product as a white solid (743 mg, 60%); $^1$H NMR (300 MHz) (CDCl$_3$) δ 9.78 (bs, 1H), 7.35 (d, J=9 Hz, 1H), 7.17 (s, 1H), 7.1 (d, J=2 Hz, 1H), 6.98 (dd, J=9 Hz, J=2 Hz, 1H), 3.85 (s, 3H), 3.84 (s, 3H), 3.46 (s, 3H).

Step 2)

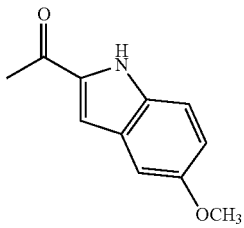

1-(5-Methoxy-1H-indol-2-yl)ethan-1-one

N,5-Dimethoxy-N-methyl-1H-indole-2-carboxamide (300 mg, 1.28 mmol) was dissolved in anhydrous tetrahydrofuran (20 mL). The mixture was cooled to −78° C., and, then, a solution of 1.6 M methyllithium in diethyl ether (2.40 mL, 3.84 mmol) was added. The mixture was stirred for 2 hours at −78° C. The reaction was stopped by addition of water (10 mL). After removal of the solvent, the reaction mixture was diluted with ethyl acetate. The organic layer was washed with saturated NH$_4$Cl and brine, and it was dried over Na$_2$SO$_4$. The organic layer was concentrated under reduced pressure. The residue was purified on an ISCO chromatograph (0-20% ethyl acetate/hexane) to give product as a white solid (180 mg, 74%); $^1$H NMR (300 MHz) (CDCl$_3$) δ 8.91 (bs, 1H), 7.31 (d, J=9 Hz, 1H), 7.12-7.08 (m, 2H), 7.03 (dd, J=9 Hz, J=3 Hz, 1H), 3.85 (s, 3H), 2.58 (s, 3H).

Example 9. Preparation of 1-(5-(trifluoromethyl)-1H-indol-2-yl)ethan-1-amine

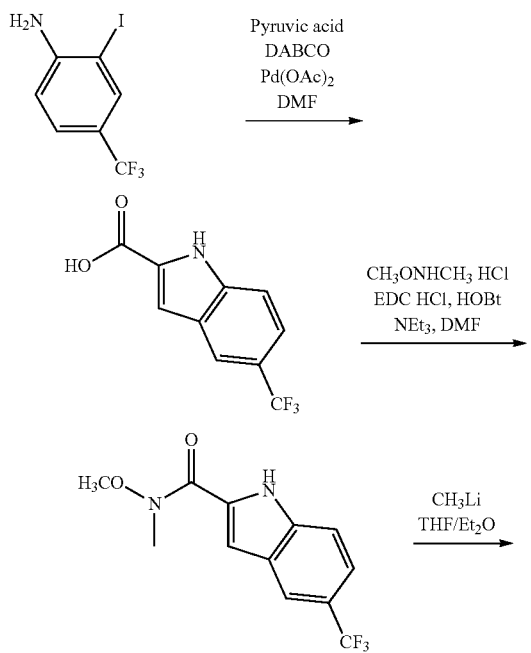

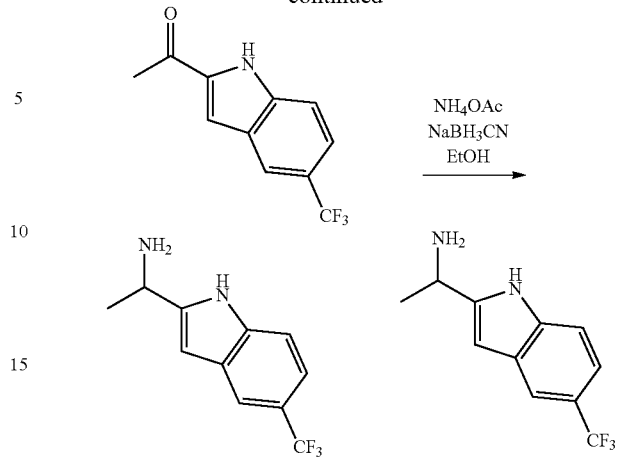

1-(5-(Trifluoromethyl)-1H-indol-2-yl)ethan-1-amine 1-(5-Trifluoromethyl-1H-indol-2-yl)ethan-1-one (100 mg, 0.44 mmol), ammonium acetate (339 mg, 4.40 mmol) and sodium cyanoborohydride (138 mg, 2.20 mmol) were dissolved in ethanol (10 mL). The mixture was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over Na$_2$SO$_4$. The organic layer was concentrated under reduced pressure, and the residue was purified on an ISCO chromatograph (0-10% methanol/dichloromethane+0.1% NH$_4$OH) to give the product as a white solid (42 mg, 42%); $^1$H NMR (300 MHz) (DMSO-d$_6$) δ 11.34 (bs, 1H), 7.79 (s, 1H), 7.46 (d, J=9 Hz, 1H), 7.27 (d, J=8 Hz, 1H), 6.36 (s, 1H), 4.15-4.09 (m, 1H), 1.37 (d, J=6 Hz, 3H); LC/MS RT=2.50 (M−H$^−$: 227).

The requisite intermediate was prepared as follows:
Step 1)

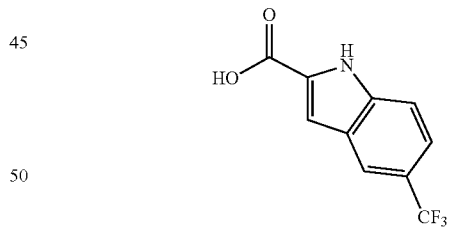

5-(Trifluoromethyl)-1H-indole-2-carboxylicacid

2-Iodo-4-(trifluoromethyl)aniline (1.0 g, 3.48 mmol), pyruvic acid (0.74 mL, 10.44 mmol), DABCO (1.17 g, 10.44 mmol) and Pd(OAc)$_2$ (79 mg, 0.35 mmol) were dissolved in anhydrous dimethylformamide (10 mL). The mixture was purged with nitrogen, and it was stirred for 4 hours at 110° C. The reaction mixture was diluted with ethyl acetate, and the organic layer was washed with 1N HCl and brine. The organic layer was dried over Na$_2$SO$_4$, and it was concentrated under reduced pressure. The residue was purified on an ISCO chromatograph (0-50% ethyl acetate/hexane) to give product as a beige solid (484 mg, 54%); $^1$H NMR (300

MHz) (CD₃OD) δ 11.66 (bs, 1H), 7.98 (s, 1H), 7.57 (d, J=9 Hz, 1H), 7.47 (d, J=9 Hz, 1H), 7.26 (s, 1H).

Step 2)

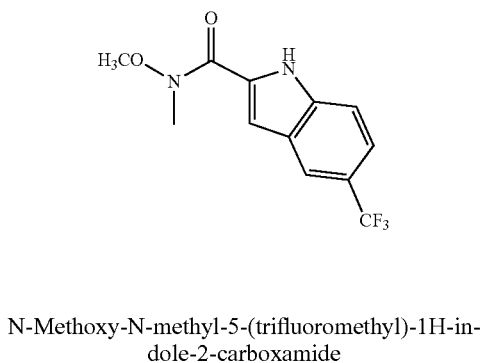

N-Methoxy-N-methyl-5-(trifluoromethyl)-1H-indole-2-carboxamide 5-(Trifluoromethyl)-1H-indole-2-carboxylic acid (484 mg, 2.11 mmol), N,O-dimethylhydroxylamine hydrochloride (309 mg, 3.17 mmol), HOBt (285 mg, 2.11 mmol), EDC hydrochloride (849 mg, 4.43 mmol) and triethylamine (1.18 mL, 8.44 mmol) were dissolved in anhydrous dimethylformamide (50 mL). The mixture was stirred for overnight at room temperature. The reaction mixture was diluted with ethyl acetate, and the organic layer was washed with water, saturated NH₄Cl, 10% NaOH and brine. The organic layer was dried over Na₂SO₄, and it was concentrated under reduced pressure. The residue was purified on an ISCO chromatograph (0-50% ethyl acetate/hexane) to give product as a white solid (402 mg, 70%); ¹H NMR (300 MHz) (CDCl₃) δ 9.97 (bs, 1H), 8.01 (s, 1H), 7.53 (m, 2H), 7.32 (s, 1H), 3.86 (s, 3H), 3.45 (s, 3H).

Step 3)

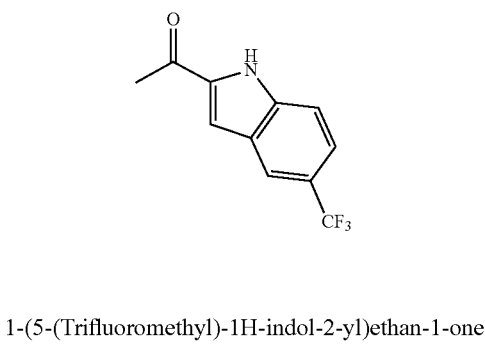

1-(5-(Trifluoromethyl)-1H-indol-2-yl)ethan-1-one

N-Methoxy-N-methyl-5-(trifluoromethyl)-1H-indole-2-carboxamide (300 mg, 1.10 mmol) was dissolved in anhydrous tetrahydrofuran (20 mL). The mixture was cooled to −78° C., and, then, a solution of 1.6 M methyllithium in diethyl ether (2.06 mL, 3.30 mmol) was added. The mixture was stirred for 2 hours at −78° C. The reaction was stopped by addition of water (10 mL). After removal of the solvent, the reaction mixture was diluted with ethyl acetate. The organic layer was washed with saturated NH₄Cl and brine, and it was dried over Na₂SO₄. The organic layer was concentrated under reduced pressure. The residue was purified on an ISCO chromatograph (0-20% ethyl acetate/hexane) to give product as a white solid (197 mg, 80%); ¹H NMR (300 MHz) (CDCl₃) δ 9.40 (bs, 1H), 8.03 (s, 1H), 7.59-7.51 (m, 2H), 7.28 (s, 1H), 2.64 (s, 3H).

Example 10. Preparation of 1-(6-bromo-1H-indol-2-yl)ethan-1-amine

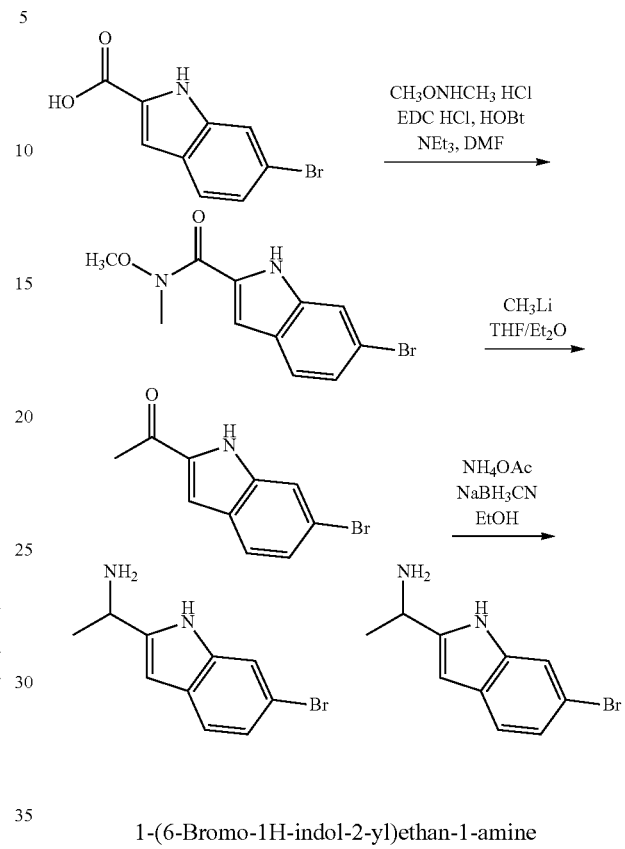

1-(6-Bromo-1H-indol-2-yl)ethan-1-amine 1-(6-Bromo-1H-indol-2-yl)ethan-1-one (100 mg, 0.42 mmol), ammonium acetate (324 mg, 4.20 mmol) and sodium cyanoborohydride (132 mg, 2.10 mmol) were dissolved in ethanol (10 mL). The mixture was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over Na₂SO₄. The organic layer was concentrated under reduced pressure, and the residue was purified on an ISCO chromatograph (0-10% methanol/dichloromethane+0.1% NH₄OH) to give the product as a white solid (58 mg, 58%); ¹H NMR (300 MHz) (DMSO-d₆) δ 11.39 (bs, 1H), 8.43 (bs, 2H), 7.58 (s, 1H), 7.49 (d, J=8 Hz, 1H), 7.13 (dd, J=9 Hz, J=2 Hz, 1H), 6.51 (s, 1H), 4.57-4.55 (m, 1H), 1.59 (d, J=7 Hz, 3H); LC/MS RT=2.43 (M−H⁻: 237/239).

The requisite intermediate was prepared as follows:

Step 1)

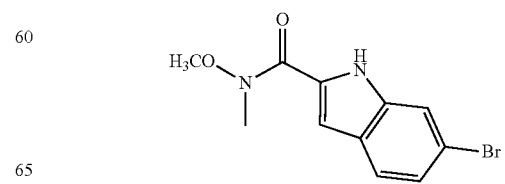

6-Bromo-N-methoxy-N-methyl-1H-indole-2-carboxamide

6-Bromo-1H-indole-2-carboxylic acid (1.0 g, 4.17 mmol), N, O-dimethylhydroxylamine hydrochloride (611 mg, 6.26 mmol), HOBt (563 mg, 4.17 mmol), EDC hydrochloride (1.68 g, 8.76 mmol) and triethylamine (2.32 mL, 16.68 mmol) were dissolved in anhydrous dimethylformamide (50 mL). The mixture was stirred for overnight at room temperature. The reaction mixture was diluted with ethyl acetate, and the organic layer was washed with water, saturated NH$_4$Cl, 10% NaOH and brine. The organic layer was dried over Na$_2$SO$_4$, and it was concentrated under reduced pressure. The residue was purified on an ISCO chromatograph (0-50% ethyl acetate/hexane) to give product as a white solid (327 mg, 28%); $^1$H NMR (300 MHz) (CDCl$_3$) δ 9.62 (bs, 1H), 7.61 (s, 1H), 7.55 (d, J=9 Hz, 1H), 7.26-7.19 (m, 2H), 3.85 (s, 3H), 3.45 (s, 3H).

Step 2)

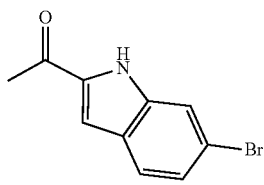

1-(6-Bromo-1H-indol-2-yl)ethan-1-one

6-Bromo-N-methoxy-N-methyl-1H-indole-2-carboxamide (327 mg, 1.15 mmol) was dissolved in anhydrous tetrahydrofuran (20 mL). The mixture was cooled to −78° C., and, then, a solution of 1.6 M methyllithium in diethyl ether (2.16 mL, 3.45 mmol) was added. The mixture was stirred for 2 hours at −78° C. The reaction was stopped by addition of water (10 mL). After removal of the solvent, the reaction mixture was diluted with ethyl acetate. The organic layer was washed with saturated NH$_4$Cl and brine, and it was dried over Na$_2$SO$_4$. The organic layer was concentrated under reduced pressure. The residue was purified on an ISCO chromatograph (0-20% ethyl acetate/hexane) to give product as a white solid (197 mg, 72%); $^1$H NMR (300 MHz) (CDCl$_3$) δ 9.12 (bs, 1H), 7.60-7.56 (m, 2H), 7.27-7.34 (m, 1H), 7.16 (s, 1H), 2.59 (s, 3H).

Example 11. Preparation of 1-(5-(trifluoromethoxy)-1H-indol-2-yl)ethan-1-amine

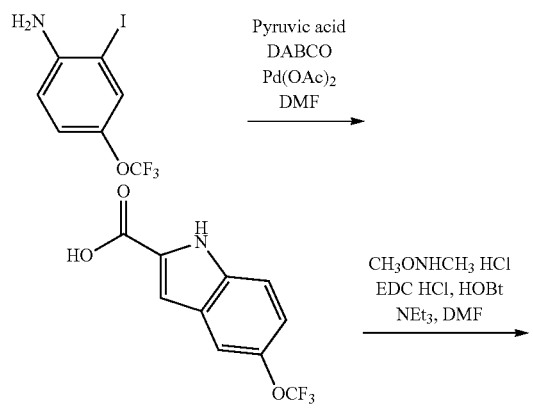

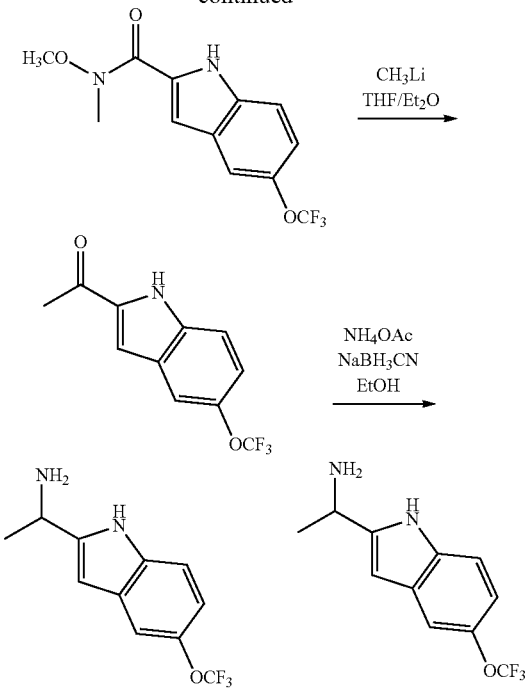

1-(5-(Trifluoromethoxy)-1H-indol-2-yl)ethan-1-amine 1-(5-(Trifluoromethoxy)-1H-indol-2-yl)ethan-1-one (100 mg, 0.41 mmol), ammonium acetate (316 mg, 4.10 mmol) and sodium cyanoborohydride (129 mg, 2.05 mmol) were dissolved in ethanol (10 mL). The mixture was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over Na$_2$SO$_4$. The organic layer was concentrated under reduced pressure, and the residue was purified on an ISCO chromatograph (0-10% methanol/dichloromethane+0.1% NH$_4$OH) to give the product as a white solid (48 mg, 48%); $^1$H NMR (300 MHz) (DMSO-d$_6$) δ 11.15 (bs, 1H), 7.38 (s, 1H), 7.35 (d, J=9 Hz, 1H), 6.94 (d, J=8 Hz, 1H), 6.27 (s. 1H), 4.14-4.07 (m, 1H), 1.36 (d, J=7 Hz, 3H); LC/MS RT=2.55 (M−H$^−$: 243).

The requisite intermediate was prepared as follows:

Step 1)

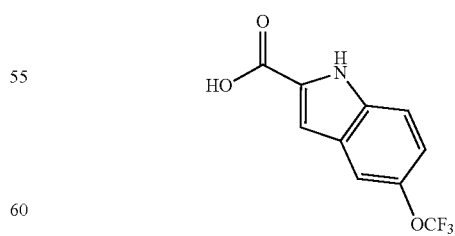

5-(Trifluoromethoxy)-1H-indole-2-carboxylic acid

2-Iodo-4-(trifluoromethoxy)aniline (1.0 g, 3.30 mmol), pyruvic acid (0.70 mL, 9.90 mmol), DABCO (1.11 g, 9.90 mmol) and Pd(OAc)$_2$ (74 mg, 0.33 mmol) were dissolved in anhydrous dimethylformamide (10 mL). The mixture was purged with nitrogen, and it was stirred for 4 hours at 110° C. The reaction mixture was diluted with ethyl acetate, and the organic layer was washed with 1N HCl and brine. The organic layer was dried over Na$_2$SO$_4$, and it was concentrated under reduced pressure. The residue was purified on an ISCO chromatograph (0-50% ethyl acetate/hexane) to give product as a beige solid (592 mg, 73%); $^1$H NMR (300 MHz) (DMSO-d$_6$) δ 12.02 (bs, 1H), 7.64 (s, 1H), 7.49 (d, J=9 Hz, 1H), 7.20 (d, J=6 Hz, 1H), 7.13 (s, 1H).
Step 2)

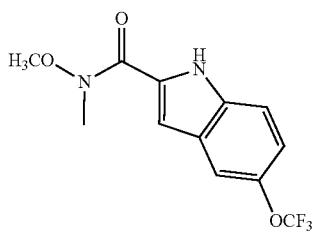 [SMILES: CON(C)C(=O)c1cc2cc(OC(F)(F)F)ccc2[nH]1]

N-Methoxy-N-methyl-5-(trifluoromethoxy)-1H-indole-2-carboxamide 5-(Trifluoromethoxy)-1H-indole-2-carboxylic acid (592 mg, 2.41 mmol), N, O-dimethylhydroxylamine hydrochloride (353 mg, 3.62 mmol), HOBt (326 mg, 2.41 mmol), EDC hydrochloride (970 mg, 5.06 mmol) and triethylamine (1.18 mL, 8.44 mmol) were dissolved in anhydrous dimethylformamide (50 mL). The mixture was stirred for overnight at room temperature. The reaction mixture was diluted with ethyl acetate, and the organic layer was washed with water, saturated NH$_4$Cl, 10% NaOH and brine. The organic layer was dried over Na$_2$SO$_4$, and it was concentrated under reduced pressure. The residue was purified on an ISCO chromatograph (0-70% ethyl acetate/hexane) to give product as a white solid (378 mg, 54%); $^1$H NMR (300 MHz) (CDCl$_3$) δ 9.33 (bs, 1H), 7.55 (s, 1H), 7.42 (d, J=9 Hz, 1H), 7.24 (s, 1H), 7.18 (d, J=9 Hz, 1H), 3.85 (s, 3H), 3.44 (s, 3H).
Step 3)

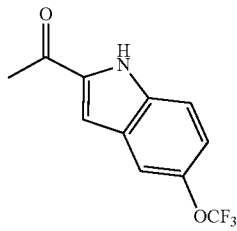 [SMILES: CC(=O)c1cc2cc(OC(F)(F)F)ccc2[nH]1]

1-(5-(Trifluoromethoxy)-1H-indol-2-yl)ethan-1-one

N-Methoxy-N-methyl-5-(trifluoromethoxy)-1H-indole-2-carboxamide (378 mg, 1.31 mmol) was dissolved in anhydrous tetrahydrofuran (20 mL). The mixture was cooled to −78° C., and, then, a solution of 1.6 M methyllithium in diethyl ether (2.46 mL, 3.93 mmol) was added. The mixture was stirred for 2 hours at −78° C. The reaction was stopped by addition of water (10 mL). After removal of the solvent, the reaction mixture was diluted with ethyl acetate. The organic layer was washed with saturated NH$_4$Cl and brine, and it was dried over Na$_2$SO$_4$. The organic layer was concentrated under reduced pressure. The residue was purified on an ISCO chromatograph (0-20% ethyl acetate/hexane) to give product as a white solid (259 mg, 81%); $^1$H NMR (300 MHz) (CDCl$_3$) δ 9.35 (bs, 1H), 7.57 (s, 1H), 7.44 (d, J=9 Hz, 1H), 7.26-7.20 (m, 2H), 2.62 (s, 3H).

Example 12. Preparation of 1-(1H-indol-2-yl)-N,N-dimethylethan-1-amine

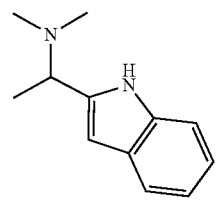

1-(1H-Indol-2-yl)-N,N-dimethylethan-1-amine 1-(5-Bromo-1H-indol-2-yl)-N-methylethan-1-amine (53 mg, 0.21 mmol) and Boc anhydride (92 mg, 0.42 mmol) were dissolved in anhydrous tetrahydrofuran (10 mL), and it was stirred overnight at room temperature. The reaction mixture was diluted with ethyl acetate, and it was washed with water and brine. The organic layer was dried over Na$_2$SO$_4$, and it was concentrated under reduced pressure. The crude material was dissolved in anhydrous tetrahydrofuran (10 mL), and lithium aluminum hydride (24 mg, 0.63 mmol) was added. The mixture was stirred for an hour at 50° C. The reaction was stopped by addition of saturated sodium sulfate (1 mL), and the resulted suspension was filtered. The filtrate was purified on an ISCO chromatograph (0-10% methanol/dichloromethane+0.1% NH$_4$OH) to give the product as a white solid (6 mg, 15%); LC/MS RT=2.46 (M+H$^+$: 189).

Example 13. Preparation of (6-bromo-1H-indol-2-yl)methanamine

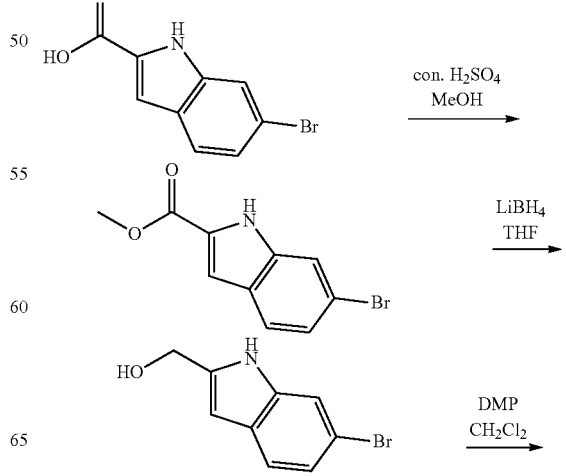

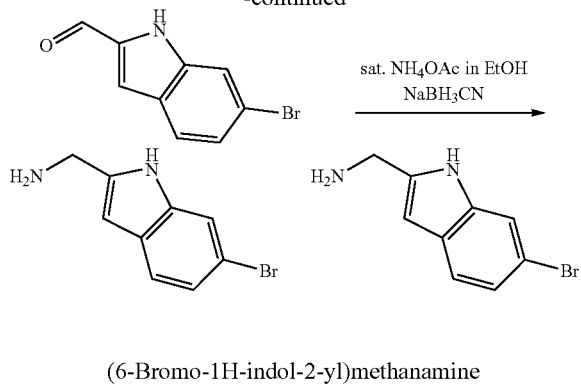

(6-Bromo-1H-indol-2-yl)methanamine

6-Bromo-1H-indole-2-carbaldehyde (51 mg, 0.23 mmol) was dissolved in a solution of saturated ammonium acetate in ethanol (20 mL), and, then, it was treated with sodium cyanoborohydride (43 mg, 0.69 mmol). The mixture was stirred for overnight at room temperature. The reaction mixture was diluted with ethyl acetate, and it was washed with saturated water and brine. The organic layer was dried over $Na_2SO_4$, and it was concentrated under reduced pressure. The residue was purified on an ISCO chromatograph (0-10% methanol/dichloromethane+0.1% $NH_4OH$) to give product as a colorless oil (7 mg, 13%); $^1H$ NMR (300 MHz) (DMSO-$d_6$) δ 11.12 (bs, 1H), 7.54 (s, 1H), 7.43 (d, J=8 Hz, 1H), 7.07 (d, J=9 Hz, 1H), 6.37 (s, 1H), 3.97 (s, 2H); LC/MS RT=2.52 (M–H$^-$: 223/225).

The requisite intermediate was prepared as follows:
Step 1)

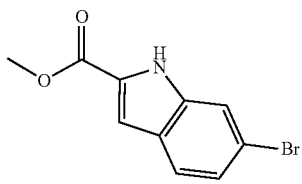

Methyl 6-bromo-1H-indole-2-carboxylate

6-Bromo-1H-indole-2-carboxylic acid (1.0 g, 4.17 mmol) was dissolved in methanol (100 mL), and it was treated with catalytic amount of concentrated sulfuric acid. The mixture was refluxed overnight. After removal of solvent, it was diluted with ethyl acetate. The organic layer was washed with 10% NaOH and brine, and it was dried over $Na_2SO_4$. The organic layer was concentrated under reduced pressure, and the residue was purified on an ISCO chromatograph (0-50% ethyl acetate/hexane) to give product as a pink solid (612 mg, 58%); $^1H$ NMR (300 MHz) (CDCl$_3$) δ 9.01 (bs, 1H), 7.59 (s, 1H), 7.55 (d, J=9 Hz, 1H), 7.28-7.24 (m, 1H), 7.19 (s, 1H), 3.96 (s, 3H).
Step 2)

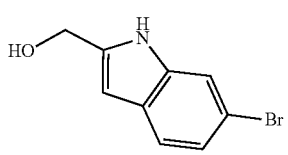 [SMILES: OCc1cc2ccc(Br)cc2[nH]1]

(6-Bromo-1H-indol-2-yl)methanol

Methyl 6-bromo-1H-indole-2-carboxylate (200 mg, 0.79 mmol) and lithium borohydride (86 mg, 3.95 mmol) were dissolved in anhydrous tetrahydrofuran (10 mL) at 0° C., and it was stirred for overnight at room temperature. The reaction mixture was diluted with ethyl acetate, and it was washed with saturated $NH_4Cl$ and brine. The organic layer was dried over $Na_2SO_4$, and it was concentrated under reduced pressure. The residue was purified on an ISCO chromatograph (0-50% ethyl acetate/hexane) to give product as a white solid (162 mg, 91%); $^1H$ NMR (300 MHz) (CDCl$_3$) δ 8.42 (bs, 1H), 7.47 (s, 1H), 7.42 (d, J=8 Hz, 1H), 7.20 (dd, J=10 Hz, J=2 Hz, 1H), 6.36 (d, J=1 Hz, 1H), 4.80 (s, 2H).
Step 3)

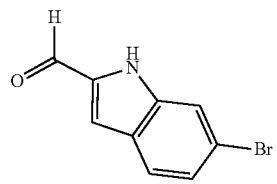 [SMILES: O=Cc1cc2ccc(Br)cc2[nH]1]

6-Bromo-1H-indole-2-carbaldehyde (6-Bromo-1H-indol-2-yl)methanol (80 mg, 0.35 mmol) and dess-martin periodinane (178 mg, 0.42 mmol) were dissolved in dichloromethane (10 mL), and it was stirred for 30 minutes at room temperature. The reaction mixture was diluted with ethyl acetate, and it was washed with 10% sodium thiosulfate, saturated $NaHCO_3$ and brine. The organic layer was dried over $Na_2SO_4$, and it was concentrated under reduced pressure. The residue was purified on an ISCO chromatograph (0-10% ethyl acetate/hexane) to give product as a white solid (78 mg, 100%); $^1H$ NMR (300 MHz) (CDCl$_3$) δ 9.86 (s, 1H), 9.23 (bs, 1H), 7.65 (s, 1H), 7.61 (d, J=9 Hz, 1H), 7.29 (d, J=9 Hz, 1H), 7.26-7.25 (m, 1H).

Example 14. Preparation of (5-bromo-1H-indol-2-yl)methanamine

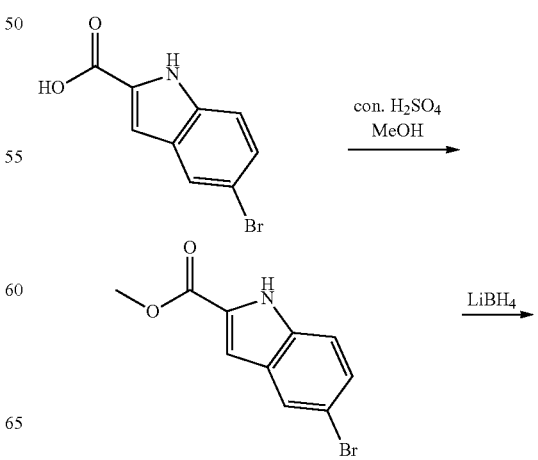

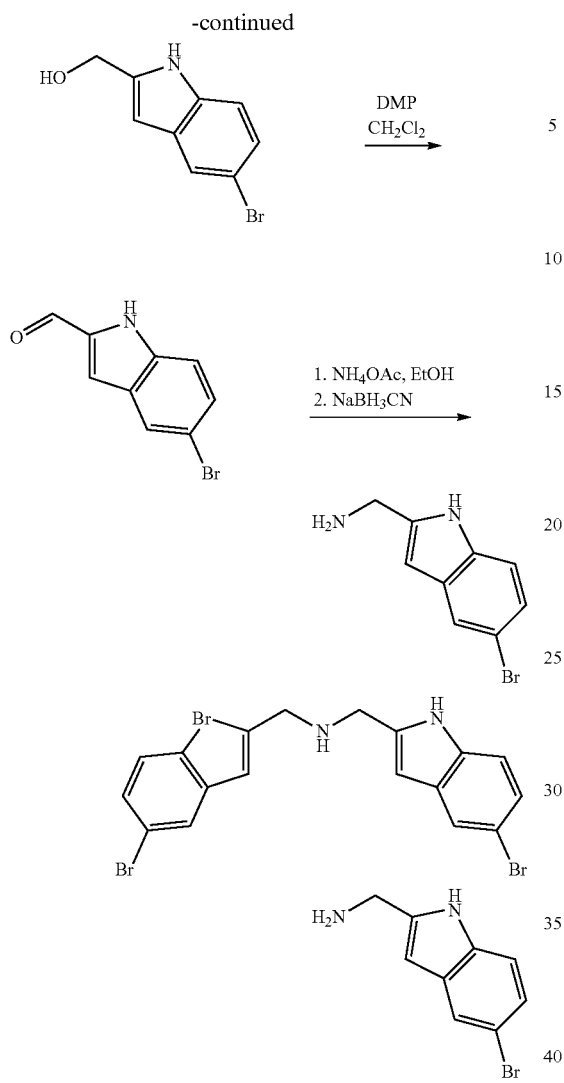

(5-Bromo-1H-indol-2-yl)methanamine

5-Bromo-1H-indole-2-carbaldehyde (55 mg, 0.25 mmol) was dissolved in ethanol (25 mL), and it was treated with ammonium acetate (193 mg, 2.50 mmol). The mixture was stirred for an hour at room temperature. Then, sodium cyanoborohydride (79 mg, 1.25 mmol) was added, and it was stirred for 3 hours at room temperature. The reaction mixture was diluted with ethyl acetate, and it was washed with saturated NaHCO$_3$ and brine. The organic layer was dried over Na$_2$SO$_4$, and it was concentrated under reduced pressure. The residue was purified on an ISCO chromatograph (0-10% methanol/dichloromethane+0.1% NH$_4$OH) to give (5-bromo-1H-indol-2-yl)methanamine as a white solid (26 mg, 46%). $^1$H NMR (300 MHz) (DMSO-d$_6$) δ 11.25 (bs, 1H), 7.72 (d, J=2 Hz, 1H), 7.36 (d, J=8 Hz, 1H), 7.19 (dd, J=9 Hz, J=2 Hz, 1H), 6.46 (s, 1H), 4.11 (s, 2H); LC/MS RT=2.52 (M−H−: 223/225). along with bis((5-bromo-1H-indol-2-yl)methyl)amine as a white solid (26 mg, 49%). $^1$H NMR (300 MHz) (CDCl$_3$) δ 7.65 (s, 2H), 7.26-7.21 (m, 4H), 6.31 (s, 2H), 3.97 (s, 4H); LC/MS RT=2.97 (M−H−: 430/432/434).

The requisite intermediate was prepared as follows:
Step 1)

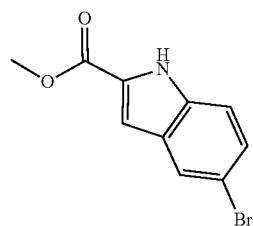

Methyl 5-bromo-1H-indole-2-carboxylate

5-Bromo-1H-indole-2-carboxylic acid (1.5 g, 6.25 mmol) was dissolved in methanol (100 mL), and it was treated with catalytic amount of concentrated sulfuric acid. The mixture was refluxed overnight. After removal of solvent, it was diluted with ethyl acetate. The organic layer was washed with 10% NaOH and brine, and it was dried over Na$_2$SO$_4$. The organic layer was concentrated under reduced pressure, and the residue was purified on an ISCO chromatograph (0-50% ethyl acetate/hexane) to give product as a white solid (1.19 g, 75%); $^1$H NMR (300 MHz) (CDCl$_3$) δ 8.97 (bs, 1H), 7.83 (s, 1H), 7.40 (dd, J=9 Hz, J=2 Hz, 1H), 7.30 (d, J=9 Hz, 1H), 7.14 (s, 1H), 3.95 (s, 3H).
Step 2)

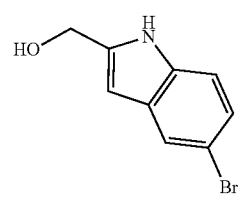 [SMILES: OCc1cc2cc(Br)ccc2[nH]1]

(5-Bromo-1H-indol-2-yl)methanol

Methyl 5-bromo-1H-indole-2-carboxylate (200 mg, 0.79 mmol) and lithium borohydride (86 mg, 3.95 mmol) were dissolved in anhydrous tetrahydrofuran (10 mL) at 0° C., and it was stirred for overnight at room temperature. The reaction mixture was diluted with ethyl acetate, and it was washed with saturated NH$_4$Cl and brine. The organic layer was dried over Na$_2$SO$_4$, and it was concentrated under reduced pressure. The residue was purified on an ISCO chromatograph (0-50% ethyl acetate/hexane) to give product as a white solid (149 mg, 83%); $^1$H NMR (300 MHz) (CDCl$_3$) δ 8.37 (bs, 1H), 7.69 (s, 1H), 7.28-7.21 (m, 2H), 6.34 (d, J=1 Hz, 1H), 4.84 (s, 2H).
Step 3)

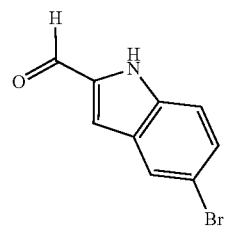 [SMILES: O=Cc1cc2cc(Br)ccc2[nH]1]

5-Bromo-1H-indole-2-carbaldehyde (5-Bromo-1H-indol-2-yl)methanol (100 mg, 0.44 mmol) and dess-martin periodinane (280 mg, 0.66 mmol) were dissolved in dichloromethane (10 mL), and it was stirred for 15 minutes at room temperature. The reaction mixture was diluted with ethyl acetate, and it was washed with 10% sodium thiosulfate, saturated NaHCO₃ and brine. The organic layer was dried over Na$_2$SO$_4$, and it was concentrated under reduced pressure. The residue was purified on an ISCO chromatograph (0-10% ethyl acetate/hexane) to give product as a white solid (55 mg, 56%); ¹H NMR (300 MHz) (CDCl₃) δ 9.85 (s, 1H), 9.05 (bs, 1H), 7.90 (s, 1H), 7.47 (dd, J=9 Hz, J=2 Hz, 1H), 7.34 (d, J=9 Hz, 1H), 7.21 (s, 1H).

Example 15. Preparation of 1-(4,6-dichloro-1H-indol-2-yl)ethan-1-amine

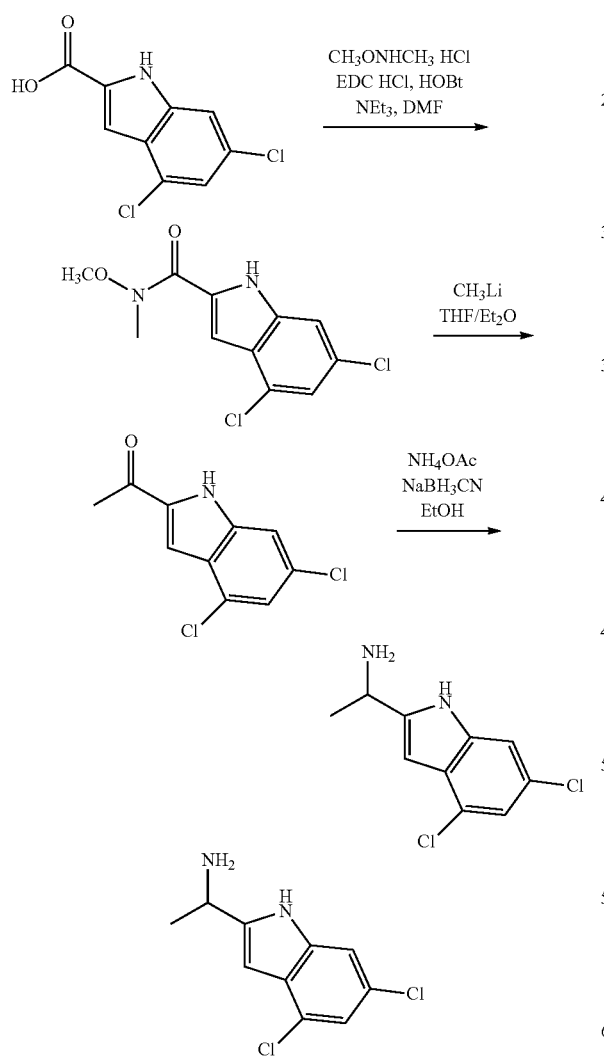

1-(4,6-Dichloro-1H-indol-2-yl)ethan-1-amine 1-(4,6-Dichloro-1H-indol-2-yl)ethan-1-one (100 mg, 0.44 mmol), ammonium acetate (339 mg, 4.40 mmol) and sodium cyanoborohydride (138 mg, 2.20 mmol) were dissolved in ethanol (10 mL). The mixture was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over Na$_2$SO$_4$. The organic layer was concentrated under reduced pressure, and the residue was purified on an ISCO chromatograph (0-10% methanol/dichloromethane+0.1% NH$_4$OH) to give the product as a white solid (55 mg, 54%); ¹H NMR (300 MHz) (DMSO-d$_6$) δ 7.32 (s, 1H), 7.06 (s, 1H), 6.27 (s, 1H), 4.12-4.01 (m, 1H), 1.35 (d, J=8 Hz, 3H); LC/MS RT=2.61 (M−H⁻: 227/229).

The requisite intermediate was prepared as follows:
Step 1)

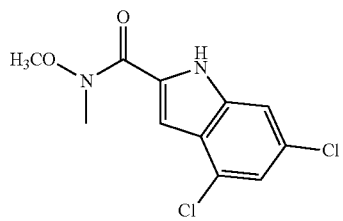 [SMILES: CON(C)C(=O)c1cc2c(Cl)cc(Cl)cc2[nH]1]

4,6-Dichloro-N-methoxy-N-methyl-1H-indole-2-carboxamide 4,6-Dichloro-1H-indole-2-carboxylic acid (500 mg, 2.17 mmol), N,O-dimethylhydroxylamine hydrochloride (423 mg, 4.34 mmol), HOBt (332 mg, 2.17 mmol), EDC hydrochloride (874 mg, 4.56 mmol) and triethylamine (1.32 mL, 8.68 mmol) were dissolved in anhydrous dimethylformamide (40 mL). The mixture was stirred for overnight at room temperature. The reaction mixture was diluted with ethyl acetate, and the organic layer was washed with water, saturated NH$_4$Cl, 10% NaOH and brine. The organic layer was dried over Na$_2$SO$_4$, and it was concentrated under reduced pressure. The residue was purified on an ISCO chromatograph (0-50% ethyl acetate/hexane) to give product as a white solid (505 mg, 85%); ¹H NMR (300 MHz) (DMSO-d$_6$) δ 12.10 (bs, 1H), 7.45 (d, J=1 Hz, 1H), 7.24 (d, J=1 Hz, 1H), 7.09 (s, 1H), 3.80 (s, 3H), 3.33 (s, 3H).
Step 2)

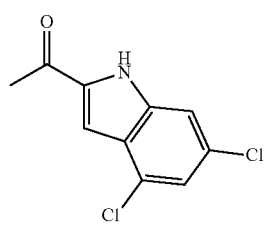

1-(4,6-Dichloro-1H-indol-2-yl)ethan-1-one 4,6-Dichloro-N-methoxy-N-methyl-1H-indole-2-carboxamide (500 mg, 1.83 mmol) was dissolved in anhydrous tetrahydrofuran (25 mL). The mixture was cooled to −78° C., and, then, a solution of 1.6 M methyllithium in diethyl ether (3.43 mL, 5.49 mmol) was added. The mixture was stirred for 2 hours at −78° C. The reaction was stopped by addition of water (10 mL). After removal of the solvent, the reaction mixture was diluted with ethyl acetate. The organic layer was washed with saturated NH₄Cl and brine, and it was dried over Na₂SO₄. The organic layer was concentrated under reduced pressure. The residue was purified on an ISCO chromatograph (0-20% ethyl acetate/hexane) to give product as a white solid (278 mg, 67%); $^1$H NMR (300 MHz) (DMSO-d$_6$) δ 12.20 (bs, 1H), 7.41 (s, 1H), 7.39 (s, 1H), 7.27 (s, 1H), 2.57 (s, 3H).

Example 16. Preparation of 1-(5-bromo-1H-indol-2-yl)-N,N-dimethylethan-1-amine

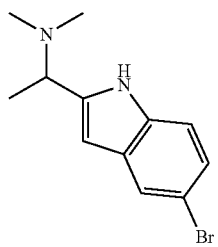

1-(5-Bromo-1H-indol-2-yl)-N,N-dimethylethan-1-amine

To a mixture of 1-(5-bromo-1H-indol-2-yl)ethan-1-one (75 mg, 0.32 mmol) in ethanol (10 mL), a solution of 2.0 M N,N-dimethylamine in tetrahydrofuran (1.60 mL, 3.20 mmol) was added. The mixture was treated with catalytic amount of acetic acid followed by sodium cyanoborohydride (101 mg, 1.69 mmol), and it was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over Na₂SO₄. The organic layer was concentrated under reduced pressure, and the residue was purified on an ISCO chromatograph (0-10% methanol/dichloromethane+0.1% NH₄OH) to give the product as a colorless oil (12 mg, 14%); $^1$H NMR (300 MHz) (CDCl₃) δ 8.81 (bs, 1H), 7.66 (s, 1H), 7.26-7.20 (m, 2H), 6.24 (s, 1H), 3.82-3.80 (m, 1H), 2.25 (s, 6H), 1.40 (d, J=7 Hz, 3H); LC/MS RT=2.62 (M−H⁻: 265/267).

Example 17. Preparation of 1-(5,6-difluoro-1H-indol-2-yl)ethan-1-amine

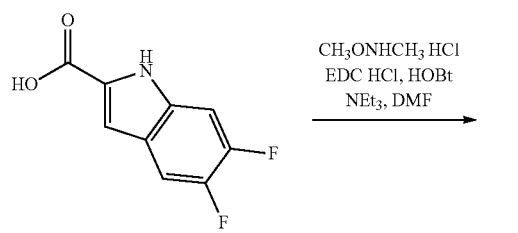

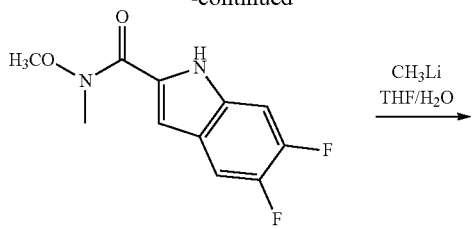

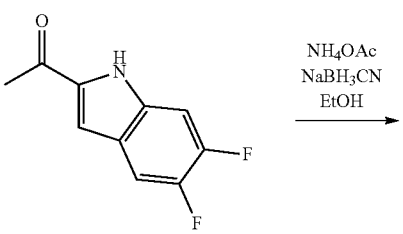

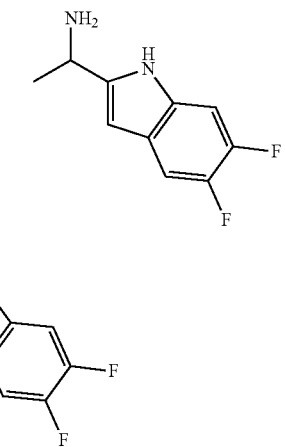

1-(5,6-Difluoro-1H-indol-2-yl)ethan-1-amine 1-(5,6-Difluoro-1H-indol-2-yl)ethan-1-one (150 mg, 0.77 mmol), ammonium acetate (594 mg, 7.70 mmol) and sodium cyanoborohydride (242 mg, 3.85 mmol) were dissolved in ethanol (10 mL). The mixture was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over Na₂SO₄. The organic layer was concentrated under reduced pressure, and the residue was purified on an ISCO chromatograph (0-10% methanol/dichloromethane+0.1% NH₄OH) to give the product as a white solid (69 mg, 46%); $^1$H NMR (300 MHz) (DMSO-d$_6$) δ 11.49 (bs, 1H), 8.49 (bs, 2H), 7.57-7.50 (m, 1H), 7.44-7.38 (m, 1H), 6.50 (s, 1H), 4.58-4.51 (m, 1H), 1.58 (d, J=6 Hz, 3H); LC/MS RT=2.47 (M−H⁻: 195).

The requisite intermediate was prepared as follows:
Step 1)

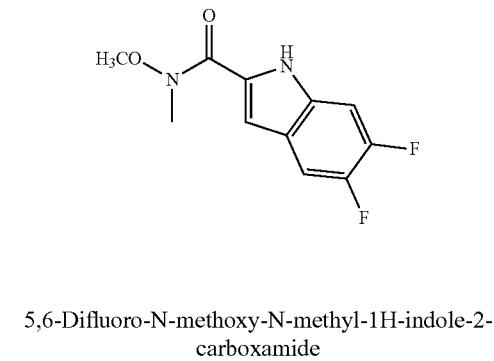

5,6-Difluoro-N-methoxy-N-methyl-1H-indole-2-carboxamide 5,6-Difluoro-1H-indole-2-carboxylic acid (500 mg, 2.54 mmol), N,O-dimethylhydroxylamine hydrochloride (496 mg, 5.08 mmol), HOBt (389 mg, 2.54 mmol), EDC hydrochloride (1.02 g, 5.33 mmol) and triethylamine (1.54 mL, 10.2 mmol) were dissolved in anhydrous dimethylformamide (20 mL). The mixture was stirred for overnight at room temperature. The reaction mixture was diluted with ethyl acetate, and the organic layer was washed with water, saturated NH$_4$Cl, 10% NaOH and brine. The organic layer was dried over Na$_2$SO$_4$, and it was concentrated under reduced pressure. The residue was purified on an ISCO chromatograph (0-50% ethyl acetate/hexane) to give product as a white solid (367 mg, 60%); $^1$H NMR (300 MHz) (CDCl$_3$) δ 9.33 (bs, 1H), 7.45-7.38 (m, 1H), 7.23-7.17 (m, 2H), 3.85 (s, 3H), 3.42 (s, 3H).

Step 2)

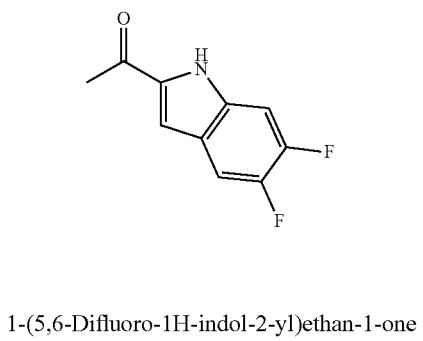

1-(5,6-Difluoro-1H-indol-2-yl)ethan-1-one 5,6-Difluoro-N-methoxy-N-methyl-1H-indole-2-carboxamide (350 mg, 1.46 mmol) was dissolved in anhydrous tetrahydrofuran (20 mL). The mixture was cooled to −78° C., and, then, a solution of 1.6 M methyllithium in diethyl ether (2.73 mL, 4.38 mmol) was added. The mixture was stirred for 2 hours at −78° C. The reaction was stopped by addition of water (10 mL). After removal of the solvent, the reaction mixture was diluted with ethyl acetate. The organic layer was washed with saturated NH$_4$Cl and brine, and it was dried over Na$_2$SO$_4$. The organic layer was concentrated under reduced pressure. The residue was purified on an ISCO chromatograph (0-20% ethyl acetate/hexane) to give product as a white solid (207 mg, 73%); $^1$H NMR (300 MHz) (CDCl$_3$) δ 9.24 (bs, 1H), 7.47-7.41 (m, 1H), 7.26-7.14 (m, 2H), 2.58 (s, 3H).

Example 18. Preparation of 7-bromo-1,2,3,4-tetrahydrocyclopenta[b]indol-3-amine

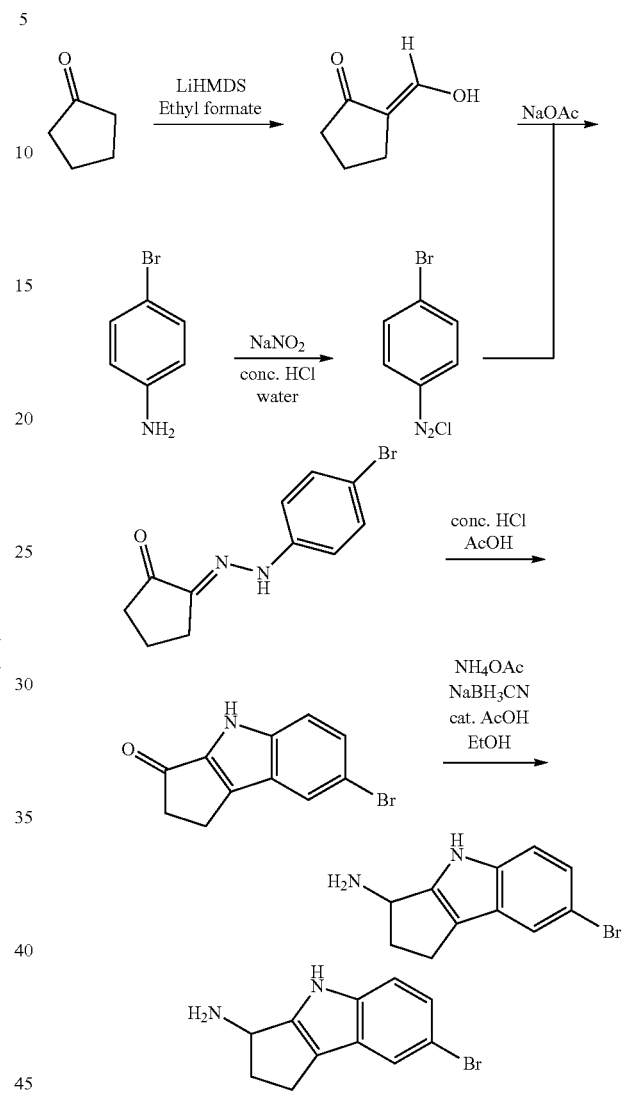

7-Bromo-1,2,3,4-tetrahydrocyclopenta[b]indol-3-amine

7-Bromo-1,4-dihydrocyclopenta[b]indol-3(2H)-one (100 mg, 0.40 mmol), ammonium acetate (308 mg, 4.00 mmol) and sodium cyanoborohydride (126 mg, 2.00 mmol) were dissolved in ethanol (10 mL). The mixture was stirred for overnight at 60° C. An additional ammonium acetate (308 mg, 4.00 mmol) and sodium cyanoborohydride (126 mg, 2.00 mmol) along with catalytic amount of acetic acid were added. The mixture was stirred for 5 hours at 85° C. The reaction mixture was acidified with 6N HCl, and it was washed with ethyl acetate. Then, the aqueous layer was basified with NaOH, and it was extracted with ethyl acetate. The organic layer was washed with brine, and it was dried over Na$_2$SO$_4$. The organic layer was concentrated under reduced pressure, and the residue was purified on an ISCO chromatograph (0-10% methanol/dichloromethane+0.1% NH$_4$OH) to give the product as a white solid (17 mg, 17%);

¹H NMR (300 MHz) (CD₃OD) δ 7.48 (d, J=1 Hz, 1H), 7.22 (d, J=9 Hz, 1H), 7.12 (dd, J=9 Hz, J=2 Hz, 1H), 4.43-4.41 (m, 1H), 2.94-2.83 (m, 2H), 2.78-2.62 (m, 1H), 2.21-2.12 (m, 1H); LC/MS RT=2.57 (M−H⁻: 249/251).

The requisite intermediate was prepared as follows:

Step 1)

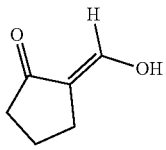

5 (E)-2-(Hydroxymethylene)cyclopentan-1-one

Cyclopentanone (2.21 mL, 25 mmol) was dissolved in anhydrous tetrahydrofuran (10 mL), and it was cooled to 0° C. A solution of 1.0 M LHMDS in tetrahydrofuran (30 mL, 30 mmol) was slowly added, and it was stirred for 5 minutes at the temperature. Ethyl formate (2.42 mL, 30 mmol) was slowly added, and it was stirred for 2 hours at the temperature. The reaction mixture was diluted with ethyl acetate, and it was washed with 6N HCl and brine. The organic layer was dried over Na₂SO₄, and it was concentrated under reduced pressure. The residue was purified on an ISCO chromatograph (0-30% ethyl acetate/hexane) to give product as a white solid (772 mg, 28%); ¹H NMR (300 MHz) (CDCl₃) δ 7.21 (s, 1H), 2.56-2.51 (m, 2H), 2.43-2.37 (m, 2H), 2.01-1.94 (m, 2H).

Step 2)

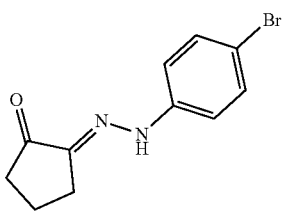 [SMILES: O=C1CCC/C1=N\Nc1ccc(Br)cc1]

(E)-2-(2-(4-Bromophenyl)hydrazineylidene)cyclo-pentan-1-one

To a solution of 4-bromoaniline (1.07 g, 6.23 mmol) in concentrated hydrochloric acid (2 mL), a solution of sodium nitrite (430 mg, 6.23 mmol) in water (4 mL) was added slowly at 0° C. The mixture was stirred for 30 minutes at the temperature. In a separate round bottom flask, 5 (E)-2-(hydroxymethylene)cyclopentan-1-one (700 mg, 6.23 mmol) was dissolve in methanol (12 mL). To the mixture, a solution of sodium acetate (1.28 g, 15.58 mmol) in water (5 mL) was added slowly at 0° C. The mixture was stirred for 20 minutes at the temperature. Then, the freshly prepared diazonium salt solution was slowly added. The mixture was stirred for additional 30 minutes at the temperature, and the formed yellow suspension was filtered to give the product as a yellow solid (1.47 g, 89%); ¹H NMR (300 MHz) (DMSO-d₆) δ 10.03 (s, 1H), 7.42 (d, J=9 Hz, 2H), 7.19 (d, J=9 Hz, 2H), 2.65-2.60 (m, 2H), 2.34-2.29 (m, 2H), 1.99-1.95 (m, 2H).

Step 3)

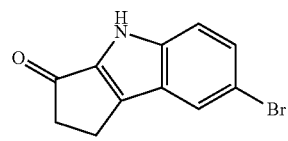 [SMILES: O=C1CCc2c1[nH]c1ccc(Br)cc21]

7-Bromo-1,4-dihydrocyclopenta[b]indol-3(2H)-one (E)-2-(2-(4-Bromophenyl)hydrazineylidene)cyclopentan-1-one (1.47 g, 5.50 mmol) was dissolved in a mixture of concentrated hydrochloric acid (2 mL) and acetic acid (8 mL), and it was stirred for 30 minutes at 130° C. The resulting dark brown suspension was diluted with ethyl acetate, and it was washed with 10% NaOH and brine. The organic layer was dried over Na₂SO₄, and it was concentrated under reduced pressure. The residue was purified on an ISCO chromatograph (0-20% ethyl acetate/hexane) to give product as a beige solid (116 mg, 8%); ¹H NMR (300 MHz) (CDCl₃) δ 8.80 (bs, 1H), 7.87 (d, J=2 Hz, 1H), 7.48 (dd, J=9 Hz, J=2 Hz, 1H), 7.35 (d, J=9 Hz, 1H), 3.10-3.07 (m, 2H), 3.03-3.00 (m, 2H).

Example 19. Preparation of 2-Bromo-5,6,7,8,9,10-hexahydrocyclohepta[b]indol-6-amine

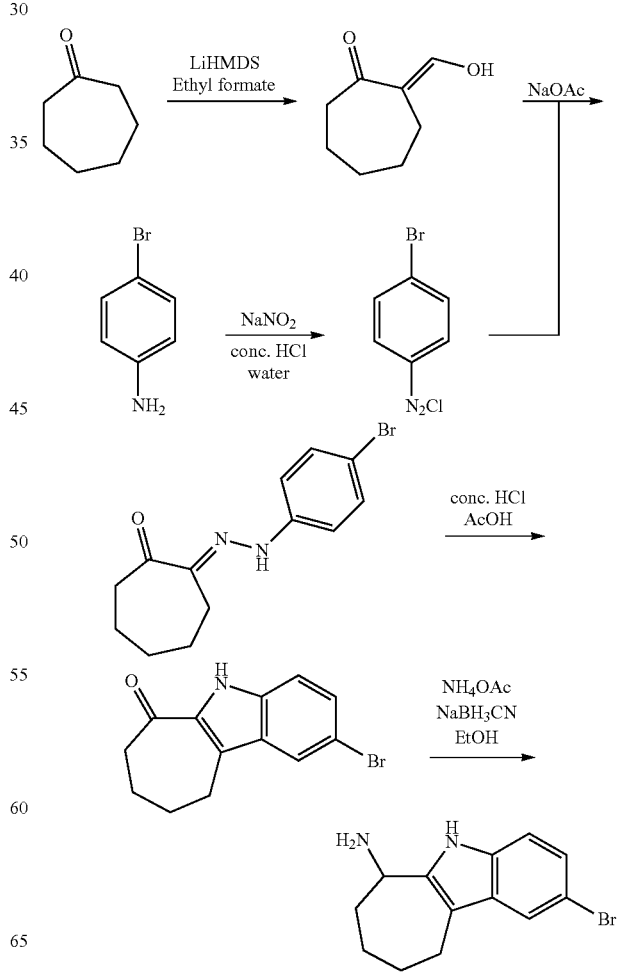

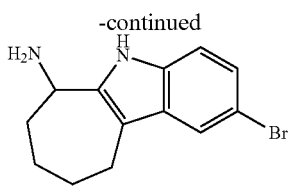

2-Bromo-5,6,7,8,9,10-hexahydrocyclohepta[b]indol-6-amine

2-Bromo-7,8,9,10-tetrahydrocyclohepta[b]indol-6(5H)-one (100 mg, 0.36 mmol), ammonium acetate (277 mg, 3.60 mmol) and sodium cyanoborohydride (113 mg, 1.80 mmol) were dissolved in ethanol (10 mL). The mixture was stirred for overnight at 60° C. The reaction mixture was acidified with 6N HCl, and it was washed with ethyl acetate. Then, the aqueous layer was basified with NaOH, and it was extracted with ethyl acetate. The organic layer was washed with brine, and it was dried over $Na_2SO_4$. The organic layer was concentrated under reduced pressure, and the residue was purified on an ISCO chromatograph (0-10% methanol/dichloromethane+0.1% $NH_4OH$) to give the product as a white solid (34 mg, 34%); $^1$H NMR (300 MHz) ($CD_3OD$) δ 10.76 (bs, 1H), 7.51 (d, J=2 Hz, 1H), 7.24 (d, J=8 Hz, 1H), 7.03 (dd, J=8 Hz, J=2 Hz, 1H), 4.01-3.97 (m, 1H), 2.86-2.81 (m, 1H), 2.58-2.56 (m, 1H), 1.99-1.84 (m, 2H), 1.71-1.50 (m, 4H); LC/MS RT=2.57 (M−H⁻: 277/279).

The requisite intermediate was prepared as follows:

Step 1)

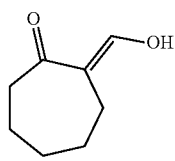

(E)-2-(Hydroxymethylene)cycloheptan-1-one

Cycloheptanone (2.95 mL, 25 mmol) was dissolved in anhydrous tetrahydrofuran (10 mL), and it was cooled to 0° C. A solution of 1.0 M LHMDS in tetrahydrofuran (30 mL, 30 mmol) was slowly added, and it was stirred for 5 minutes at the temperature. Ethyl formate (2.42 mL, 30 mmol) was slowly added, and it was stirred for 2 hours at the temperature. The reaction mixture was diluted with ethyl acetate, and it was washed with 6N HCl and brine. The organic layer was dried over $Na_2SO_4$. The organic layer was concentrated under reduced pressure. The residue was purified on an ISCO chromatograph (0-20% ethyl acetate/hexane) to give product as a colorless oil (1.30 g, 37%); $^1$H NMR (300 MHz) ($CDCl_3$) δ 7.59 (d, J=9 Hz, 1H), 2.51-2.47 (m, 2H), 2.23-2.19 (m, 2H), 1.73-1.54 (m, 6H).

Step 2)

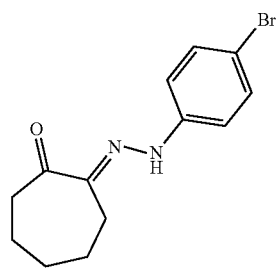 [SMILES: O=C1CCCCC/C1=N\Nc1ccc(Br)cc1]

(E)-2-(2-(4-Bromophenyl)hydrazineylidene)cycloheptan-1-one

To a solution of 4-bromoaniline (1.60 g, 9.30 mmol) in concentrated hydrochloric acid (2 mL), a solution of sodium nitrite (642 mg, 9.30 mmol) in water (4 mL) was added slowly at 0° C. The mixture was stirred for 30 minutes at the temperature. In a separate round bottom flask, (E)-2-(hydroxymethylene)cycloheptan-1-one (1.30 g, 9.30 mmol) was dissolve in methanol (12 mL). To the mixture, a solution of sodium acetate (1.91 g, 23.3 mmol) in water (5 mL) was added slowly at 0° C. The mixture was stirred for 20 minutes at the temperature. Then, the freshly prepared diazonium salt solution was slowly added. The mixture was stirred for additional 30 minutes at the temperature, and the formed yellow suspension was filtered to give the product as a yellow solid (2.17 g, 79%); H NMR (300 MHz) (DMSO-$d_6$) δ 13.27 (s, 1H), 7.43 (d, J=9 Hz, 2H), 7.23 (d, J=9 Hz, 2H), 2.62-2.56 (m, 4H), 1.68 (m, 6H).

Step 3)

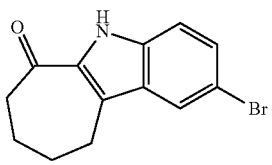 [SMILES: O=C1CCCCc2c1[nH]c1ccc(Br)cc21]

2-Bromo-7,8,9,10-tetrahydrocyclohepta[b]indol-6(5H)-one (E)-2-(2-(4-Bromophenyl)hydrazineylidene)cycloheptan-1-one (2.17 g, 7.35 mmol) was dissolved in a mixture of concentrated hydrochloric acid (2 mL) and acetic acid (8 mL), and it was stirred for 30 minutes at 130° C. The resulting dark brown suspension was diluted with ethyl acetate, and it was washed with 10% NaOH and brine. The organic layer was dried over $Na_2SO_4$, and it was concentrated under reduced pressure. The residue was purified on an ISCO chromatograph (0-20% ethyl acetate/hexane) to give product as a yellow solid (472 mg, 23%); $^1$H NMR (300 MHz) ($CDCl_3$) δ 8.90 (bs, 1H), 7.79 (s, 1H), 7.41 (dd, J=9 Hz, J=2 Hz, 1H), 7.26-7.23 (m, 1H), 3.11-3.07 (m, 2H), 2.86-2.82 (m, 2H), 2.11-1.99 (m, 4H).

Example 20. Preparation of 1,2-dichloro-5,6,7,8,9,10-hexahydrocyclohepta[b]indol-6-amine

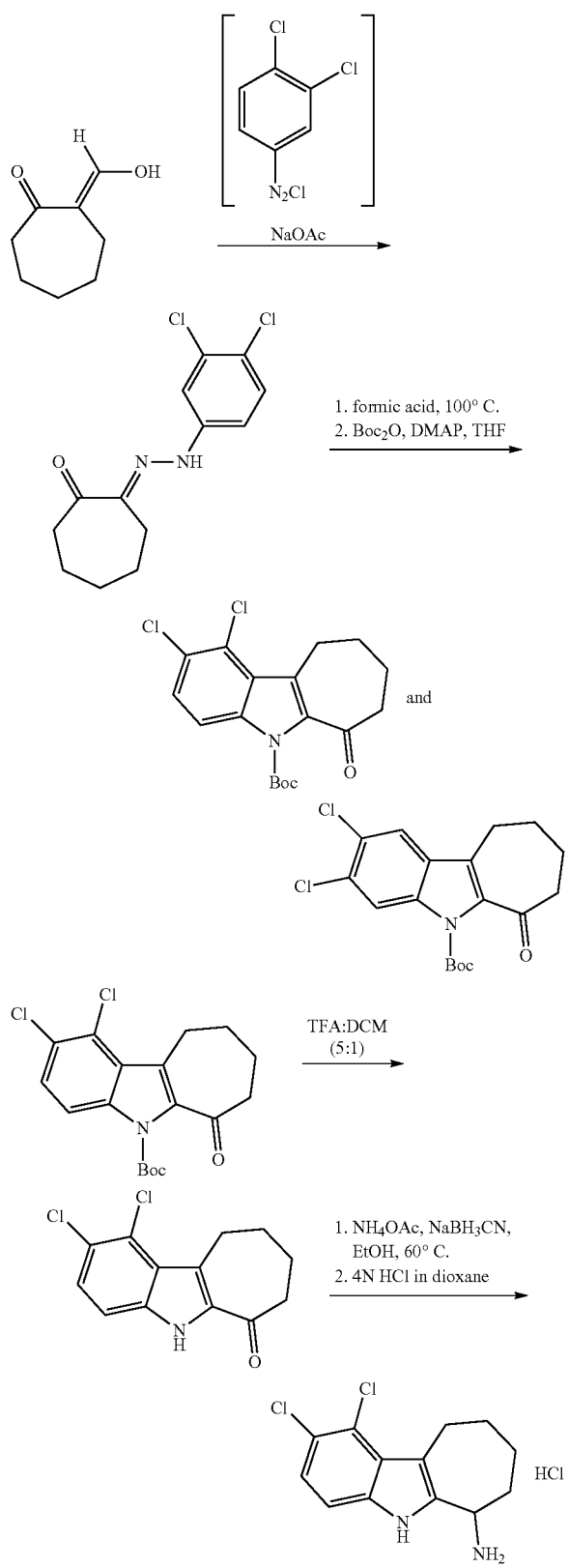

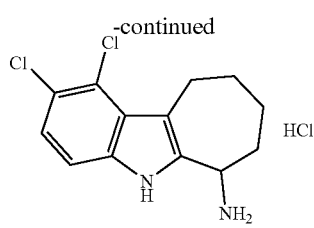

1,2-Dichloro-5,6,7,8,9,10-hexahydrocyclohepta[b]indol-6-amine hydrochloric acid 1,2-Dichloro-7,8,9,10-tetrahydrocyclohepta[b]indol-6(5H)-one (99 mg, 0.37 mmol), ammonium acetate (285 mg, 3.70 mmol) and sodium cyanoborohydride (116 mg, 1.85 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give product as a white solid. The solid was then treated with 4N hydrochloric acid in dioxane, and it was stirred for 30 minutes at room temperature. The white suspension was concentrated under reduced pressure, and the resulting residue was suspended in ethyl acetate. The suspension was filtered to give hydrochloric acid salt of product as a white solid (42 mg, 37%); $^1$H NMR (300 MHz) (DMSO-d$_6$) δ 11.65 (bs, 1H), 8.42 (bs, 3H), 7.37 (d, J=8 Hz, 1H), 7.25 (d, J=9 Hz, 1H), 4.58 (m, 1H), 3.65-3.60 (m, 2H), 3.12-2.98 (m, 2H), 1.97-1.89 (m, 4H); LC/MS RT=2.90 (M−H$^−$: 267/269).

The requisite intermediate was prepared as follows:

Step 1)

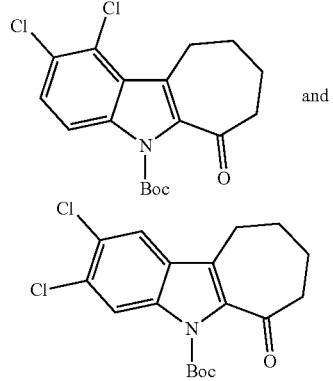

tert-Butyl 1,2-dichloro-6-oxo-7,8,9,10-tetrahydrocyclohepta[b]indole-5(6H)-carboxylate and tert-Butyl 2,3-dichloro-6-oxo-7,8,9,10-tetrahydrocyclohepta[b]indole-5(6H)-carboxylate To a solution of 3,4-dichloroaniline (1.53 g, 9.42 mmol) in concentrated hydrochloric acid (10 mL), a solution of sodium nitrite (650 mg, 9.42 mmol) in water (20 mL) was added slowly at 0° C. The mixture was stirred for 30 minutes at the temperature. In a separate round bottom flask, (E)-2-(hydroxymethylene)cycloheptan-1-one (1.32 g, 9.42 mmol)

was dissolve in methanol (12 mL). To the mixture, a solution of sodium acetate (1.93 g, 23.55 mmol) in water (5 mL) was added slowly at 0° C. The mixture was stirred for 20 minutes at 0° C. Then, the freshly prepared diazonium salt solution was slowly added. The mixture was stirred for additional 30 minutes at 0° C. The reaction mixture was diluted with ethyl acetate, and the organic layer was washed with saturated sodium bicarbonate followed brine. The organic layer was concentrated under reduced pressure and the resulted dark brown oil was carried next step without further purification.

The residue was dissolved in formic acid (10 mL), and it was stirred for 2 hours at 100° C. The resulting dark brown suspension was diluted with ethyl acetate, and it was washed with 10% NaOH and brine. The organic layer was dried over sodium sulfate, and it was concentrated under reduced pressure. The residue was purified on an ISCO chromatograph (0-20% ethyl acetate/hexane) to give a mixture of two regioisomers, 1,2-dichloro-7,8,9,10-tetrahydrocyclohepta[b]indol-6(5H)-one and 2,3-dichloro-7,8,9,10-tetrahydrocyclohepta[b]indol-6(5H)-one as a beige solid (212 mg, 8%).

To a solution of a mixture of the two regioisomers (212 mg, 0.79 mmol) in tetrahydrofuran (10 mL), boc anhydride (345 mg, 1.58 mmol) and DAMP (89 mg, 0.79 mmol) were added. The reaction mixture was stirred for 3 hours. The reaction mixture was diluted with ethyl acetate, and it was washed with saturated ammonium chloride, followed by brine. The organic layer was dried over sodium sulfate, and it was concentrated under reduced pressure. The residue was purified on an ISCO chromatograph (0-10% ethyl acetate/hexane) to give tert-butyl 1,2-dichloro-6-oxo-7,8,9,10-tetrahydrocyclohepta[b]indole-5(6H)-carboxylate (152 mg, 49%). $^1$H NMR (300 MHz) (CDCl$_3$) δ 7.93 (d, J=9 Hz, 1H), 7.41 (d, J=9 Hz, 1H), 3.42-3.38 (m, 2H), 2.87-2.83 (m, 2H), 1.97-1.95 (m, 4H), 1.55 (s, 9H). along with tert-butyl 2,3-dichloro-6-oxo-7,8,9,10-tetrahydrocyclohepta[b]indole-5(6H)-carboxylate (59 mg, 20%). $^1$H NMR (300 MHz) (CDCl$_3$) δ 8.20 (s, 1H), 7.62 (s, 1H), 2.91 (m, 2H), 2.85 (m, 2H), 2.02-1.98 (m, 4H), 1.57 (s, 9H).
Step 2)

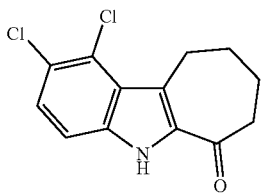 [SMILES: O=C1CCCCc2c1[nH]c1ccc(Cl)c(Cl)c21]

1,2-Dichloro-7,8,9,10-tetrahydrocyclohepta[b]indol-6(5H)-one

To a solution of tert-butyl 1,2-dichloro-6-oxo-7,8,9,10-tetrahydrocyclohepta[b]indole-5(6H)-carboxylate (152 mg, 0.41 mmol) in dichloromethane (5 mL), trifluoroacetic acid (1 mL) was added. The reaction mixture was stirred for an hour at room temperature. After removal of solvent, the mixture was diluted with ethyl acetate, and it was washed with 10% sodium hydroxide and brine. The organic layer was dried over sodium sulfate, and it was concentrated under reduced pressure to give product as a white solid (99 mg, 90%); $^1$H NMR (300 MHz) (CDCl$_3$) δ 9.08 (bs, 1H), 7.35 (d, J=9 Hz, 1H), 7.20 (d, J=9 Hz, 1H), 3.58-3.54 (m, 2H), 2.87-2.83 (m, 2H), 2.11-2.04 (m, 2H), 1.99-1.91 (m, 2H).

Example 21. Preparation of 2,3-dichloro-5,6,7,8,9,10-hexahydrocyclohepta[b]indol-6-amine

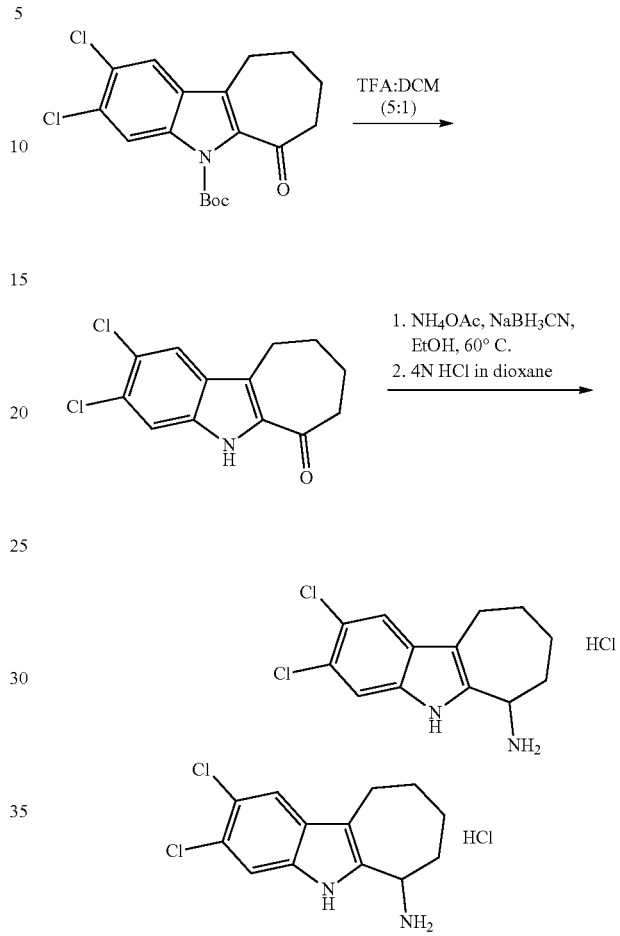

2,3-Dichloro-5,6,7,8,9,10-hexahydrocyclohepta[b]indol-6-amine hydrochloric acid 2,3-Dichloro-7,8,9,10-tetrahydrocyclohepta[b]indol-6(5H)-one (100 mg, 0.37 mmol), ammonium acetate (285 mg, 3.70 mmol) and sodium cyanoborohydride (116 mg, 1.85 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give product as a white solid. The solid was then treated with 4N hydrochloric acid in dioxane, and it was stirred for 30 minutes at room temperature. The white suspension was concentrated under reduced pressure, and the resulting residue was suspended in ethyl acetate. The suspension was filtered to give hydrochloric acid salt of product as a white solid (76 mg, 67%); $^1$H NMR (300 MHz) (DMSO-d$_6$) δ 11.36 (bs, 1H), 8.44 (bs, 3H), 7.78 (s, 1H), 7.62 (s, 1H), 4.56 (m, 1H), 3.55-3.26 (m, 2H), 2.89-2.71 (m, 4H), 1.93-1.76 (m, 2H); LC/MS RT=2.91 (M−H$^-$: 267/269).

The requisite intermediate was prepared as follows:
Step 1)

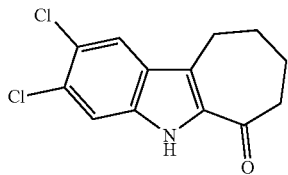 [SMILES: O=C1CCCCc2c1[nH]c1cc(Cl)c(Cl)cc21]

2,3-Dichloro-7,8,9,10-tetrahydrocyclohepta[b]indol-6(5)-one

To a solution of tert-butyl 2,3-dichloro-6-oxo-7,8,9,10-tetrahydrocyclohepta[b]indole-5(6H)-carboxylate (943 mg, 2.64 mmol) in dichloromethane (25 mL), trifluoroacetic acid (5 mL) was added. The reaction mixture was stirred for 2 hours at room temperature. After removal of solvent, the mixture was diluted with ethyl acetate, and it was washed with 10% sodium hydroxide and brine. The organic layer was dried over sodium sulfate, and it was concentrated under reduced pressure to give product as a white solid (675 mg, 95%); $^1$H NMR (300 MHz) (CDCl$_3$) δ 8.90 (bs, 1H), 7.74 (s, 1H), 7.48 (s, 1H), 3.10-3.06 (m, 2H), 2.87-2.83 (m, 2H), 2.11-2.05 (m, 2H), 2.01-1.99 (m, 2H).

Example 22. Preparation of 7,8-dichloro-1,2,3,4-tetrahydrocyclopenta[b]indol-3-amine

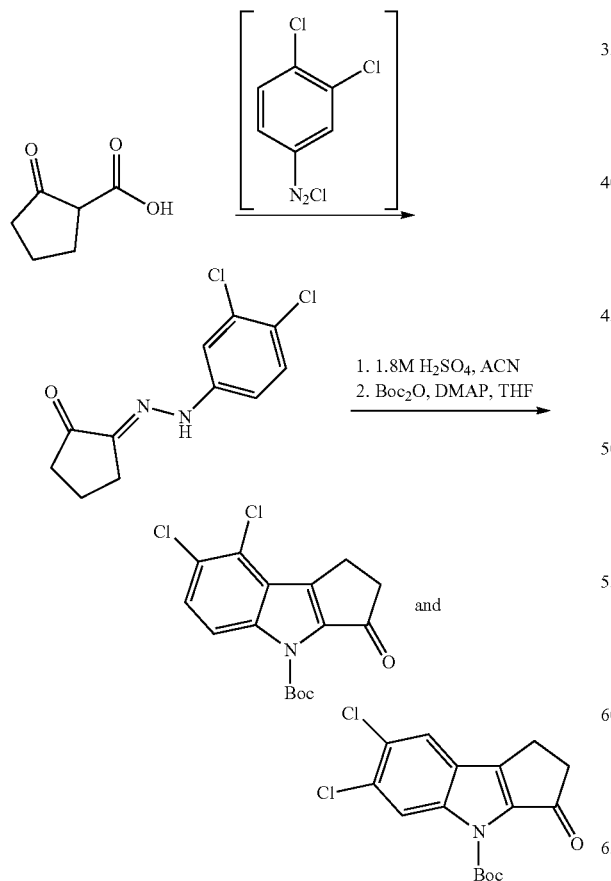

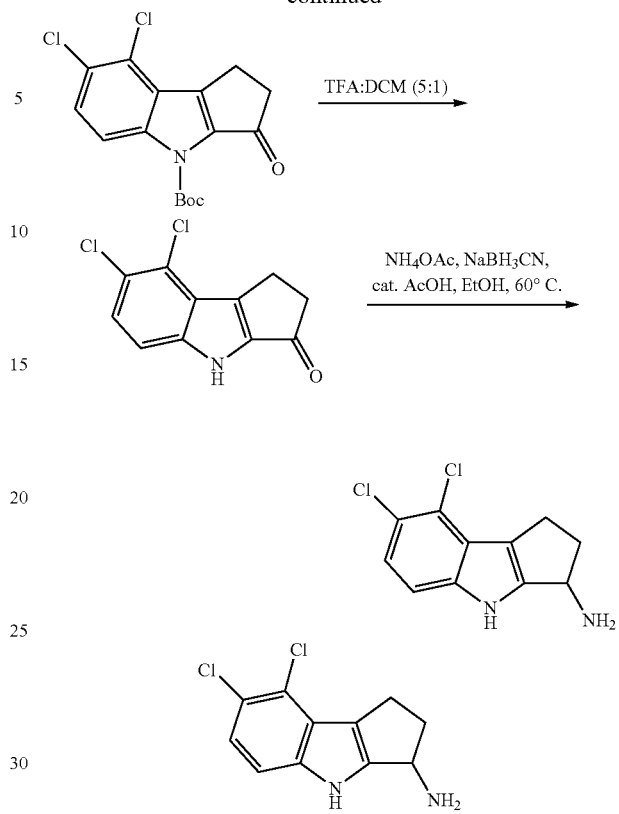

7,8-Dichloro-1,2,3,4-tetrahydrocyclopenta[b]indol-3-amine 7,8-Dichloro-1,4-dihydrocyclopenta[b]indol-3(2H)-one (100 mg, 0.42 mmol), ammonium acetate (647 mg, 8.40 mmol) and sodium cyanoborohydride (132 mg, 2.10 mmol) were dissolved in ethanol (10 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give product as a white solid (41 mg, 41%); $^1$H NMR (300 MHz) (MeOD) δ 7.22 (d, J=9 Hz, 1H), 7.09 (d, J=9 Hz, 1H), 4.47-4.44 (m, 1H), 3.16-3.07 (m, 1H), 2.95-2.83 (m, 2H), 2.24-2.16 (m, 1H); LC/MS RT=2.74 (M−H$^-$: 239/241).

The requisite intermediate was prepared as follows:
Step 1)

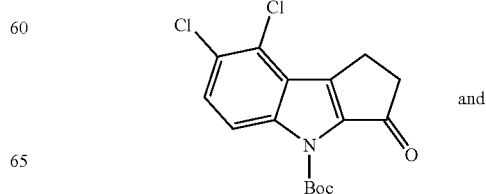

and

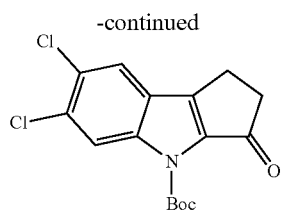

tert-Butyl 7,8-dichloro-3-oxo-2,3-dihydrocyclopenta[b]indole-4(1H)-carboxylate and tert-Butyl 6,7-dichloro-3-oxo-2,3-dihydrocyclopenta[b]indole-4(1H)-carboxylate To a suspension of 3,4-dichloroaniline (8.10 g, 50.00 mmol) in water (30 mL), concentrated hydrochloric acid (12.5 mL) was slowly added at 0° C. Then, a solution of sodium nitrite (3.45 g, 50.00 mmol) in water (35 mL) was slowly added at 0° C. The mixture was stirred for 30 minutes at 0° C. This freshly prepared diazonium salt solution was slowly added to a solution of 2-oxocyclopentane-1-carboxylic acid (6.40 g, 50.00 mmol) in concentrated hydrochloric acid (4.58 mL). The mixture was stirred for additional 30 minutes at 0° C. to give a yellow suspension. The suspension was filtered to give intermediate, (E)-2-(2-(3,4-dichlorophenyl)hydrazineylidene)cyclopentan-1-one, as an orange solid.

The intermediate was then dissolved in acetonitrile (50 mL), and 1.8M sulfuric acid was added. The reaction mixture was stirred for overnight at 75° C. The resulting dark brown suspension was diluted with ethyl acetate, and it was washed with 10% NaOH and brine. The organic layer was dried over sodium sulfate, and it was concentrated under reduced pressure. The residue was purified on an ISCO chromatograph (0-20% ethyl acetate/hexane) to give a mixture of two regioisomers, 7,8-dichloro-1,4-dihydrocyclopenta[b]indol-3(2H)-one and 6,7-dichloro-1,4-dihydrocyclopenta[b]indol-3(2H)-one as a dark brown solid (493 mg, 10%).

To a solution of a mixture of the two regioisomers (493 mg, 2.05 mmol) in tetrahydrofuran (25 mL), boc anhydride (895 mg, 4.10 mmol) and DAMP (230 mg, 2.05 mmol) were added. The reaction mixture was stirred for 3 hours. The reaction mixture was diluted with ethyl acetate, and it was washed with saturated ammonium chloride, followed by brine. The organic layer was dried over sodium sulfate, and it was concentrated under reduced pressure. The residue was purified on an ISCO chromatograph (0-10% ethyl acetate/hexane) to give tert-butyl 7,8-dichloro-3-oxo-2,3-dihydrocyclopenta[b]indole-4(1H)-carboxylate (121 mg, 17%). $^1$H NMR (300 MHz) (CDCl$_3$) δ 8.15 (d, J=9 Hz, 1H), 7.48 (d, J=9 Hz, 1H), 3.26-3.22 (m, 2H), 3.02-2.99 (m, 2H), 1.68 (s, 9H). along with tert-butyl 6,7-dichloro-3-oxo-2,3-dihydrocyclopenta[b]indole-4(1H)-carboxylate (160 mg, 23%). $^1$H NMR (300 MHz) (CDCl$_3$) δ 8.47 (s, 1H), 7.73 (s, 1H), 3.01-3.00 (m, 4H), 1.69 (s, 9H).

Step 2)

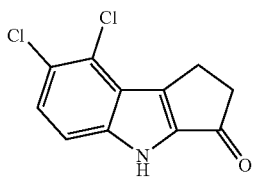 [SMILES: O=C1CCc2c1[nH]c1ccc(Cl)c(Cl)c21]

7,8-Dichloro-1,4-dihydrocyclopenta[b]indol-3(2H)-one

To a solution of tert-butyl 7,8-dichloro-3-oxo-2,3-dihydrocyclopenta[b]indole-4(1H)-carboxylate (121 mg, 0.36 mmol) in dichloromethane (5 mL), trifluoroacetic acid (1 mL) was added. The reaction mixture was stirred for an hour at room temperature. After removal of solvent, the mixture was diluted with ethyl acetate, and it was washed with 10% sodium hydroxide and brine. The organic layer was dried over sodium sulfate, and it was concentrated under reduced pressure to give product as a white solid (27 mg, 31%); $^1$H NMR (300 MHz) (CDCl$_3$) δ 9.61 (bs, 1H), 7.41 (d, J=9 Hz, 1H), 7.36 (d, J=9 Hz, 1H), 3.35-3.32 (m, 2H), 3.09-3.03 (m, 2H).

Example 23. Preparation of 6,7-dichloro-1,2,3,4-tetrahydrocyclopenta[b]indol-3-amine

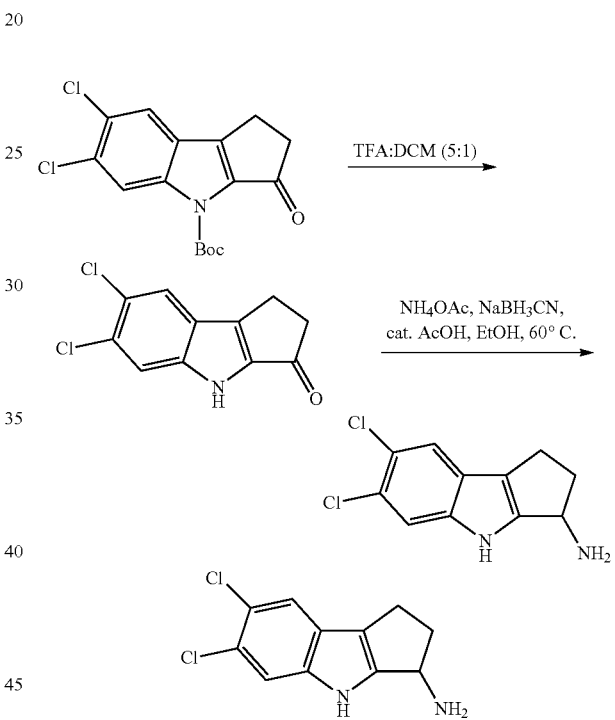

6,7-Dichloro-1,2,3,4-tetrahydrocyclopenta[b]indol-3-amine 6,7-Dichloro-1,4-dihydrocyclopenta[b]indol-3(2H)-one (148 mg, 0.62 mmol), ammonium acetate (956 mg, 12.4 mmol) and sodium cyanoborohydride (195 mg, 3.1 mmol) were dissolved in ethanol (20 mL). The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give product as a white solid (93 mg, 62%); $^1$H NMR (300 MHz) (MeOD) δ 7.46 (s, 1H), 7.45 (s, 1H), 4.43-4.39 (m, 1H), 2.93-2.79 (m, 2H), 2.71-2.61 (m, 1H), 2.21-2.12 (m, 1H); LC/MS RT=2.74 (M−H$^-$: 239/241).

The requisite intermediate was prepared as follows:
Step 1)

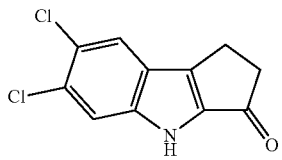 [SMILES: O=C1CCc2c1[nH]c1cc(Cl)c(Cl)cc21]

6,7-Dichloro-1,4-dihydrocyclopenta[b]indol-3(2H)-one

To a solution of tert-butyl 6,7-dichloro-3-oxo-2,3-dihydrocyclopenta[b]indole-4(1H)-carboxylate (571 mg, 1.68 mmol) in dichloromethane (25 mL), trifluoroacetic acid (5 mL) was added. The reaction mixture was stirred for an hour at room temperature. After removal of solvent, the mixture was diluted with ethyl acetate, and it was washed with 10% sodium hydroxide and brine. The organic layer was dried over sodium sulfate, and it was concentrated under reduced pressure to give product as a white solid (148 mg, 37%); $^1$H NMR (300 MHz) (DMSO-$d_6$) δ 11.98 (bs, 1H), 8.06 (s, 1H), 7.64 (s, 1H), 3.02-2.99 (m, 2H), 2.90-2.87 (m, 2H).

Example 24. Preparation of N-(1-(5-bromo-1H-indol-2-yl)ethyl)propane-1,3-diamine

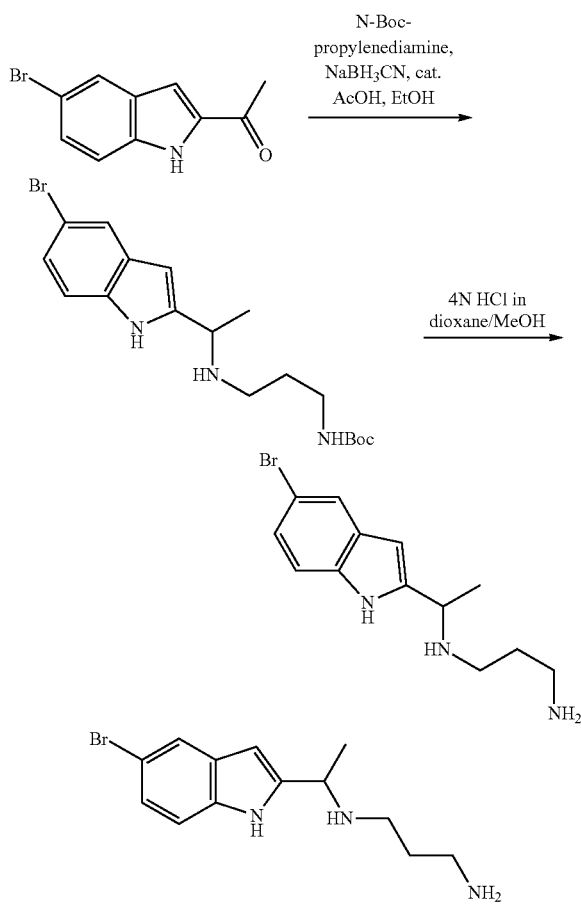

$N^1$-(1-(5-Bromo-1H-indol-2-yl)ethyl)propane-1,3-diamine

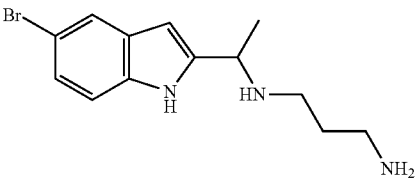 [SMILES: CC(NCCCN)c1cc2cc(Br)ccc2[nH]1]

$N^1$-(1-(5-Bromo-1H-indol-2-yl)ethyl)propane-1,3-diamine

To a solution of tert-butyl (3-((1-(5-bromo-1H-indol-2-yl)ethyl)amino)propyl)carbamate (817 mg, 2.06 mmol) in methanol (3 mL), 4N HCl in dioxane (6 mL, 24 mmol) was added. The reaction mixture was stirred for an hour at room temperature. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as colorless oil (332 mg, 54%); $^1$H NMR (300 MHz) (CDCl$_3$) δ 9.22 (bs, 1H), 7.65 (s, 1H), 7.26-7.20 (m, 3H), 6.24 (s, 1H), 4.05-4.01 (m, 1H), 2.83-2.54 (m, 4H), 1.67-1.60 (m, 2H), 1.45 (d, J=6 Hz, 3H); LC/MS RT=2.49 (M+H$^+$: 296/298).

The requisite intermediate was prepared as follows:
Step 1)

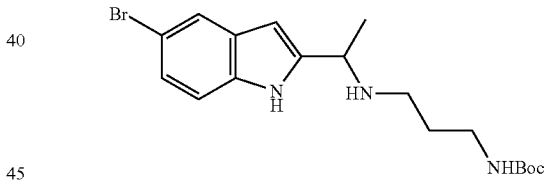

tert-Butyl (3-((1-(5-bromo-1H-indol-2-yl)ethyl)amino)propyl)carbamate 1-(5-Bromo-1H-indol-2-yl)ethan-1-one (500 mg, 2.10 mmol), N-boc propylenediamine (1.10 g, 6.30 mmol) and sodium cyanoborohydride (314 mg, 10.50 mmol) were dissolved in ethanol (20 mL). Catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-100% ethyl acetate/hexane) to give the product as colorless oil (817 mg, 99%); $^1$H NMR (300 MHz) (CDCl$_3$) δ 9.50 (bs, 1H), 7.68 (s, 1H), 7.37-7.26 (m, 3H), 6.43 (s, 1H), 5.04 (m, 1H), 4.35-4.33 (m, 1H), 3.30-3.28 (m, 2H), 2.80-2.76 (m, 2H), 1.85-1.80 (m, 2H), 1.75 (d, J=7 Hz, 3H), 1.46 (s, 9H).

Example 25. Preparation of N-(3-((1-(5-bromo-1H-indol-2-yl)ethyl)amino)propyl)-4,5-dichlorothiophene-2-carboxamide

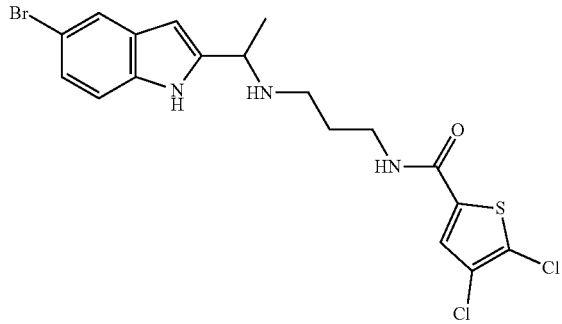 [SMILES: CC(NCCCNC(=O)c1cc(Cl)c(Cl)s1)c1cc2cc(Br)ccc2[nH]1]

N-(3-((1-(5-Bromo-1H-indol-2-yl)ethyl)amino)propyl)-4,5-dichlorothiophene-2-carboxamide 4,5-Dichlorothiophene-2-carboxylic acid (162 mg, 0.82 mmol), EDC hydrochloric acid (157 mg, 0.82 mmol), HOBt (55 mg, 0.41 mmol) and DIPEA (0.23 mL, 1.26 mmol) were dissolved in DMF (5 mL). After 5 minutes of stirring, $N^1$-(1-(5-bromo-1H-indol-2-yl)ethyl)propane-1,3-diamine (120 mg, 0.41 mmol) was added, and it was stirred overnight at room temperature. The reaction mixture was diluted with ethyl acetate, and it was washed with 1N hydrochloric acid, 10% sodium hydroxide and brine. The organic layer was dried over sodium sulfate. The organic layer was concentrated under reduced pressure. The residue was purified on an ISCO chromatograph (0-10% methanol/dichloromethane+0.1% $NH_4OH$) to give the product as a white solid (63 mg, 32%); $^1H$ NMR (300 MHz) ($CDCl_3$) δ 8.88 (bs, 1H), 7.64 (s, 1H), 7.26-7.12 (m, 3H), 7.06 (bs, 1H), 6.26 (s, 1H), 4.04-3.98 (m, 1H), 3.65-3.58 (m, 1H), 3.49-3.40 (m, 1H), 2.75-2.69 (m, 1H), 2.63-2.57 (m, 1H) 1.74-1.68 (m, 2H), 1.49 (d, J=7 Hz, 3H); LC/MS RT=3.05 (M+H⁺: 474/476/478).

Example 26. Preparation of N-(3-((1-(5-bromo-1H-indol-2-yl)ethyl)amino)propyl)-4,5-dichlorothiophene-2-carboxamide

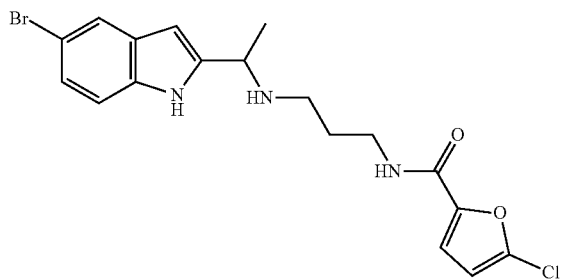

N-(3-((1-(5-Bromo-1H-indol-2-yl)ethyl)amino)propyl)-5-chlorofuran-2-carboxamide

5-Chlorofuran-2-carboxylic acid (120 mg, 0.82 mmol), EDC hydrochloric acid (157 mg, 0.82 mmol), HOBt (55 mg, 0.41 mmol) and DIPEA (0.23 mL, 1.26 mmol) were dissolved in DMF (5 mL). After 5 minutes of stirring, $N^1$-(1-(5-bromo-1H-indol-2-yl)ethyl)propane-1,3-diamine (120 mg, 0.41 mmol) was added, and it was stirred overnight at room temperature. The reaction mixture was diluted with ethyl acetate, and it was washed with 1N hydrochloric acid, 10% sodium hydroxide and brine. The organic layer was dried over sodium sulfate. The organic layer was concentrated under reduced pressure. The residue was purified on an ISCO chromatograph (0-10% methanol/dichloromethane+0.1% $NH_4OH$) to give the product as a white solid (54 mg, 31%); $^1H$ NMR (300 MHz) ($CDCl_3$) δ 9.02 (bs, 1H), 7.63 (s, 1H), 7.18 (m, 2H), 7.11 (d, J=3 Hz, 1H), 7.05 (bs, 1H), 6.32 (d, J=3 Hz, 1H), 6.24 (s, 1H), 4.03-3.98 (m, 1H), 3.76-3.69 (m, 1H), 3.51-3.35 (m, 1H), 2.73-2.68 (m, 1H), 2.60-2.54 (m, 1H), 1.72-1.69 (m, 2H), 1.49 (d, J=6 Hz, 3H); LC/MS RT=2.95 (M+H⁺: 424/426/428).

Example 27. Preparation of N-(3-((1-(5-bromo-1H-indol-2-yl)ethyl)amino)propyl)-5-chlorothiophene-2-carboxamide

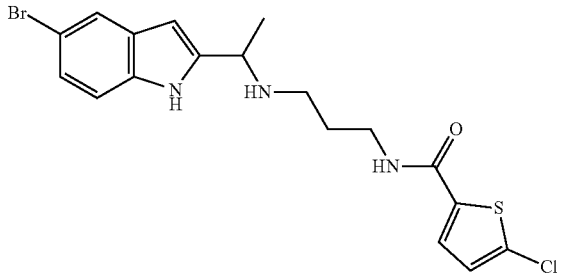 [SMILES: CC(NCCCNC(=O)c1ccc(Cl)s1)c1cc2cc(Br)ccc2[nH]1]

N-(3-((1-(5-Bromo-1H-indol-2-yl)ethyl)amino)propyl)-5-chlorothiophene-2-carboxamide 5-Chlorothiophene-2-carboxylic acid (249 mg, 1.53 mmol), EDC hydrochloric acid (196 mg, 1.02 mmol), HOBt (69 mg, 0.51 mmol) and DIPEA (0.27 mL, 1.53 mmol) were dissolved in DMF (2 mL). After 5 minutes of stirring, $N^1$-(1-(5-bromo-1H-indol-2-yl)ethyl)propane-1,3-diamine (150 mg, 0.51 mmol) was added, and it was stirred overnight at room temperature. The reaction mixture was diluted with ethyl acetate, and it was washed with 1N hydrochloric acid, 10% sodium hydroxide and brine. The organic layer was dried over sodium sulfate. The organic layer was concentrated under reduced pressure. The residue was purified on an ISCO chromatograph (0-10% methanol/dichloromethane+0.1% $NH_4OH$) to give the product as a white solid (29 mg, 13%); $^1H$ NMR (300 MHz) ($CDCl_3$) δ 9.07 (bs, 1H), 7.64 (s, 1H), 7.26-7.06 (m, 2H), 6.79-6.78 (m, 2H), 6.26 (s, 1H), 4.05-4.00 (m, 1H), 3.66-3.60 (m, 1H), 3.51-3.39 (m, 1H), 2.75-2.71 (m, 1H), 2.62-2.54 (m, 1H) 1.73-1.70 (m, 2H), 1.51 (d, J=7 Hz, 3H); LC/MS RT=3.05 (M+H⁺: 440/442/444).

Example 28. Preparation of N-(2-bromo-5,6,7,8,9,10-hexahydrocyclohepta[b]indol-6-yl)propane-1,3-diamine

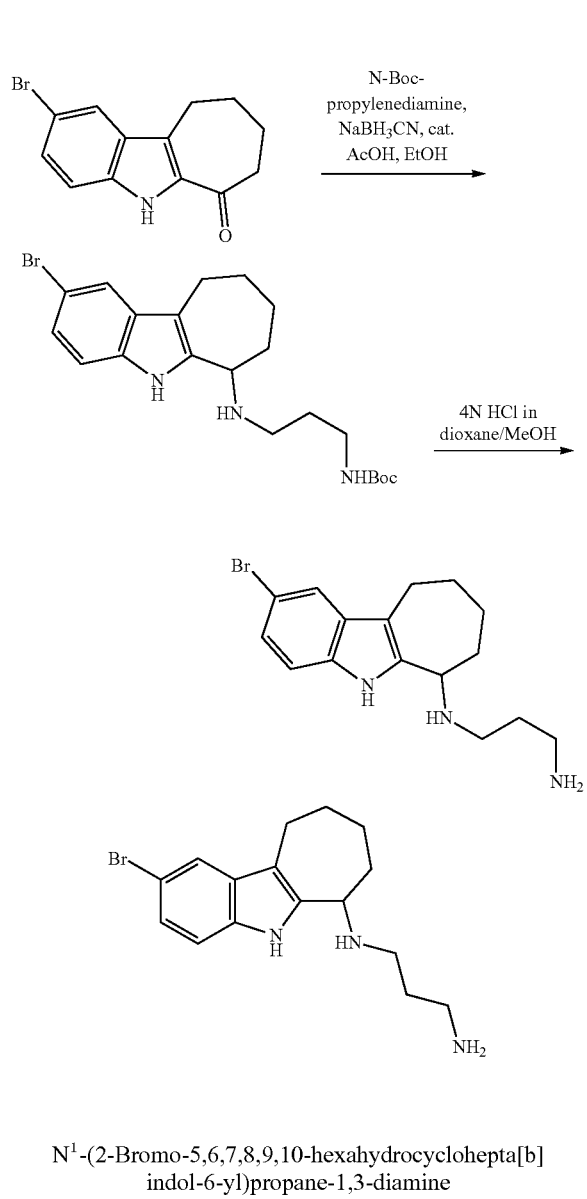

N¹-(2-Bromo-5,6,7,8,9,10-hexahydrocyclohepta[b]indol-6-yl)propane-1,3-diamine

To a solution of tert-butyl (3-((2-bromo-5,6,7,8,9,10-hexahydrocyclohepta[b]indol-6-yl)amino)propyl)carbamate (614 mg, 1.41 mmol) in methanol (3 mL), 4N HCl in dioxane (6 mL, 24 mmol) was added. The reaction mixture was stirred for 1.0 hour at room temperature. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as yellow oil (202 mg, 43%); $^1$H NMR (300 MHz) (CDCl$_3$) δ 10.02 (bs, 1H), 7.58 (s, 1H), 7.15-7.14 (m, 2H), 3.87-3.83 (m, 1H), 2.96-2.75 (m, 6H), 2.63-2.51 (m, 1H), 2.12-2.02 (m, 2H), 1.94-1.88 (m, 1H), 1.74-1.62 (m, 4H); LC/MS RT=2.52 (M+H$^+$: 336/338).

The requisite intermediate was prepared as follows:
Step 1)

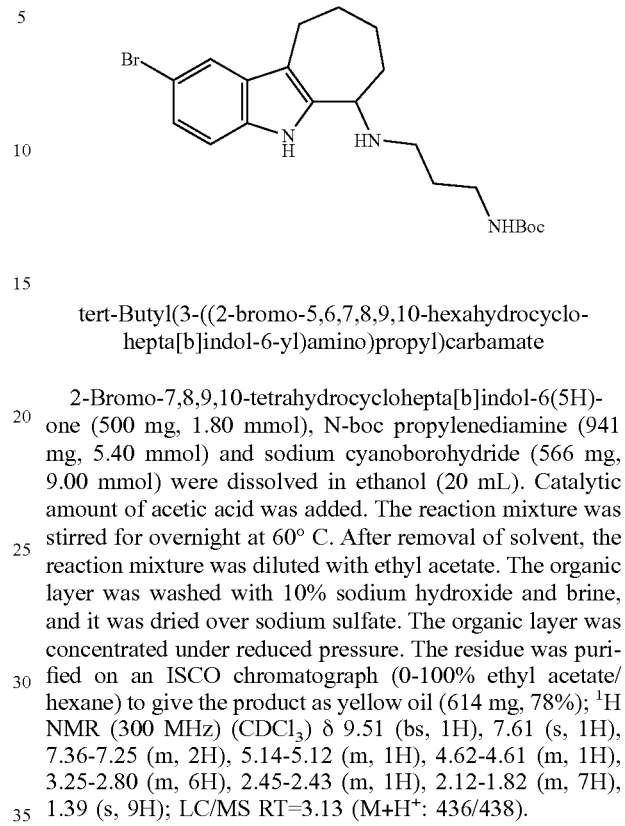

tert-Butyl(3-((2-bromo-5,6,7,8,9,10-hexahydrocyclohepta[b]indol-6-yl)amino)propyl)carbamate 2-Bromo-7,8,9,10-tetrahydrocyclohepta[b]indol-6(5H)-one (500 mg, 1.80 mmol), N-boc propylenediamine (941 mg, 5.40 mmol) and sodium cyanoborohydride (566 mg, 9.00 mmol) were dissolved in ethanol (20 mL). Catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-100% ethyl acetate/hexane) to give the product as yellow oil (614 mg, 78%); $^1$H NMR (300 MHz) (CDCl$_3$) δ 9.51 (bs, 1H), 7.61 (s, 1H), 7.36-7.25 (m, 2H), 5.14-5.12 (m, 1H), 4.62-4.61 (m, 1H), 3.25-2.80 (m, 6H), 2.45-2.43 (m, 1H), 2.12-1.82 (m, 7H), 1.39 (s, 9H); LC/MS RT=3.13 (M+H$^+$: 436/438).

Example 29. Preparation of N¹-(7-bromo-1,2,3,4-tetrahydrocyclopenta[b]indol-3-yl)propane-1,3-diamine

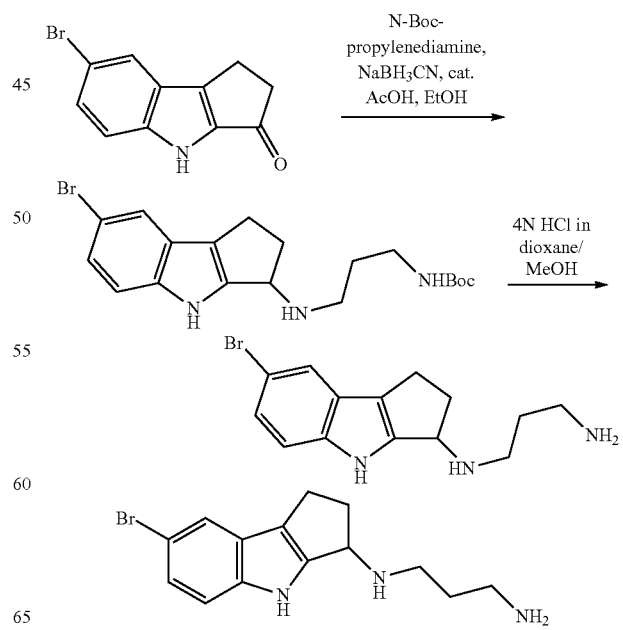

131

N¹-(7-Bromo-1,2,3,4-tetrahydrocyclopenta[b]indol-3-yl)propane-1,3-diamine

To a solution of tert-butyl (3-((7-bromo-1,2,3,4-tetrahydrocyclopenta[b]indol-3-yl)amino)propyl)carbamate (817 mg, 2.00 mmol) in methanol (3 mL), 4N HCl in dioxane (6 mL, 24 mmol) was added. The reaction mixture was stirred for an hour at room temperature. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as a white solid (616 mg, 100%); $^1$H NMR (300 MHz) (CDCl$_3$) δ 9.25 (bs, 1H), 7.58 (s, 1H), 7.26-7.18 (m, 2H), 4.37-4.33 (m, 1H), 2.88-2.65 (m, 8H), 2.12-2.04 (m, 1H), 2.04-1.97 (m, 2H); LC/MS RT=2.50 (M+H$^+$: 308/310).

The requisite intermediate was prepared as follows:
Step 1)

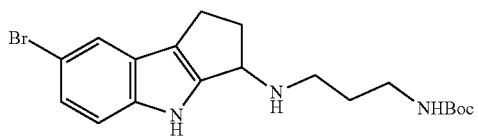 [SMILES: CC(C)(C)OC(=O)NCCCNC1CCc2c1[nH]c1ccc(Br)cc21]

tert-Butyl (3-((7-bromo-1,2,3,4-tetrahydrocyclopenta[b]indol-3-yl)amino)propyl)carbamate 7-Bromo-1,4-dihydrocyclopenta[b]indol-3(2H)-one (500 mg, 2.00 mmol), N-boc propylenediamine (1.05 g, 6.00 mmol) and sodium cyanoborohydride (628 mg, 10.00 mmol) were dissolved in ethanol (20 mL). Catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-100% ethyl acetate/hexane) to give the product as a foamy yellow solid (817 mg, 100%); $^1$H NMR (300 MHz) (CDCl$_3$) δ 9.16 (bs, 1H), 7.63 (s, 1H), 7.33-7.32 (m, 2H), 5.07-5.03 (m, 1H), 4.83 (m, 1H), 3.26-3.24 (m, 2H), 3.04-2.85 (m, 5H), 2.60-2.54 (m, 1H), 1.98-1.96 (m, 2H), 1.39 (s, 9H); LC/MS RT=3.08 (M+H$^+$: 408/410).

Example 30. Preparation of N-(3-((1-(5-bromo-1H-indol-2-yl)ethyl)amino)propyl)-3,4-dichlorobenzamide

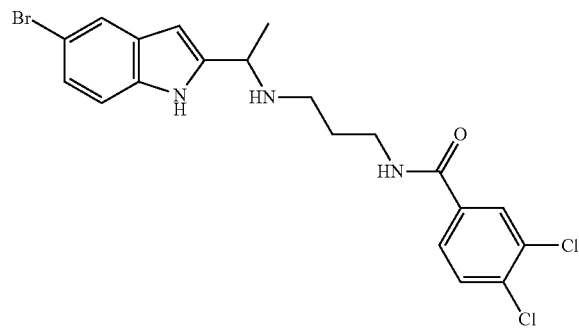 [SMILES: CC(NCCCNC(=O)c1ccc(Cl)c(Cl)c1)c1cc2cc(Br)ccc2[nH]1]

132

N-(3-((1-(5-Bromo-1H-indol-2-yl)ethyl)amino)propyl)-3,4-dichlorobenzamide 3,4-Dichlorobenzoic acid (32 mg, 0.17 mmol), EDC hydrochloric acid (65 mg, 0.34 mmol), HOBt (23 mg, 0.17 mmol) and DIPEA (0.09 mL, 0.51 mmol) were dissolved in dichloromethane (5 mL). After 5 minutes of stirring, N-(1-(5-bromo-1H-indol-2-yl)ethyl)propane-1,3-diamine (50 mg, 0.17 mmol) was added, and it was stirred overnight at room temperature. The reaction mixture was diluted with ethyl acetate, and it was washed with 1N hydrochloric acid, 10% sodium hydroxide and brine. The organic layer was dried over sodium sulfate. The organic layer was concentrated under reduced pressure. The residue was purified on an ISCO chromatograph (0-10% methanol/dichloromethane+0.1% NH$_4$OH) to give the product as colorless oil (14 mg, 18%); $^1$H NMR (300 MHz) (CDCl$_3$) δ 9.97 (bs, 1H), 7.88 (d, J=2 Hz, 1H), 7.64 (s, 1H), 7.53 (dd, J=8 Hz, J=2 Hz, 2H), 7.42 (d, J=8 Hz, 1H), 7.25-7.18 (m, 2H), 4.35-4.28 (m, 1H), 3.63-3.48 (m, 2H), 2.81-2.69 (m, 2H), 1.94-1.90 (m, 2H), 1.72 (d, J=7 Hz, 3H); LC/MS RT=3.12 (M+H$^+$: 468/470/472).

Example 31. Preparation of N-(3-((1-(5-bromo-1H-indol-2-yl)ethyl)amino)propyl)-cyclohexanecarboxamide

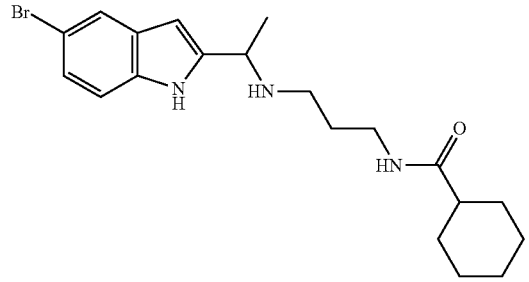 [SMILES: CC(NCCCNC(=O)C1CCCCC1)c1cc2cc(Br)ccc2[nH]1]

N-(3-((1-(5-Bromo-1H-indol-2-yl)ethyl)amino)propyl)cyclohexanecarboxamide

Cyclohexane carboxylic acid (22 mg, 0.17 mmol), EDC hydrochloric acid (65 mg, 0.34 mmol), HOBt (23 mg, 0.17 mmol) and DIPEA (0.09 mL, 0.51 mmol) were dissolved in dichloromethane (5 mL). After 5 minutes of stirring, N¹-(1-(5-bromo-1H-indol-2-yl)ethyl)propane-1,3-diamine (50 mg, 0.17 mmol) was added, and it was stirred overnight at room temperature. The reaction mixture was diluted with ethyl acetate, and it was washed with 1N hydrochloric acid, 10% sodium hydroxide and brine. The organic layer was dried over sodium sulfate. The organic layer was concentrated under reduced pressure. The residue was purified on an ISCO chromatograph (0-10% methanol/dichloromethane+0.1% NH$_4$OH) to give the product as colorless oil (55 mg, 80%); $^1$H NMR (300 MHz) (CDCl$_3$) δ 9.28 (bs, 1H), 7.64 (d, J=2 Hz, 1H), 7.26 (d, J=9 Hz, 1H), 7.19 (dd, J=8 Hz, J=2 Hz, 1H), 6.23 (d, J=1 Hz, 1H), 5.68 (bs, 1H), 4.00-3.96 (m, 1H), 3.54-3.47 (m, 1H), 3.27-3.20 (m, 1H), 2.62-2.54 (m, 1H), 2.49-2.41 (m, 1H), 2.04-2.00 (m, 1H), 1.79-1.57 (m, 6H), 1.47 (d, J=7 Hz, 3H), 1.38-1.14 (m, 6H); LC/MS RT=2.88 (M+H$^+$: 406/408).

Example 32. Preparation of N-(1-(5-bromo-1H-indol-2-yl)ethyl)butan-1-amine

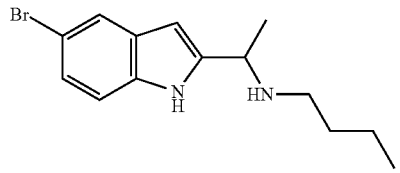 [SMILES: CCCCNC(C)c1cc2cc(Br)ccc2[nH]1]

N-(1-(5-Bromo-1H-indol-2-yl)ethyl)butan-1-amine 1-(5-Bromo-1H-indol-2-yl)ethan-1-one (100 mg, 0.42 mmol), n-butylamine (0.42 mL, 4.20 mmol) and sodium cyanoborohydride (132 mg, 2.10 mmol) were dissolved in ethanol (50 mL). Catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-100% ethyl acetate/hexane) to give the product as colorless oil (94 mg, 76%); $^1$H NMR (300 MHz) (CDCl$_3$) δ 8.83 (bs, 1H), 7.67 (s, 1H), 7.26-7.23 (m, 2H), 6.29 (s, 1H), 4.14-4.07 (m, 1H), 2.64-2.50 (m, 2H), 1.51 (d, J=7 Hz, 3H), 1.47-1.44 (m, 2H), 1.36-1.29 (m, 2H), 0.89 (t, J=7 Hz, 3H); LC/MS RT=2.79 (M+H$^+$: 295/297).

Example 33. Preparation of 1-(5-bromo-1H-indol-2-yl)-N-phenethylethan-1-amine

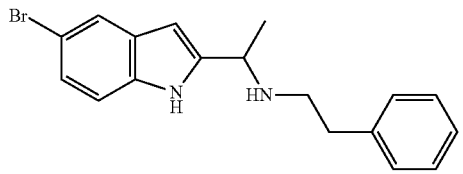 [SMILES: CC(NCCc1ccccc1)c1cc2cc(Br)ccc2[nH]1]

1-(5-Bromo-1H-indol-2-yl)-N-phenethylethan-1-amine 1-(5-Bromo-1H-indol-2-yl)ethan-1-one (100 mg, 0.42 mmol), phenethylamine (0.53 mL, 4.20 mmol) and sodium cyanoborohydride (132 mg, 2.10 mmol) were dissolved in ethanol (50 mL). A catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-100% ethyl acetate/hexane) to give the product as colorless oil (47 mg, 33%); $^1$H NMR (300 MHz) (CDCl$_3$) δ 8.41 (bs, 1H), 7.63 (d, J=2 Hz, 1H), 7.34-7.11 (m, 6H), 7.10 (d, J=9 Hz, 1H), 6.21 (d, J=2 Hz, 1H), 4.06-4.00 (m, 1H), 2.92-2.84 (m, 1H), 2.79-2.71 (m, 3H), 1.40 (d, J=7 Hz, 3H); LC/MS RT=3.02 (M+H$^+$: 343/345).

Example 34. Preparation of N-(2-((1-(5-bromo-1H-indol-2-yl)ethyl)amino)ethyl)-3,4-dichlorobenzamide

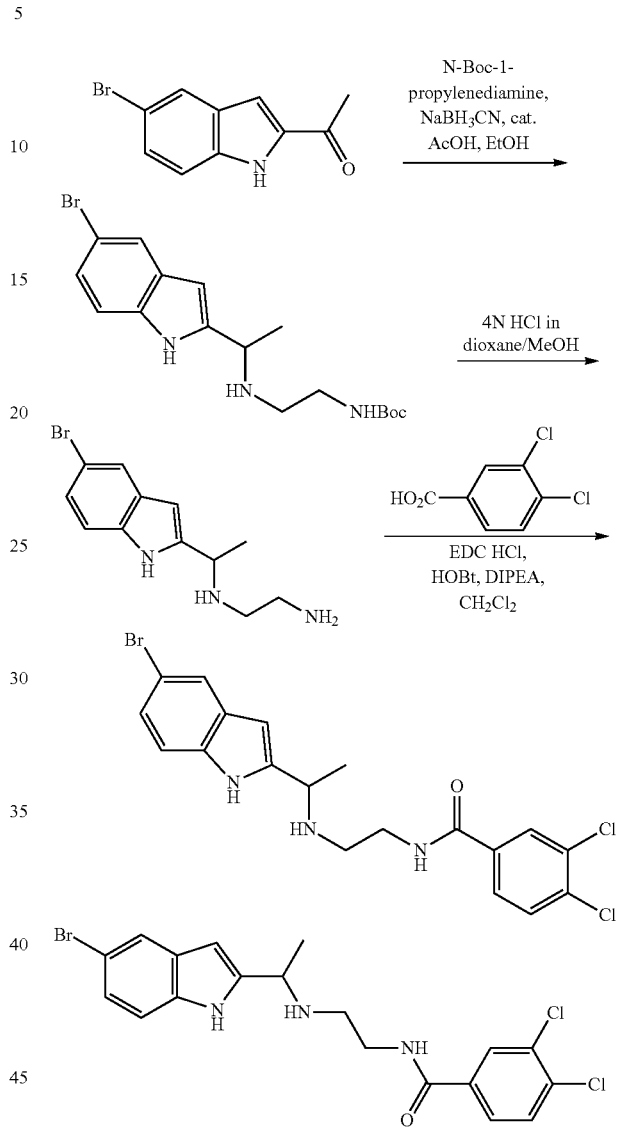

N-(2-((1-(5-Bromo-1H-indol-2-yl)ethyl)amino)ethyl)-3,4-dichlorobenzamide 3,4-Dichlorobenzoic acid (66 mg, 0.35 mmol), EDC hydrochloric acid (134 mg, 0.70 mmol), HOBt (47 mg, 0.35 mmol) and DIPEA (0.19 mL, 1.05 mmol) were dissolved in dichloromethane (10 mL). After 5 minutes of stirring, N$^1$-(1-(5-bromo-1H-indol-2-yl)ethyl)ethane-1,2-diamine (100 mg, 0.35 mmol) was added, and it was stirred overnight at room temperature. The reaction mixture was diluted with ethyl acetate, and it was washed with 1N hydrochloric acid, 10% sodium hydroxide and brine. The organic layer was dried over sodium sulfate. The organic layer was concentrated under reduced pressure. The residue was purified on an ISCO chromatograph (0-10% methanol/dichloromethane+0.1% NH$_4$OH) to give the product as colorless oil (38 mg, 24%); $^1$H NMR (300 MHz) (CDCl$_3$) δ 8.81 (bs, 1H), 7.83 (s, 1H), 7.65 (s, 1H), 7.49-7.46 (m, 2H), 7.23-7.13 (m, 2H), 6.49 (bs, 1H), 6.27 (s, 1H), 4.11-4.05 (m, 1H), 3.54-3.44 (m, 2H), 2.91-2.72 (m, 2H), 1.48 (d, J=7 Hz, 3H); LC/MS RT=3.04 (M+H$^+$:454/456/458).

The requisite intermediate was prepared as follows:

Step 1)

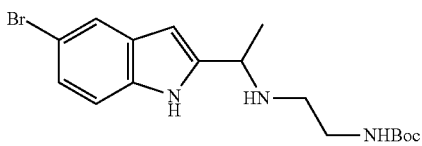 [SMILES: CC(NCCNC(=O)OC(C)(C)C)c1cc2cc(Br)ccc2[nH]1]

tert-Butyl (2-((1-(5-bromo-1H-indol-2-yl)ethyl)amino)ethyl)carbamate 1-(5-Bromo-1H-indol-2-yl)ethan-1-one (300 mg, 1.26 mmol), N-boc-1-ethylenediamine (0.59 mL, 3.78 mmol) and sodium cyanoborohydride (396 mg, 6.30 mmol) were dissolved in ethanol (10 mL). A catalytic amount of acetic acid was added. The reaction mixture was stirred for overnight at 60° C. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-100% ethyl acetate/hexane) to give the product as colorless oil (482 mg, 100%); $^1$H NMR (300 MHz) (CDCl$_3$) δ 9.33 (bs, 1H), 7.67 (s, 1H), 7.30-7.26 (m, 2H), 6.39 (d, J=2 Hz, 1H), 5.10 (m, 1H), 4.39-4.35 (m, 1H), 3.30-3.28 (m 2H), 2.88-2.86 (m, 2H), 1.66 (d, J=6 Hz, 3H), 1.44 (s, 9H).

Step 2)

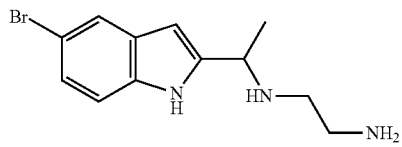 [SMILES: CC(NCCN)c1cc2cc(Br)ccc2[nH]1]

N$^1$-(1-(5-Bromo-1H-indol-2-yl)ethyl)ethane-1,2-diamine

To a solution of tert-butyl (2-((1-(5-bromo-1H-indol-2-yl)ethyl)amino)ethyl)carbamate (482 mg, 1.26 mmol) in methanol (2 mL), 4N HCl in dioxane (4 mL, 16 mmol) was added. The reaction mixture was stirred for an hour at room temperature. After removal of solvent, the reaction mixture was diluted with ethyl acetate. The organic layer was washed with 10% sodium hydroxide and brine, and it was dried over sodium sulfate. The organic layer was concentrated under reduced pressure. The residue was purified on an ISCO chromatograph (0-10% methanol/dichloromethane+0.1% NH$_4$OH) to give the product as colorless oil (351 mg, 99%); $^1$H NMR (300 MHz) (CDCl$_3$) δ 9.09 (bs, 1H), 7.65 (s, 1H), 7.20-7.19 (m, 2H), 6.24 (s, 1H), 4.07-4.01 (m, 1H), 2.82-2.67 (m, 3H), 2.58-2.51 (m, 1H), 1.46 (d, J=6 Hz, 3H).

Example 35. Preparation of 1-(5-bromo-H-indol-2-yl)-N-(cyclopropylmethyl)ethan-1-amine

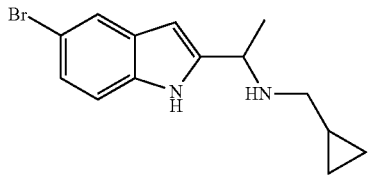 [SMILES: CC(NCC1CC1)c1cc2cc(Br)ccc2[nH]1]

1-(5-Bromo-1H-indol-2-yl)-N-(cyclopropylmethyl)ethan-1-amine

To a solution of 1-(5-bromo-1H-indol-2-yl)ethan-1-one (190 mg, 0.80 mmol) in ethanol (10 mL), cyclopropanemethylamine hydrochloride (452 mg, 4.20 mmol), sodium cyanoborohydride (132 mg, 2.19 mmol), and DIPEA (0.73 mL, 4.20 mmol) were added. The reaction mixture was stirred for 60° C. for 24 hours. The mixture was diluted with ethyl acetate, and the organic layer was washed with 10% sodium hydroxide, saturated ammonium chloride, and brine. The organic layer was then dried over sodium sulfate, and it was concentrated under reduced pressure. The residue was purified on an ISCO chromatograph (10% methanol/dichloromethane+1% NH$_4$OH) to give product as colorless oil (30 mg, 24%); $^1$H NMR (300 MHz, CDCl$_3$) δ 9.34 (bs, 1H), 7.70 (s, 1H), 7.33-7.24 (m, 2H), 6.48 (s, 1H), 4.62-4.55 (m, 1H), 2.71-2.57 (m, 2H), 1.84 (d, J=6 Hz, 3H), 1.11-1.04 (m, 1H), 0.71-0.64 (m, 1H), 0.31-0.26 (m, 1H); LC/MS RT=2.88 (M+H$^+$: 293/295).

Example 36. Preparation of 1-(5-bromo-1H-indol-2-yl)-3-phenylpropan-1-amine

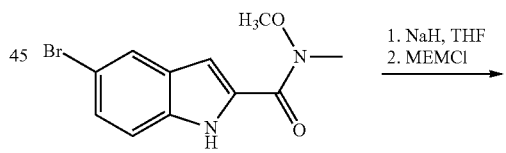

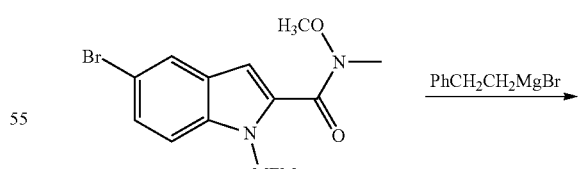

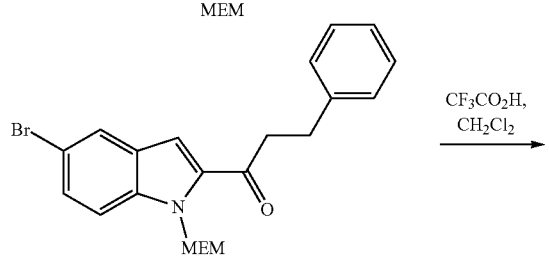

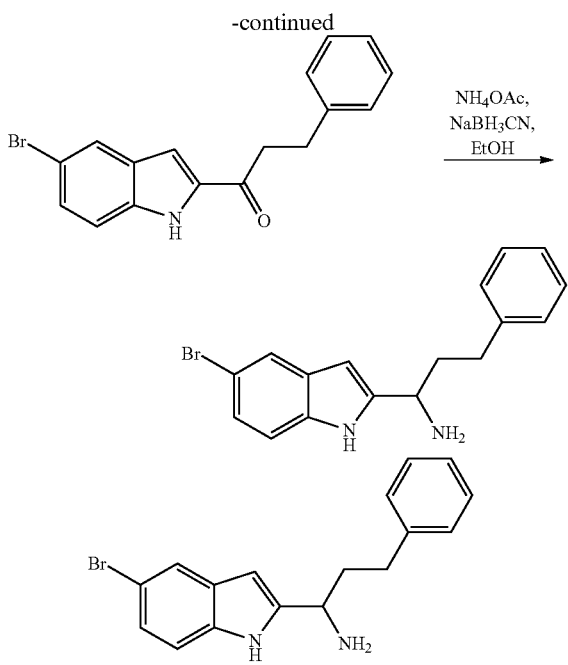

1-(5-Bromo-1H-indol-2-yl)-3-phenylpropan-1-amine

To a solution of 1-(5-bromo-1H-indol-2-yl)-3-phenylpropan-1-one (50 mg, 0.15 mmol) in ethanol (10 mL), ammonium acetate (115 mg, 1.50 mmol) and sodium cyanoborohydride (47 mg, 0.75 mmol) were added. The reaction mixture was stirred for overnight at 60° C. After removal of solvent, the reaction mixture was diluted with ethyl acetate. The organic layer was washed with 10% sodium hydroxide and brine, and it was then dried over sodium sulfate. The organic layer was concentrated under reduced pressure. The residue was purified on an ISCO chromatograph (0-10% methanol/dichloromethane+0.1% NH$_4$OH) to give product as colorless oil (47 mg, 96%); $^1$H NMR (300 MHz) (CDCl$_3$) δ 8.87 (bs, 1H), 7.62 (s, 1H), 7.24-7.15 (m, 5H), 7.08 (d, J=7 Hz, 2H), 6.40 (s, 1H), 4.24 (m, 1H), 2.52-2.46 (m, 2H), 2.29-2.26 (m, 2H); LC/MS RT=3.00 (M−H$^-$: 327/329).
The requisite intermediate was prepared as follows:
Step 1)

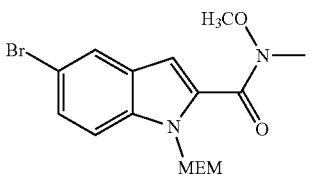

5-Bromo-N-methoxy-1-((2-methoxyethoxy)methyl)-N-methyl-1H-indole-2-carboxamide

To a solution of 5-bromo-N-methoxy-N-methyl-1H-indole-2-carboxamide (100 mg, 0.35 mmol) in tetrahydrofuran (10 mL), sodium hydride (60% dispersed in oil, 28 mg, 0.70 mmol) was added at 0° C. Then MEM chloride (79 μL, 0.70 mmol) was added at 0° C. The reaction mixture was stirred for an hour at 0° C. The mixture was quenched with water, and it was diluted with ethyl acetate. The organic layer was washed with saturated ammonium chloride and brine. The organic layer was dried over sodium sulfate, and it was concentrated under reduced pressure. The residue was purified on an ISCO chromatograph (0-50% ethyl acetate/hexane) to give product as colorless oil (121 mg, 93%); $^1$H NMR (300 MHz) (CDCl$_3$) δ 7.74 (s, 1H), 7.46-7.40 (m, 2H), 7.03 (s, 1H), 5.86 (s, 2H), 3.66 (s, 3H), 3.64-3.51 (m, 2H), 3.44-3.38 (m, 5H), 3.30 (m, 3H).

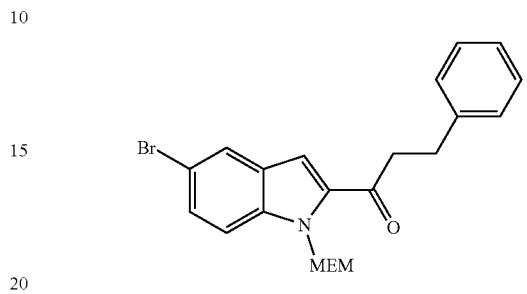

1-(5-Bromo-1-((2-methoxyethoxy)methyl)-1H-indol-2-yl)-3-phenylpropan-1-one

To a solution of 5-bromo-N-methoxy-1-((2-methoxyethoxy)methyl)-N-methyl-1H-indole-2-carboxamide (657 mg, 1.77 mmol) in tetrahydrofuran (20 mL), 1.0M phenylethyl magnesium bromide (8.85 mL, 8.85 mmol) was added at 0° C. The reaction mixture was stirred for an hour at 0° C. After the mixture was quenched with water, it was poured onto ethyl acetate. The organic layer was washed with saturated ammonium chloride and brine. The organic layer was then dried over sodium sulfate, and it was concentrated under reduced pressure. The resulting residue was purified on an ISCO chromatograph (0-20% ethyl acetate/hexane) to give product as colorless oil (509 mg, 69%); $^1$H NMR (300 MHz) (CDCl$_3$) δ 7.79 (s, 1H), 7.47-7.46 (m, 2H), 7.31-7.21 (m, 6H), 6.07 (s, 2H), 3.57-3.54 (m, 2H), 3.45-3.42 (m, 2H), 3.30-3.31 (m, 5H), 3.11-3.05 (m, 2H).
Step 3)

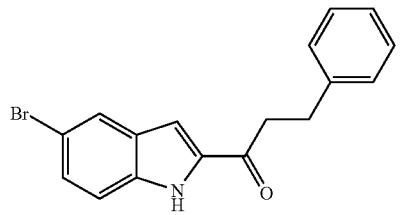 [SMILES: O=C(CCc1ccccc1)c1cc2cc(Br)ccc2[nH]1]

1-(5-Bromo-1H-indol-2-yl)-3-phenylpropan-1-one

To a solution of 1-(5-bromo-1-((2-methoxyethoxy)methyl)-1H-indol-2-yl)-3-phenylpropan-1-one (250 mg, 0.60 mmol) in dichloromethane (2 mL), trifluoroacetic acid (2 mL) was added at room temperature. The reaction mixture was stirred for 30 minutes at room temperature. After removal of solvent, it was diluted with ethyl acetate. The organic layer was washed with 10% sodium hydroxide followed by brine. The organic layer was dried over sodium sulfate, and it was concentrated under reduced pressure. The resulting residue was purified on an ISCO chromatograph (0-10% ethyl acetate/hexane) to give product as a white solid (51 mg, 26%); $^1$H NMR (300 MHz) (CDCl$_3$) δ 9.21

(bs, 1H), 7.83 (s, 1H), 7.42 (dd, J=9 Hz, J=2 Hz, 1H), 7.33-7.22 (m, 6H), 7.10 (s, 1H), 3.31-3.26 (m, 2H), 3.13-3.08 (m, 2H).

Example 37. Preparation of 4-((1-(5-bromo-1H-indol-2-yl)ethyl)amino)-N-(3,4-dichlorophenyl)butanamide

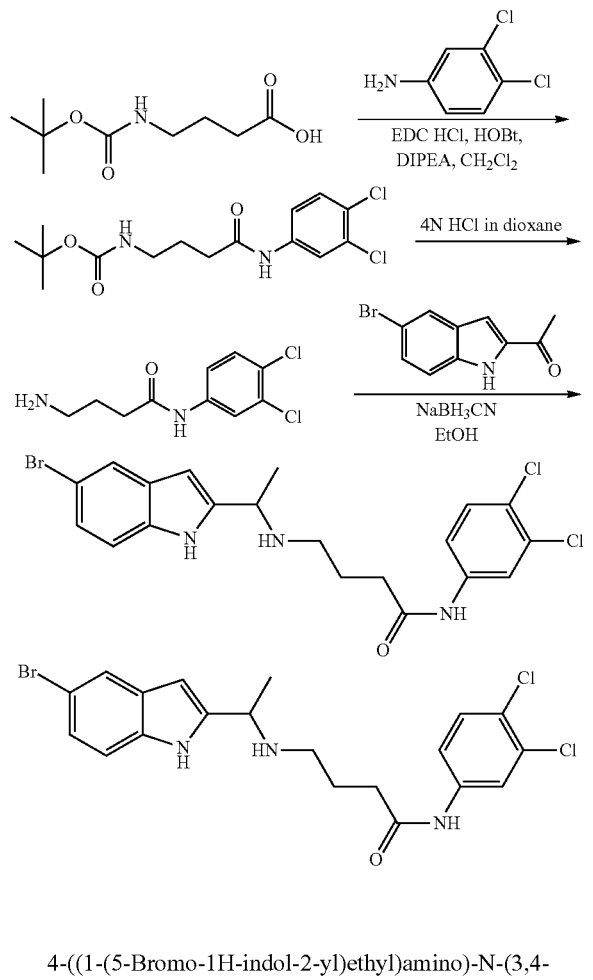

4-((1-(5-Bromo-1H-indol-2-yl)ethyl)amino)-N-(3,4-dichlorophenyl)butanamide

To a solution of 1-(5-bromo-1H-indol-2-yl)ethan-1-one (243 mg, 1.02 mmol) in ethanol (10 mL), 4-amino-N-(3,4-dichlorophenyl)butanamide (253 mg, 1.02 mmol) and sodium cyanoborohydride (320 mg, 5.10 mmol) were added. The reaction mixture was stirred for 60° C. for 24 hours. The mixture was diluted with ethyl acetate, and the organic layer was washed with 10% sodium hydroxide, saturated ammonium chloride, and brine. The organic layer was then dried over sodium sulfate, and it was concentrated under reduced pressure. The residue was purified on an ISCO chromatograph (10% methanol/dichloromethane+1% NH$_4$OH) to give product as colorless oil (73 mg, 15%); $^1$H NMR (300 MHz, DMSO-d$_6$) δ 11.30 (bs, 1H), 10.25 (bs, 1H), 8.00-7.99 (m, 1H), 7.72 (s, 1H), 7.60-7.55 (m, 1H), 7.49-7.44 (m, 1H), 7.38-7.36 (m, 1H), 7.23-7.21 (m, 1H), 6.48 (s, 1H), 4.33 (m, 1H), 2.76-2.60 (m, 2H), 2.42 (m, 2H), 1.84 (m, 2H), 1.57 (m, 3H).

The requisite intermediate was prepared as follows:

Step 1)

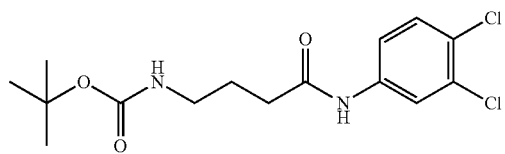 [SMILES: CC(C)(C)OC(=O)NCCCC(=O)Nc1ccc(Cl)c(Cl)c1]

tert-Butyl (4-((3,4-dichlorophenyl)amino)-4-oxobutyl)carbamate

To a solution of 4-((tert-butoxy carbonyl)amino)butanoic acid (1.0 g, 4.9 mmol) in dichloromethane (50 mL), EDC hydrochloric acid (1.98 g, 10.3 mmol), HOBt (665 mg, 4.9 mmol) and DIPEA (1.80 mL, 10.33 mmol) were added. After the mixture stirred for 5 minutes, 3,4-dichloroaniline (797 mg, 4.92 mmol) was added. The mixture was then stirred for overnight at room temperature. The mixture was then diluted with dichloromethane, and the organic layer was washed with 1N hydrochloric acid, 10% sodium hydroxide, saturated ammonium chloride and brine. The organic layer was then dried over sodium sulfate, and it was concentrated under reduced pressure. The residue was purified on an ISCO chromatograph (0-30% ethyl acetate/hexane) to give product as a white solid (757 mg, 44%); $^1$H NMR (300 MHz, CDCl$_3$) δ 9.47 (bs, 1H), 7.92 (s, 1H), 7.48 (d, J=9 Hz, 1H), 7.37 (d, J=9 Hz, 1H), 4.87 (m, 1H), 3.27-3.24 (m, 2H), 2.41-2.37 (m, 2H), 1.89-1.87 (m, 2H), 1.49 (s, 9H).

Step 2)

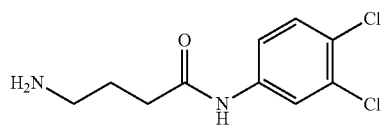 [SMILES: NCCCC(=O)Nc1ccc(Cl)c(Cl)c1]

4-Amino-N-(3,4-dichlorophenyl)butanamide

To a solution of tert-butyl (4-((3,4-dichlorophenyl)amino)-4-oxobutyl)carbamate (500 mg, 1.44 mmol) in methanol (0.36 mL), 4N hydrochloric acid (3.60 mL, 14.40 mmol) was added. The reaction mixture was stirred for 2 hours at room temperature. The mixture was diluted with ethyl acetate, and the organic layer was washed with 10% sodium hydroxide saturated ammonium chloride and brine. The organic layer was then dried over sodium sulfate, and it was concentrated under reduced pressure. The residue was purified on an ISCO chromatograph (0-100% ethyl acetate/hexane followed by 10% methanol/dichloromethane+1% NH$_4$OH) to give product as colorless oil (253 mg, 71%); $^1$H NMR (300 MHz, CDCl$_3$) δ 9.85 (bs, 1H), 7.78 (d, J=2 Hz, 1H), 7.38-7.32 (m, 2H), 2.90-2.86 (m, 2H), 2.54-2.49 (m, 2H), 1.80-1.84 (m, 2H), 1.64 (bs, 2H).

Example 38. Preparation of N-(1-(5-bromo-1H-indol-2-yl)ethyl)-4-(3,4-dichlorophenoxy)butan-1-amine

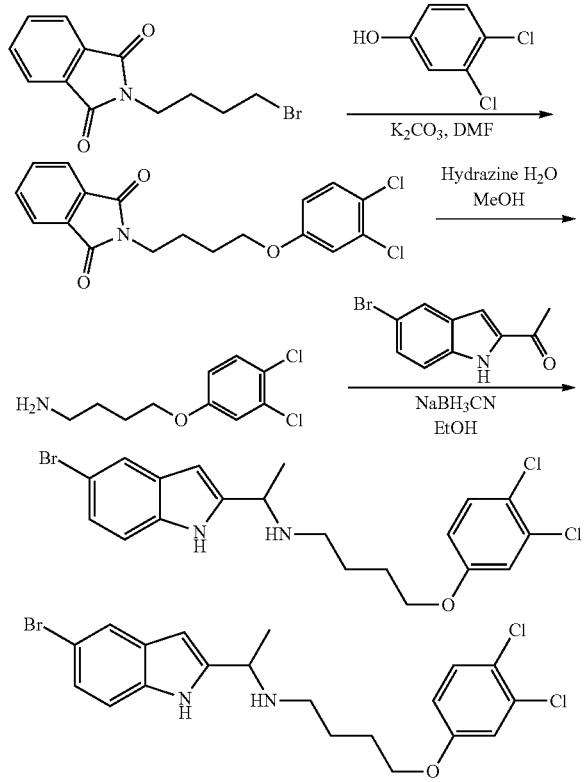

N-(1-(5-Bromo-1H-indol-2-yl)ethyl)-4-(3,4-dichlorophenoxy)butan-1-amine

To a solution of 1-(5-bromo-1H-indol-2-yl)ethan-1-one (190 mg, 0.80 mmol) in ethanol (10 mL), 4-(3,4-dichlorophenoxy)butan-1-amine (187 mg, 0.80 mmol) and sodium cyanoborohydride (251 mg, 4.00 mmol) were added. The reaction mixture was stirred for 60° C. for 24 hours. The mixture was diluted with ethyl acetate, and the organic layer was washed with 10% sodium hydroxide, saturated ammonium chloride and brine. The organic layer was then dried over sodium sulfate, and it was concentrated under reduced pressure. The residue was purified on an ISCO chromatograph (10% methanol/dichloromethane+1% NH$_4$OH) to give product as colorless oil (47 mg, 13%); $^1$H NMR (300 MHz, CDCl$_3$) δ 9.11 (bs, 1H), 7.71 (s, 1H), 7.31-7.28 (m, 3H), 6.91 (s, 1H), 6.62 (d, J=9 Hz, 1H), 6.44 (s, 1H), 4.11-4.39 (m, 1H), 3.87 (m, 2H), 2.78 (m, 2H), 1.81 (m, 4H), 1.72 (d, J=7 Hz, 3H).

The requisite intermediate was prepared as follows:
Step 1)

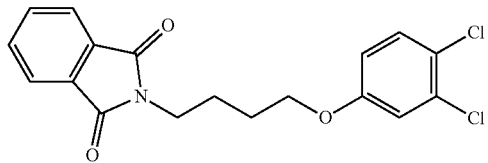 [SMILES: O=C1c2ccccc2C(=O)N1CCCCOc1ccc(Cl)c(Cl)c1]

2-(4-(3,4-Dichlorophenoxy)butyl)isoindoline-1,3-dione

To a solution of 2-(4-bromobutyl)isoindoline-1,3-dione (500 mg, 1.77 mmol) in DMF (5 mL), 3,4-dichlorophenol (289 mg, 1.77 mmol) and potassium carbonate (245 mg, 1.77 mmol) were added. The reaction mixture was stirred for 5 hours at room temperature. The mixture was diluted with ethyl acetate, the organic layer was washed with water and brine. The organic layer was then dried over sodium sulfate, and it was concentrated under reduced pressure. The residue was purified on an ISCO chromatograph (0-30% ethyl acetate/hexane) to give product as colorless oil (545 mg, 84%); $^1$H NMR (300 MHz, CDCl$_3$) δ 7.89-7.86 (m, 2H), 7.76-7.73 (m, 2H), 7.29 (d, J=9 Hz, 1H), 6.98 (d, J=3 Hz, 1H), 6.75 (dd, J=9 Hz, J=3 Hz, 1H), 4.00-3.96 (m, 2H), 3.81-3.77 (m, 2H), 1.89-1.87 (m, 4H).

Step 2)

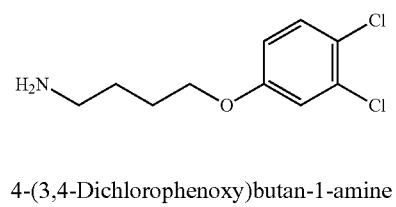

4-(3,4-Dichlorophenoxy)butan-1-amine

To a solution of 2-(4-(3,4-dichlorophenoxy)butyl)isoindoline-1,3-dione (545 mg, 1.50 mmol) in methanol (15 mL), hydrazine monohydrate (0.15 mL, 3.00 mmol) was added at room temperature. The reaction mixture was stirred for 2 hours at 60° C. The white suspension was formed, and the suspension was filtered. The suspension was concentrated under reduced pressure, and the residue was diluted with ethyl acetate. The organic layer was washed with 10% sodium hydroxide and brine. The organic layer was then dried over sodium sulfate, and it was concentrated under reduced pressure. The residue was purified on an ISCO chromatograph (0-100% ethyl acetate/hexane followed by 10% methanol/dichloromethane+1% NH$_4$OH) to give product as colorless oil (187 mg, 53%); $^1$H NMR (300 MHz, CDCl$_3$) δ 7.31 (d, J=9 Hz, 1H), 6.99 (d, J=3 Hz, 1H), 6.75 (dd, J=9 Hz, J=3 Hz, 1H), 3.97-3.92 (m, 2H), 2.80-2.75 (m, 2H), 1.85-1.80 (m, 2H), 1.66-1.58 (m, 2H), 1.23 (bs, 2H).

Example 39. Preparation of N-(1-(5-bromo-1H-indol-2-yl)ethyl)-4-(3,4-dichlorophenoxy)butan-1-amine

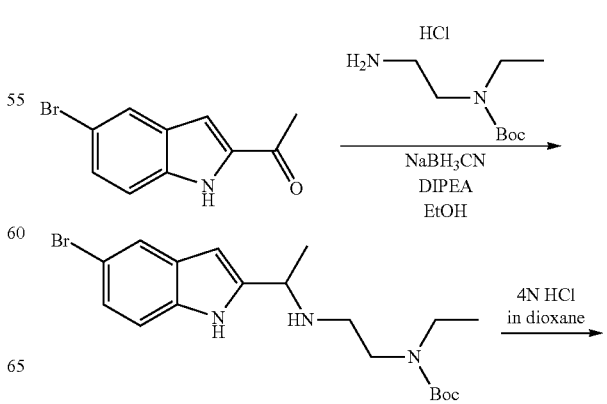

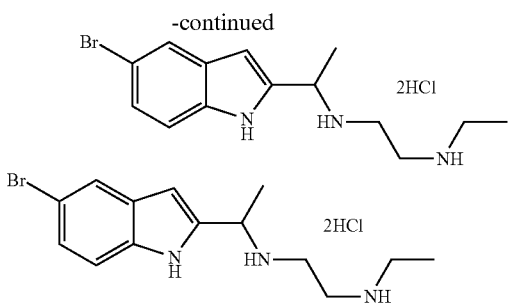

$N^1$-(1-(5-Bromo-1H-indol-2-yl)ethyl)-$N^2$-ethyl-ethane-1,2-diaminehydrochloricacid To a solution of tert-butyl (2-((1-(5-bromo-1H-indol-2-yl)ethyl)amino)ethyl)(ethyl)carbamate (67 mg, 0.16 mmol) in methanol (0.04 mL), 4N hydrochloric acid in dioxane (0.4 mL, 1.6 mmol) was added. The reaction mixture was stirred for 2 hours at room temperature. The mixture was then concentrated under reduced pressure, and the residue was suspended in ethyl acetate. The suspension was filtered to give product as a white solid (47 mg, 77%); $^1$H NMR (300 MHz, $D_2O$) δ 7.77 (s, 1H), 7.35-7.30 (m, 2H), 6.63 (s, 1H), 3.31-3.24 (m, 5H), 3.01-2.95 (m, 2H), 1.74-1.68 (m, 3H), 1.18-1.09 (m, 3H).

The requisite intermediate was prepared as follows:
Step 1)

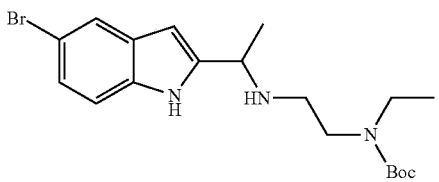 [SMILES: CCN(CCNC(C)c1cc2cc(Br)ccc2[nH]1)C(=O)OC(C)(C)C]

tert-Butyl (2-((1-(5-bromo-1H-indol-2-yl)ethyl)amino)ethyl)(ethyl)carbamate

To a solution of 1-(5-bromo-1H-indol-2-yl)ethan-1-one (105 mg, 0.44 mmol) in ethanol (10 mL), tert-butyl (2-aminoethyl)(ethyl)carbamate hydrochloric acid (100 mg, 0.44 mmol), sodium cyanoborohydride (138 mg, 2.20 mmol), and DIPEA (76 µL, 0.44 mmol) were added. The reaction mixture was stirred for 60° C. for 48 hours. The reaction mixture was diluted with ethyl acetate, and the organic layer was washed with 10% sodium hydroxide, saturated ammonium chloride, and brine. The organic layer was then dried over sodium sulfate, and it was concentrated under reduced pressure. The residue was purified on an ISCO chromatograph (10% methanol/dichloromethane+1% $NH_4OH$) to give product as colorless oil (67 mg, 37%); $^1$H NMR (300 MHz, $CDCl_3$) δ 9.41 (bs, 1H), 7.67 (s, 1H), 7.23 (m, 2H), 6.29 (s, 1H), 4.15-4.11 (m, 1H), 3.51-3.21 (m, 5H), 2.77 (m, 2H), 2.38 (m, 2H), 1.51 (s, 9H), 1.38 (t, J=7 Hz, 3H).

Example 40. Description of General Test Methods

Intrinsic MIC Assays

MIC assays were conducted in accordance with Clinical and Laboratory Standards Institute (CLSI) guidelines for broth microdilution. A 96-well plate containing cation-adjusted Mueller-Hinton (CAMH broth with 2-fold serial dilution of compounds was inoculated with log-phase bacterial at 5×10$^5$ CFU/mL. The final volume in each well was 100 µL. Each compound was tested in duplicate. The microtiter plates were incubated in an aerobic environment for 18 hours at 37° C. Then the bacterial growth was tested by reading the plate with a VersaMax plate reader (Molecular Devices, Inc.) at 600 nm. The MIC was defined as the lowest compound concentration that inhibited 90% of bacteria growth.

The intrinsic MIC of the experimental EPIs was tested with the method described. The 2-fold serial dilution begins with 100 µg/mL of tested compound in the first column of the 96-well plates. The following Gram-negative bacterial strains were included in these assays:

*Escherichia coli* ATCC 25922
*Klebsiella pneumoniae* ATCC 13883 and ATCC 10031
*Pseudomonas aeruginosa* ATCC 27853.
*Pseudomonas aeruginosa* PAO1
*Acinetobacter baumannii* ATCC 19606

MIC Assays in the Presence of a Bacterial Efflux Inhibitor

The EPI assay for the purposes of these studies represents a MIC assay in which the MIC of the antibiotic against the bacteria is tested in the presence of an experimental efflux pump inhibitor (EPI). The highest concentration of the EPI present in the assay typically is ½ of the intrinsic MIC of the compound. If the intrinsic MIC of the EPI is greater than 100 µg/mL, the EPI assay was tested with 50 µg/mL. Using serial dilutions of the EPI, its enhancement of antibiotic activity was then evaluated. The relative EPI activity was decided by comparing the MIC of the antibiotic in the presence of the EPI compound with the intrinsic MIC of the antibiotic alone. For comparative purposes, we generally used EPIs at concentration of 12.5 and 6.25 µg/ml against varying concentration of our test antibiotic.

Example 41

The following can illustrate representative pharmaceutical dosage forms, containing a compound of formula I, II, III, IV or V ('Compound X') or a pharmaceutically acceptable salt thereof, for therapeutic or prophylactic use in humans. The tablets can optionally comprise an enteric coating.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |

-continued

| (ii) Tablet 2 | mg/tablet |
|---|---|
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q. s. |
| Water for injection | q.s. ad 1 mL |

| (v) Injection 2 (10 mg/mL) | mg/mL |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. A compound of formula Ia:

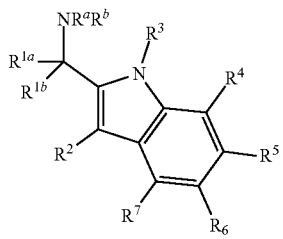

wherein the moiety

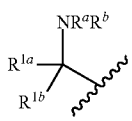

is:

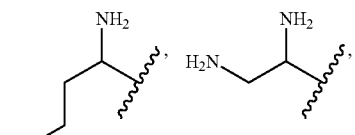

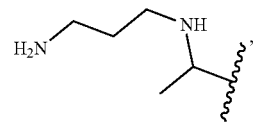

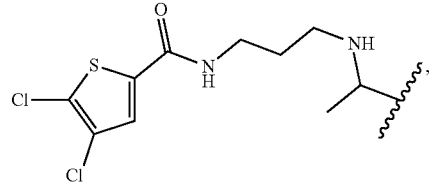

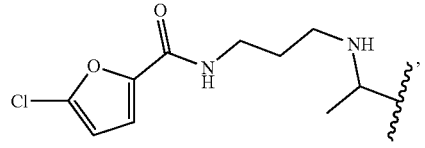

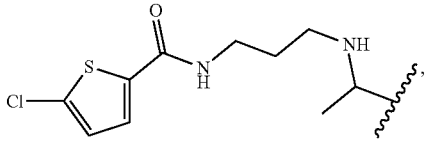

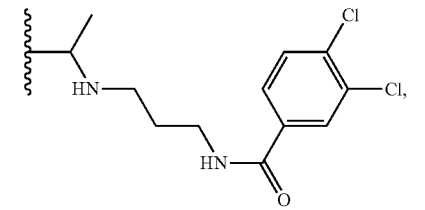

-continued

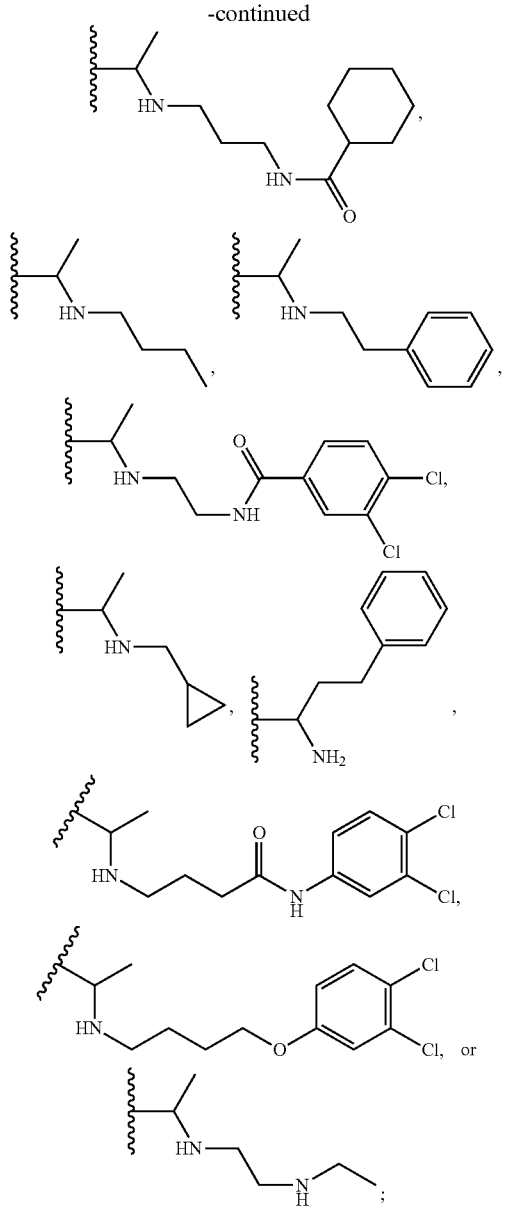

R₂ is hydrogen or (C₁-C₈)alkyl optionally substituted with one or more halo, hydroxyl, oxo, or NR$^a$R$^b$;

R³ is hydrogen or (C₁-C₄)alkyl;

R⁴ is hydrogen, halo, cyano, (C₁-C₆)alkyl, (C₁-C₆)haloalkyl, (C₁-C₆)alkoxy, (C₁-C₆)haloalkoxy, or phenyl wherein the phenyl is optionally substituted with one or more halo, (C₁-C₆)haloalkyl, cyano, nitro or (C₁-C₆)haloalkoxy;

R⁵ is hydrogen, halo, cyano, (C₁-C₆)alkyl, (C₁-C₆)haloalkyl, (C₁-C₆)alkoxy, (C₁-C₆)haloalkoxy, or phenyl wherein the phenyl is optionally substituted with one or more halo, (C₁-C₆)haloalkyl, cyano, nitro or (C₁-C₆)haloalkoxy;

R⁶ is hydrogen, bromo, cyano, (C₁-C₆)alkyl, (C₁-C₆)haloalkyl, (C₁-C₆)alkoxy, (C₁-C₆)haloalkoxy, or phenyl wherein the phenyl is optionally substituted with one or more halo, (C₁-C₆)haloalkyl, cyano, nitro or (C₁-C₆)haloalkoxy; and R⁷ is hydrogen, halo, cyano, (C₁-C₆)alkyl, (C₁-C₆)haloalkyl, (C₁-C₆)alkoxy, (C₁-C₆)haloalkoxy, or phenyl wherein the phenyl is optionally substituted with one or more halo, (C₁-C₆)haloalkyl, cyano, nitro or (C₁-C₆)haloalkoxy;

each R$^a$ is independently hydrogen or (C₁-C₆)alkyl wherein the (C₁-C₆)alkyl is optionally substituted with one or more halo, hydroxyl, NR$^c$R$^d$, R$^g$, —C(=O)NR$^{e1}$R$^{e2}$, —OR$^f$, or —(C₁-C₃)alkyl-R$^f$;

each R$^b$ is independently hydrogen, or (C₁-C₆)alkyl wherein the (C₁-C₆)alkyl is optionally substituted with one or more halo, hydroxyl, or NR$^c$R$^d$;

each R$^c$ is independently hydrogen, (C₁-C₃)alkyl, —C(=O)R$^h$, phenyl, C₃-C₇carbocycle, or —(C₁-C₆)alkylphenyl wherein the phenyl, C₃-C₇carbocycle, or —(C₁-C₆)alkylphenyl is optionally substituted independently with one or more halo, cyano, (C₁-C₆)alkyl, or (C₁-C₆)haloalkyl;

each R$^d$ is independently hydrogen or (C₁-C₃)alkyl;

each R$^{e1}$ is phenyl optionally substituted independently with one or more halo, cyano, (C₁-C₆)alkyl, or (C₁-C₆)haloalkyl;

each R$^{e2}$ is independently hydrogen or (C₁-C₃)alkyl;

each R$^f$ is phenyl optionally substituted independently with one or more halo, cyano, (C₁-C₆)alkyl, or (C₁-C₆)haloalkyl;

each R$^g$ is independently 5-6 membered heteroaryl, phenyl, or C₃-C₇carbocycle wherein the 5-6 membered heteroaryl, phenyl, or C₃-C₇carbocycle is optionally substituted independently with one or more halo, cyano, (C₁-C₆)alkyl, or (C₁-C₆)haloalkyl; and each R$^h$ is independently 5-6 membered heteroaryl, phenyl, or C₃-C₇carbocycle wherein the 5-6 membered heteroaryl, phenyl, or C₃-C₇carbocycle is optionally substituted independently with one or more halo, cyano, (C₁-C₆)alkyl, or (C₁-C₆)haloalkyl;

or a salt thereof.

2. The compound of claim 1, wherein R³ is hydrogen or methyl.

3. The compound of claim 1, wherein R⁴ is hydrogen, halo, (C₁-C₆)haloalkyl, (C₁-C₆)alkoxy, or (C₁-C₆)haloalkoxy.

4. The compound of claim 1, wherein R⁵ is hydrogen, halo, (C₁-C₆)haloalkyl, (C₁-C₆)alkoxy, or (C₁-C₆)haloalkoxy.

5. The compound of claim 1, wherein R⁶ is hydrogen, bromo, (C₁-C₆)haloalkyl, (C₁-C₆)alkoxy, or (C₁-C₆)haloalkoxy.

6. The compound of claim 1, wherein R⁷ is hydrogen, halo, (C₁-C₆)haloalkyl, (C₁-C₆)alkoxy, or (C₁-C₆)haloalkoxy.

7. The compound of claim 1, wherein at least one of R⁴, R⁵, R⁶, or R⁷ is bromo, (C₁-C₆)haloalkyl, (C₁-C₆)alkoxy, or (C₁-C₆)haloalkoxy.

8. A compound that is:

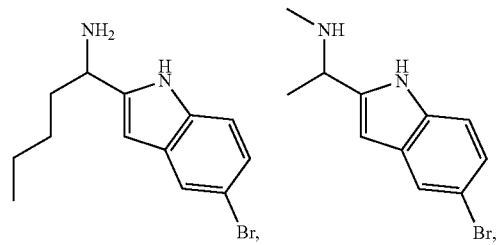

149
-continued
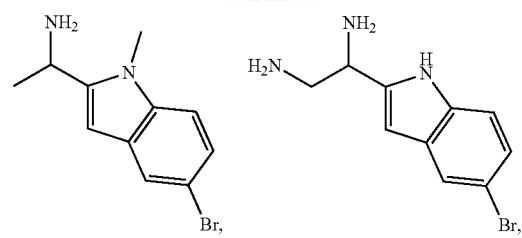
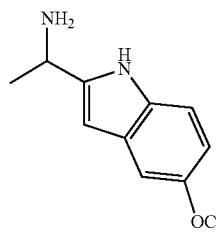 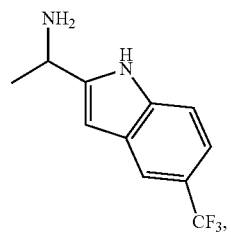
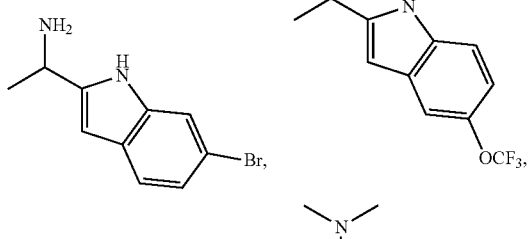
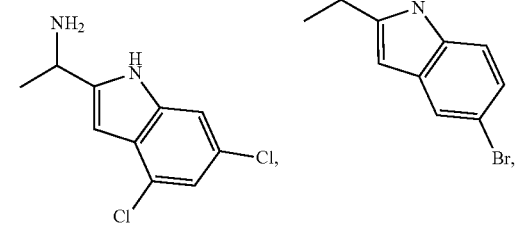
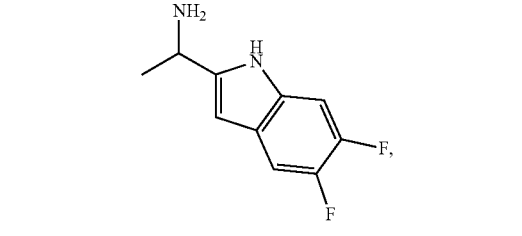
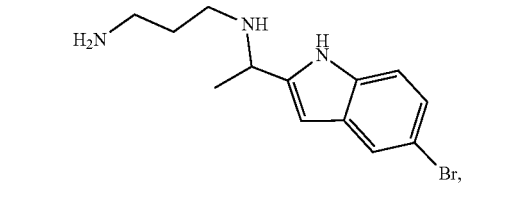
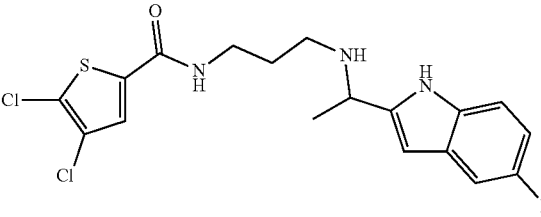
150
-continued
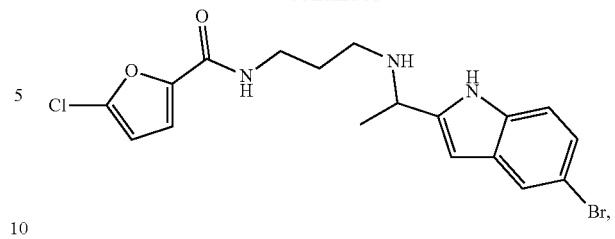

-continued

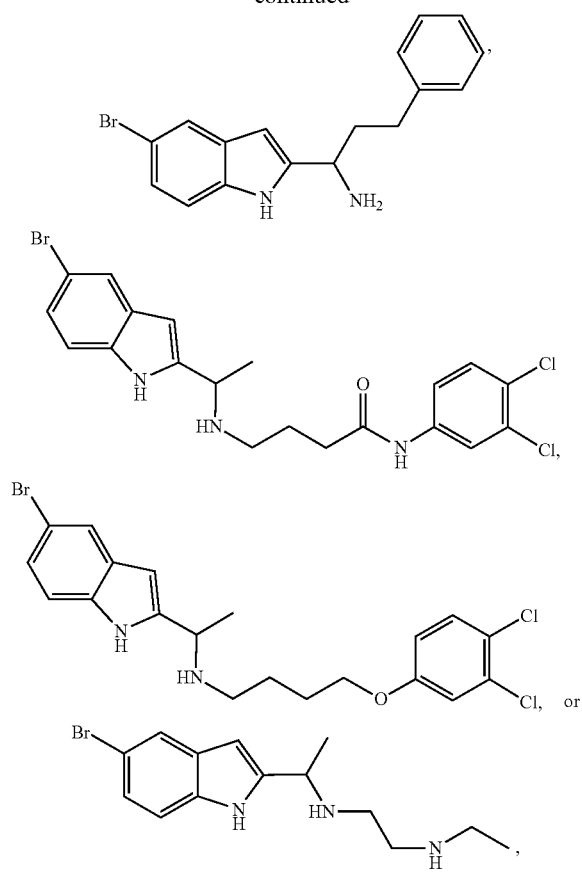

or a salt thereof.

9. A pharmaceutical composition comprising a compound as described in claim 1 or a pharmaceutically acceptable salt thereof and a pharmaceutically acceptable excipient.

10. A method of treating a bacterial infection in an animal comprising administering to the animal a compound as described in claim 1 or a pharmaceutically acceptable salt thereof.

11. A method of treating a bacterial infection in an animal comprising administering to the animal a bacterial efflux pump inhibitor and a compound as described in claim 1 or a pharmaceutically acceptable salt thereof.

12. A pharmaceutical composition comprising a compound as described in claim 1 or a pharmaceutically acceptable salt thereof, a bacterial efflux pump inhibitor, and a pharmaceutically acceptable vehicle.

13. A pharmaceutical composition comprising a compound as described in claim 8 or a pharmaceutically acceptable salt thereof and a pharmaceutically acceptable excipient.

14. A method of treating a bacterial infection in an animal comprising administering to the animal a compound as described in claim 8 or a pharmaceutically acceptable salt thereof.

15. A method of treating a bacterial infection in an animal comprising administering to the animal a bacterial efflux pump inhibitor and a compound as described in claim 8 or a pharmaceutically acceptable salt thereof.

16. A pharmaceutical composition comprising a compound that is:

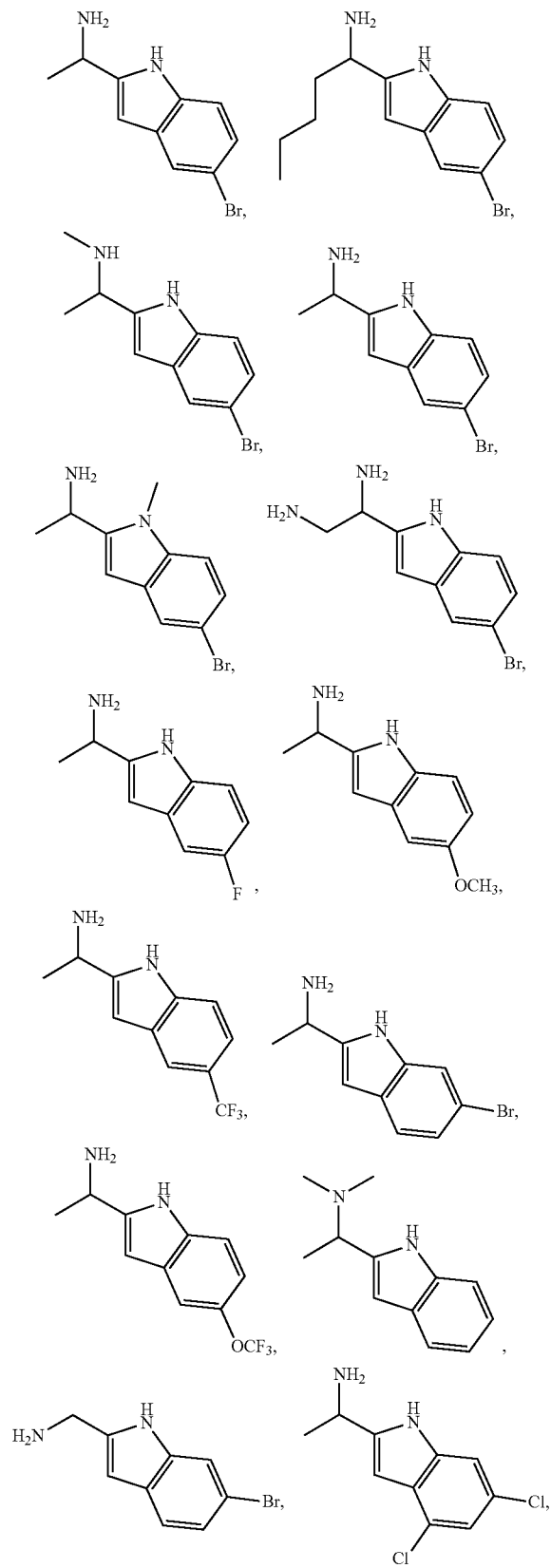

-continued
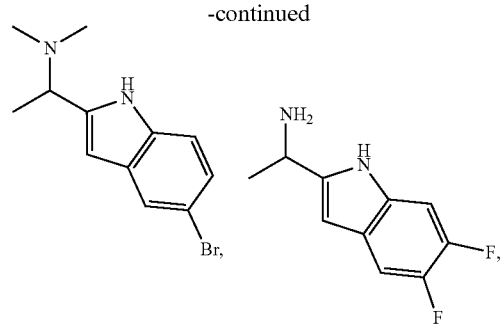
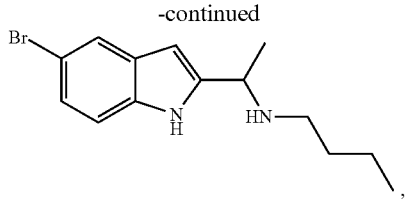
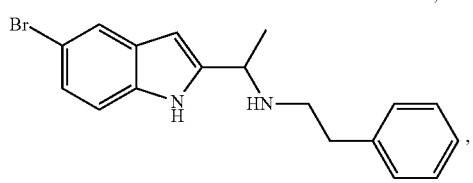
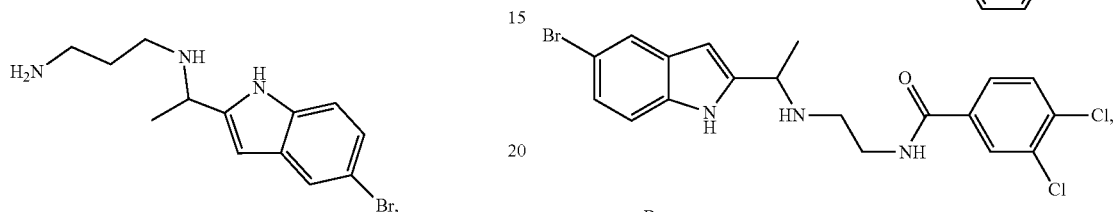
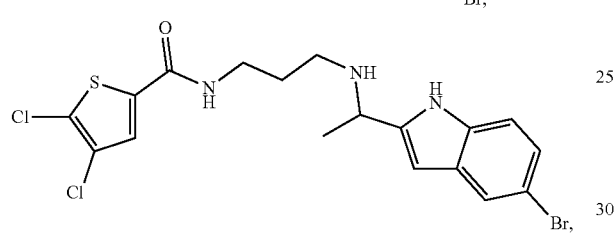
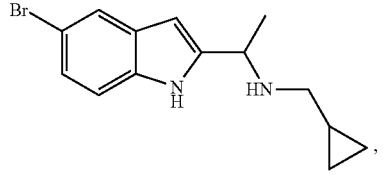
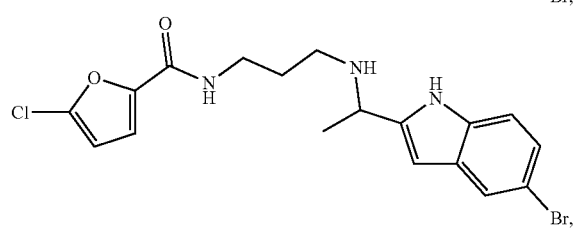
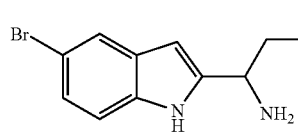
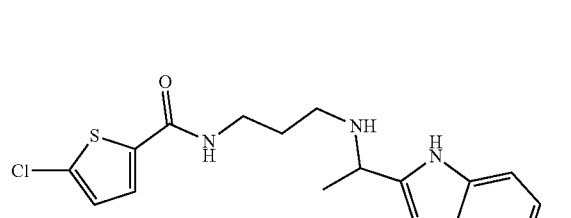
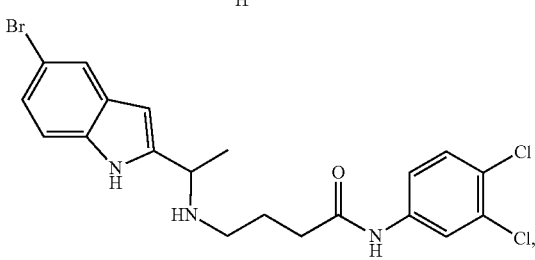
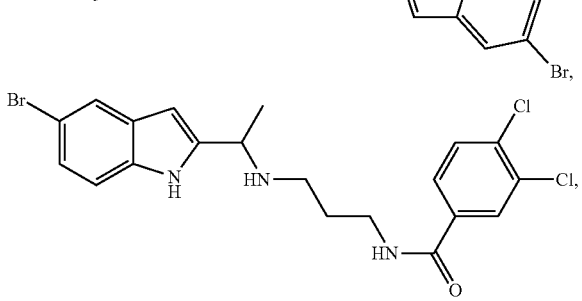
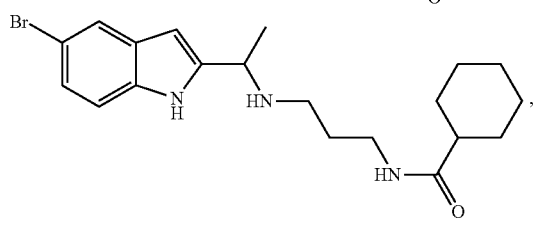
or a pharmaceutically acceptable salt thereof, a bacterial efflux pump inhibitor, and a pharmaceutically acceptable vehicle.

17. The compound of claim 1, wherein $R^2$ is hydrogen or $(C_1-C_8)$alkyl.

18. The compound of claim 1, wherein $R^2$ is hydrogen.

* * * * *

UNITED STATES PATENT AND TRADEMARK OFFICE
CERTIFICATE OF CORRECTION

PATENT NO. : 11,845,742 B2  
APPLICATION NO. : 16/763521  
DATED : December 19, 2023  
INVENTOR(S) : Edmond J. LaVoie, Hye Yeon Sagong and Ajit K. Parhi Page 1 of 1

It is certified that error appears in the above-identified patent and that said Letters Patent is hereby corrected as shown below:

In the Claims

Column 148, Line 7, Claim 1, please delete "$(C_1-C_3)alkyl-R^f$" and insert --$O(C_1-C_3)alkyl-R^f$--; and Column 152, Line 15, Claim 16, please delete " 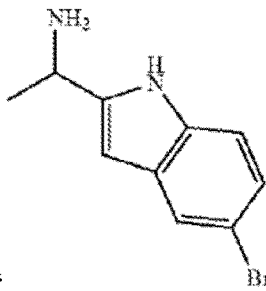 ," and insert

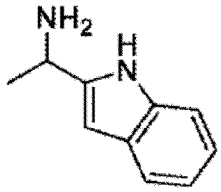

-- '-- therefor.

Signed and Sealed this  
Nineteenth Day of November, 2024

Katherine Kelly Vidal  
*Director of the United States Patent and Trademark Office*